us007339065B2

United States Patent
Avery et al.

(10) Patent No.: US 7,339,065 B2
(45) Date of Patent: Mar. 4, 2008

(54) DESIGN AND SYNTHESIS OF OPTIMIZED LIGANDS FOR PPAR

(75) Inventors: Mitchell A. Avery, Oxford, MS (US); Harrihar A. Pershadsingh, Bakersfield, CA (US)

(73) Assignees: Bethesda Pharmaceuticals, Inc., Bakerfield, CA (US); The University of Mississippi, University, MS (US)

( * ) Notice: Subject to any disclaimer, the term of this patent is extended or adjusted under 35 U.S.C. 154(b) by 0 days.

(21) Appl. No.: 10/565,492

(22) PCT Filed: Jul. 21, 2004

(86) PCT No.: PCT/US2004/023661

§ 371 (c)(1), (2), (4) Date: May 23, 2006

(87) PCT Pub. No.: WO2005/009437

PCT Pub. Date: Feb. 3, 2005

(65) Prior Publication Data

US 2007/0099969 A1    May 3, 2007

Related U.S. Application Data

(60) Provisional application No. 60/489,244, filed on Jul. 21, 2003.

(51) Int. Cl.
*A61K 31/426* (2006.01)
*C07D 277/34* (2006.01)

(52) U.S. Cl. .................................. 548/183; 514/369
(58) Field of Classification Search ................ 548/183
See application file for complete search history.

(56) References Cited

FOREIGN PATENT DOCUMENTS

WO    WO 02/076177    10/2002

OTHER PUBLICATIONS

Schiffrin, Am. J. Physiol. Heart Circ. Physiol., (2005), 288, pp. H1037-H1043.*
Staels et al., Diabetes, (Aug. 2005), vol. 54, pp. 2460-2470.*
McGeer, Biodrugs, 2005, 19(1), pp. 31-37.*

* cited by examiner

*Primary Examiner*—Laura L. Stockton
(74) *Attorney, Agent, or Firm*—Hunton Williams LLP; Eugene C. Rzucidlo

(57) ABSTRACT

This invention provides new chemical entities useful for treating a variety of clinical disorders including those that are influenced by the activity of peroxisome proliferator activated receptors (PPAR). The structures of the compounds and methods to design, make and use the compounds are provided. Compounds and methods for administering therapeutic compositions comprising the compounds in cases of the disease psoriasis are provided. An exemplary compound having the formula compound is 5adamantan-2-yl-pentanoic acid {2-[4-(2,4-dioxo-thiazolidin-5-yl-methyl)-phenoxy]-ethyl}-methyl-amide is provided.

6 Claims, No Drawings

DESIGN AND SYNTHESIS OF OPTIMIZED LIGANDS FOR PPAR

CROSS-REFERENCE TO RELATED APPLICATIONS

This application claims the benefit of priority to U.S. Provisional Application No. 60/489,244, filed Jul. 21, 2003 the contents of which are incorporated by reference herein in their entirety.

FIELD OF THE INVENTION

This invention relates to the field of rational drug design. Specifically the invention relates to compounds that interact with peroxisome proliferator activated receptors (PPARs) and methods for their design and synthesis. More specifically, the invention relates to methods of using PPAR interactive compounds for the treatment of psoriasis.

BACKGROUND OF THE INVENTION

Peroxisome proliferator-activated receptors (PPARs) are members of the nuclear receptor superfamily of ligand-activated transcription factors. Three subtypes of PPARs have been cloned from the mouse and human: i.e., PPARalpha, PPARgamma and PPARdelta. In humans PPARgamma and PPARalpha are differentially expressed in organs and tissues (Willson et al. *J. Med. Chem.* 43:527-50 (2000) Nuclear receptors like PPAR possess DNA binding domains (DBDs) that recognized specific DNA sequences (called response elements) located in the regulatory regions of their target genes Mangelsdorf et al *Cell* 83:835-839 (1995)). Activation of PPARs modulates the expression of genes containing the appropriate respective peroxisome proliferator response elements (PPRE) in its promoter region. PCT WO/25226.

PPARgamma consists of three forms, PPARgamma1 which is broadly expressed in most tissues, PPARgamma2, is more restricted to adipose (white fat and brown fat) tissue, and PPARgamma3. PPARgamma3 is confined to adipose tissue, macrophages and colonic epithelium in rodent and human tissues (Mangelsdorf, and Evans. *Cell* (1995) 83:841-850; Spiegelman. *Diabetes* (1998) 47:507-514; Willson et al., *J. Med. Chem.* (2000) 43:527-550). The distribution of the other PPARs also varies in different tissues. Throughout this writing PPAR refers to any of these isoforms, subtypes or combination thereof. PPARgamma is functionally involved in intermediary metabolism of cells and tissues that express this nuclear receptor.

PPARgamma and PPARalpha and PPARdelta are differentially expressed in different organs and tissues. Activation of PPARgamma and/or PPARalpha and/or PPARdelta modulates the expression of genes involved in: 1) glucose and lipid metabolism, 2) the regulation of cell growth, differentiation and regulation of the mitotic cycle, 3) the inflammatory response in cells of the immune system, 4) suppression of components of the immune system that become activated in pathological situations, and 5) regulation of apoptosis (programmed cell death) in a variety of cell types. Impairment in these processes lead to pathophysiolgical conditions involving metabolic (endocrine) dysfunction, proliferative diseases, inflammatory diseases and degenerative diseases. (Pershadsingh, *Expert Opin. Investig. Drugs* 8(11):1859-1872 (1999)).

The precise mechanism whereby ligand activation of PPARs lead to changes in gene expression is poorly understood. Full activation of PPARgamma and/or PPARalpha and/or PPARdelta requires its functional dimerization with the retinoid X receptor (RXR) to form PPARgamma/RXR or PPARalpha/RXR or PPARdelta/RXR. The endogenous ligand for RXR is 9-cis-retinoic acid. Nutrient retinoids and retinoic acid such as 13-all-trans-retinoic acid are converted to 9-cis-, 11-cis-, or 13-cis-retinoic acid by ubiquitous intracellular isomerases (Warrell Jr et al., *New Engl. J. Med.* 329(3):177-189 (1993)). The full spectrum of genes that can be regulated by PPARalpha or PPARgamma or PPARdelta or their respective heterodimers remain to be defined.

PPAR agonists have been shown to inhibit the expression of inflammatory cytokines such as tumor necrosis factor-alpha (TNF-alpha), IL-1, IL-2, IL-6 in cells of the immune system including, T lymphocytes, B lymphocytes, monocytes, monocyte/macrophages, and splenocytes. PPARgamma agonists tend to suppress inflammation mediated by Th1 lymphocytes (Marx et al., *J. Immunol.* 164:6503 (2000); Padilla et al., *Ann N.Y. Acad. Sci.* 905:97 (2000); Clark et al., *J. Immunol.* (2000) 164:1364; Yang et al., *J. Biol. Chem.* (2000) 275:4541). However, the anti-inflammatory effects of PPARgamma are controversial. It has been reported that PPARgamma activators are not useful for the treatment of acute inflammation in db/db diabetic mice (Thieringer et al., *J. Immunol.* (2000) 164:1046). Thiazolidinedione-treated db/db mice challenged with lipopolysaccharide, a potent pro-inflammatory agent, displayed no suppression of cytokine production. Rather, their blood levels of TNF-alpha and IL-6 were elevated beyond the levels observed in control mice.

PPAR agonists have also been shown to inhibit proliferation and promote differentiation of a variety of normal and neoplastic cell types. Spiegelman et al., PCT/US97/22879, published Jun. 18, 1998, disclose methods for inhibiting proliferation of PPARgamma-responsive hyperproliferative cells by using PPARgamma agonists; numerous PPARgamma agonists are disclosed by Spiegelman et al., as well as methods for diagnosing PPARgamma-responsive cells. The method relates to superior efficacy of PPAR activators or co-activators of various subtypes in: 1) promoting apoptosis of neoplastic cells, 2) systemic anti-inflammatory effect by suppressing Th1-mediated inflammatory cytokines and promoting Th1 to Th2 phenotypic transition resulting in of immunosuppression, leading to prevention, amelioration or reversal of degenerative diseases.

Examples of diseases susceptible to the immunosuppressive effects of activators of PPARgamma, or PPARalpha, or PPARdelta, or co-activators of any of these subtypes are: inflammatory skin diseases (e.g. psoriasis, atopic dermatitis, eczema, acne vulgaris, and other dermatitides), neurodegenerative diseases (e.g. multiple sclerosis, Alzheimer's disease, Parkinson's disease), cardiovascular diseases (e.g. atherosclerosis, venous and arterial occlusive diseases, restenosis after invasive procedures, cardiomyopathy, myocardial fibrosis, congestive heart failure), pulmonary disorders (asthma, chronic obstructive pulmonary disease), angiogenesis and neovascularization in neoplastic and other diseases. The immune system includes T lymphocytes, B lymphocytes, monocytes, macrophages, monocyte/macrophages, macrophage-like cells (e.g. astrocytes in the brain, retinal pigmented epithelial cells in the retina), cells of myeloid origin in any tissue, in particular the bone marrow (stem cells, pre-promyelocytes, promyelocytes, myelocytes, granulocytes, plasma cells, mast cells, basophils, polymorphonuclear cells, eosinophils).

In humans, PPARgamma and PPARalpha and PPARdelta are differentially expressed in organs and tissues (Willson et al., *J. Med. Chem.* (2000) 43 (4):527-50). This heterogeneous distribution is particularly evident in the complex structure of the eye (Braissant et al., *Endocrinology* (1996) 137:354-366; Pershadsingh et al., Proceedings of the Society for Neurosciences. Miami Beach, USA, 1999). It can be difficult to predict what cells and diseases are influenced by PPARgamma and/or PPARalpha activity and/or PPARdelta due to the varied tissue distribution of expression of the various PPAR subtypes and the varied amounts of their respective proteins in various cells (Escher et al., *Endocrinology* 142(10):4195-202 (2001); Braissant O, Wahli W, *Endocrinology* 139(6):2748-54 (1998)). Further, some PPAR subtypes are expressed in some cells while in a normal state, but not expressed or expressed to a lesser or greater degree by the abnormal cells, or visa versa. Specifically, PPARgamma and PPARalpha are differentially expressed in diseased versus normal cells. For example PPARgamma is expressed in normal human keratinocytes but not in normal human dermal fibroblasts (Ellis et al., *Arch. Dermatol.* (2000) 136:609-616). PPARgamma has been shown to be expressed in a greater amount in level was increased in the subcellular cytosolic fraction of Alzheimer's disease brains, compared to control brains (Kitamura et al., *Biochem. Biophys. Res. Commun.* 1999; 254:582-586).

The activity of PPARgamma or PPARalpha or PPARdelta depends on the degree to which the receptor protein is phosphorylated and/or on the conformation of the receptor. It has been proposed that phosphorylation could alter interactions with protein cofactors of PPARgamma which act as corepressors or coactivators. Nuclear receptors function as "ligand-gated" platforms for the assembly of these cofactors into large protein complexes on specific DNA sequences (Spiegelman *Diabetes* (1998) 47:507-514). Some of these coactivator proteins (CBP/p300, SRC1, pCAF) have histone acetyltransferase activity that functions to "open" the configuration of chromatin, allowing more efficient transcription. Others act as deacetylases which oppose the effects of acetyltransferases. Similar arguments apply to PPARalpha modulation of gene transcription. One theoretical problem is whether the nuclear receptor coactivators or corepressors identified to date are selective for particular PPAR receptors, and this remains unknown (Spiegehnan B M. *Diabetes* (1998) 47:507-514). In fact, these coactivators or corepressors have multiple modes of action and hence, it is not clear which cofactors are more important for the function of any particular receptor (Puigserver et al., *Science* (1999) 286: 1368-1371. It is also not obvious how the tremendous specificity of biological actions of the individual nuclear receptors are generated (Spiegelman, *Diabetes* (1998) 47:507-514). Consequently, the full spectrum of nuclear cofactors that regulate the transcriptional activity of PPARgamma and/or PPARalpha or PPARgamma/RXR and/or PPARalpha/RXR remains to be defined. The way in which a tissue expressing PPARgamma and/or PPARalpha and/or PPARdelta may respond to a particular ligand, and a pathological state will be attenuated, arrested, accentuated or worsened by said ligand can vary for example in the case in which a single ligand activates both PPARgamma and PPARalpha to similar degrees, i.e. a co-activator of both PPARgamma and PPARalpha (or similarly, both PPARgamma and PPARdelta or PPARalpha and PPARdelta).

Until recently, the genes regulated by PPARs were those believed to be predominantly associated with lipid and glucose metabolism. Recently, an immunomodulatory role for PPARgamma and PPARalpha has been described (Shu et al., *Biochem. Biophys. Res. Commun.* (2000) 267(1):345-9). The immunomodulatory/immunological mechanisms underlying inflammatory diseases mediated by or related to T lymphocyte activation are not well understood. Immunosuppressive agents capable of blocking various steps of the immune response have been utilized to prevent, ameliorate or reverse the inflammatory process, often by downregulating critical nuclear transcription factors that, in turn, regulate the expression of genes encoding inflammatory cytokines. Production of inflammatory cytokines occur in hypertriglyceridemic and other dyslipidemic states, e.g. diabetes mellitus.

Both PPARalpha and PPARgamma activators have been shown, independently, to suppress expression of these inflammatory regulators, inhibit proliferation and promote apoptosis of pathological cellular phenotypes. Paradoxically and unexpectedly, the opposite case occurs wherein the therapeutic compositions are administered in the treatment of degenerative disease such as multiple sclerosis (a neurodegenerative) or retinopathies and retinitis (retinal degenerative diseases), in which prevention of apoptosis is the operative mechanism. Therefore, in these disease states, activation of PPARalpha and PPARgamma by suppressing transcription of inflammatory cytokines, prevents apoptosis of the target cell and promotes survival of the non-pathological cellular phenotype. For example, in the case of multiple sclerosis, an autoimmune T lymphocyte-mediated disease, the target cell sustaining the pathological insult is the myelin sheath (oligodendrocyte) in the central nervous system. The pathological cellular phenotypes are amnestic T lymphocytes lacking immune recognition of oligodendrocytes, and inappropriately activated microglia, resulting in inappropriately activation and production of harmful inflammatory cytokines (Zhang et al., *Mult. Scler* (2000) 6:3-13). PPARgamma activation can inhibit neuronal apoptosis and promote neuronal protection through the upregulation of neuronal apoptosis inhibitory protein (Magun et al., *Diabetes* (1998) 47:1948-52). Indeed, PPARgamma activation protects cerebellar granule cells from cytokine-induced apoptotic cell death (Heneka et al., *J. Neuroimmunol.* (1999) 100:156-68). Moreover, PPARalpha has been shown to suppress inflammatory cytokines and nuclear factors in monocyte/macrophages. A similar mechanism involving suppression of inflammatory cytokine production by microglia would prevent oligodendrocyte apoptosis. Finally, combined PPARalpha/PPARgamma activation could promote Th1/Th2 differentiation as a final common pathway to inhibit apoptosis of the non-pathological phenotype and promotion of neuronal protection (Giorgini et al., *Horm. Metab. Res.* (1999) 31:1-4; Clark et al., *J. Immunol.* (2000) 164:1364-71).

PPARgamma interactions with co-activators and co-repressors tend to be ligand-specific. For example, the natural PPARgamma ligand, 15-deoxy-delta-12,14-prostaglandin J2 can induce the receptor-ligand complex to interact with the cofactors: SRC-1, TIF2, AMB-1, p300, TRAP220/DRIP205, whereas, under the same conditions the antidiabetic thiazolidinedione, troglitazone, a synthetic PPARgamma ligand does not. Therefore, ligand binding may alter PPARgamma structure in a ligand-type specific way, resulting in distinct PPARgamma-coactivator interactions (Kodera et al., *J. Biol. Chem.* (2000) 275(43):33201-33204. By analogy, a similar mechanism would provide ligand-specific control of gene expression in the case of PPARalpha activation or PPARdelta activation.

SUMMARY OF THE INVENTION

This invention involves the discovery of new chemical entities that have utility for treating a variety of clinical disorders including those that are influenced by the activity of peroxisome proliferator activated receptors (PPAR) including PPARalpha, PPARdelta, and or PPARgamma (the term "subtypes" is used herein to refer to the various types of PPARs including PPARalpha, PPARdelta, and PPARgamma). The invention also involves the surprising finding that the compounds are potent activators of peroxisome proliferator activated receptors. Compounds and methods on how to design, make and use the compounds are described herein. The invention also describes tautomers, stereoisomers and derivatives of the subject compounds, and pharmaceutically acceptable salts and solvates thereof, and their uses in the treatment of metabolic, inflammatory, autoimmune, proliferative and degenerative diseases.

This invention describes novel compounds that activate PPARs and that are useful for the treatment of clinical disorders that are influenced by the activity of various PPAR subtypes. Methods of this invention include how to make and use the compounds for the treatment of a T lymphocyte-related or autoimmune, inflammatory, proliferative, dystrophic, degenerative diseases, such as those involving ischemia, angiogenesis, atherosclerosis, increased cell proliferation, immune mediated inflammation, neovascularization, and or apoptosis, by administering to a human or animal in need of treatment an effective amount of a PPARgamma activator, or a PPARalpha activator, or a co-activator of both PPARgamma and PPARalpha; or a PPARdelta activator to attenuate, reverse, prevent, ameliorate, or stop the disorder. Provided are thiazolidinedione and non-thiazolidinedione ligands, their esters, salts, solvates and tautomers and various derivatives of these ligands.

Pharmaceutical compositions comprising compounds disclosed herein, as wells as salts solvates, esters, tautomers or stereoisomers are provided. Optionally, the composition further includes a pharmaceutically acceptable excipient.

Also provided is a method for treating a peroxisome proliferator activated receptor (PPAR) mediated disease, or risk factor, wherein the method includes administering to a human or an animal in need thereof, a therapeutically effective amount of a compound according to any one of the compounds described herein. Optionally, the compound is a PPARgamma activator, PPARalpha activator, or PPARdelta activator.

Also provided is a method wherein the compound is administered in combination with a natural or a synthetic therapeutic compound. Optionally, the compound is administered with a pharmaceutical excipient.

In one aspect of the invention, the PPAR mediated disease is psoriasis. In one embodiment the compound is 5-adamantan-2-yl-pentanoic acid {2-[4-(2,4-dioxo-thiazolidin-5-ylmethyl)-phenoxy]-ethyl}-methyl-amide, or BP 107.

DETAILED DESCRIPTION OF THE INVENTION

As used herein, the term "alkyl" includes a branched or unbranched hydrocarbon chain, for example, including about 1 to about 8 carbons, such as methyl, ethyl, n-propyl, iso-propyl, n-butyl, sec-butyl, iso-butyl, tert-butyl, octadecyl and 2-methylpentyl. Alkyl can be optionally substituted with one or more functional groups which are attached commonly to such chains, such as hydroxyl, bromo, fluoro, chloro, iodo, mercapto or thio, cyano, alkylthio, aryl, carboxyl, carbalkoyl, alkyl, alkenyl, nitro, amino, alkoxyl, amido, and the like to form substituted alkyl groups such as trifluoro methyl, 3-hydroxyhexyl, 2-carboxypropyl, 2-fluoroethyl, carboxymethyl, cyanobutyl and the like. The term "cycloalkyl" includes a cyclic alkyl.

The term "heteroalkyl" includes a branched or unbranched hydrocarbon chain having one or more heteroatoms in between carbon atoms. The term "heterocycle" includes a hydrocarbon chain forming one or more rings and having one or more heteroatoms in the ring. Alkylheterocycles include alkyl groups attached to heterocycles. Alkylheteroaryls include alkyl groups attached to heteroaryls. Heteroalkyl and heterocyclic groups may be substituted for example as described for alkyl groups.

The term "aryl" includes a chain of carbon atoms which form at least one aromatic ring having for example between about 6-14 carbon atoms, such as phenyl, naphthyl, and the like. The aryl optionally may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like. Aryl and substituted aryl groups include biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolyhnethylphenyl, and the like.

The term "heteroaryl" includes a ring system including one or more aromatic rings and containing one or more heteroatoms, N, O, or S, in the aromatic ring. Heteroaryl groups can be unsubstituted or may be substituted for example as described for alkyl groups.

The term "acyl" refers to moiety of the formula —C(O)R', wherein R' is for example alkyl, aryl, heteroaryl, heterocyclic; such as formyl, acetyl, propionyl, or butyryl.

This invention relates to the synthesis and uses of new compounds to treat diseases of multiple organ systems, including those contained in the cardiovascular system, pulmonary system, integumentary system, skeletal system, bone marrow, immune system, central and peripheral nervous system, endocrine and exocrine glands, urogenital system, and gastrointestinal system, and other tissues that express peroxisome proliferator-activated nuclear receptors (PPARs), including PPARalpha, gamma and delta, a family of nuclear transcription factors. PPARγ includes the $\gamma_1$, $\gamma_2$ or $\gamma_3$ isotypes or a combination of all three isotypes. PPARs are nuclear receptors which naturally bind to fatty acids and which have been implicated in adipocyte differentiation (Perlmann & Evans, Cell, 90:391-397 (1997)).

This invention further relates to modulating the activity of nuclear transcription factors or other factors that are involved in the promotion of diseases involving derangements in: lipid and carbohydrate metabolism, inflammation, proliferation, differentiation, pathological activation of lymphocytes, apoptosis, nitric oxide formation, matrix metalloproteinases (MMPs), and tissue inhibitors of MMPases (TIMPs) by pharmaceutically acceptable forms including salts and solvates of the compounds described herein. PPARalpha has been shown to have substantial anti-lipemic and anti-dyslipidemic properties which contribute to their anti-inflammatory and anti-apoptotic activities, and their efficacy in the treatment of vast array of pathologies and diseases (see Tables I through X inclusive).

Another aspect of this invention relates to methods and uses of PPARgamma activators, or PPARalpha activators, or PPARdelta activators or co-activators of any combination of the PPAR, subtypes, for treating inflammatory immune-mediated diseases by suppressing acute and chronic inflammatory production of inflammatory cytokines, and by promoting phenotypic transition of lymphocytes from the Th1 to the Th2 phenotype.

In another aspect, this invention relates to the subject compounds in the treatment of the diseases listed in Tables I through Table X, administered as either as a single agent, or in combination with a natural or synthetic compounds. Such compounds include agonists for PPARalpha, PPARdelta, PPARgamma, retinoid X receptor (RXR), vitamin D receptor (VDR), glucocorticoid receptor (GR), Liver X receptor (LXR) or LXR/RXR (e.g. an oxysterol (22(R)-hydroxycholesterol, 25-hydroxycholesterol, 7a-hydroxycholesterol, 24-hydroxycholesterol, 27-hydroxycholesterol, 40-hydroxycholesterol, 20,22-dihydroxycholesterol, and 20(S)-hydroxycholesterol, or a synthetic, synthetic nonsteroidal LXR-selective agonist (represented by T0314407 and T0901317, Schultz et al., *Genes Dev.* 14(22):2831-8 (2000)), Farnseoid X receptor (FXR) or FXR/R (e.g. farnesol, chenodeoxycholic acid, a bile acid), and beta3-adrenoceptor. The compounds of this invention can also be, administered as either a single agent, or in combination with a natural or synthetic compounds that include inhibitors for 3-hydroxy-3-methylglutaryl coenzyme A (HMG-CoA) reductase (e.g. atorvastatin; cerivastatin, fluvastatin, lovastatin, pravastatin, simvastatin, rosuvastatin), and cholesterol ester transfer protein (CETP) (e.g. a substituted-1,2,3,4-tetrahydroquinoline). The compounds of this invention can also be administered as either a single agent, or in combination with a natural or synthetic compounds that can include a pharmacological agent that increases the expression or upregulates the ATP-binding cassette protein 1 (ABC1), calcineurin inhibitor (e.g. cyclosporine A, tacrolimus, sirolimus), an anti-hypertensive angiotensin converting enzyme (ACE) inhibitor (e.g. benazepril, captopril, cilazapril, enalapril, enalaprilat, fosinopril, lisinopril, moexipril, perindopril, quinapril, ramipril, trandolapril), or an anti-hypertensive angiotensin receptor blocker (ARB)(e.g. losartan, valsartan, irbesartan, candesartan), telmisartan, eprosartan).

In another aspect, the present invention generally relates to the treatment of T lymphocyte-related diseases that involve activation of nuclear factor of activated T lymphocyte NFAT, NF-kappaB or AP-1, inappropriate activation of nuclear transcription factors that regulate the transcription of genes encoding inflammatory cytokines, inappropriate transcription of genes encoding said inflammatory cytokines, and increased secretion and activity of said inflammatory cytokines. Examples of cytokines relating to this invention include, but are not limited to interferon-gamma (INF-gamma), tumor necrosis factor-alpha (TNF-alpha), and a variety of the inflammatory and immunomodulatory interleukins (Chinetti et al. J. Biol. Chem. 1998; 273:25573-25580; Escher and Wahli, Mutat. Res. 2000; 448:121-138; Ricote et al., J. Leukoc. Biol. 1999; 66:733-739; Rocchi and Auwerx, Ann. Med. 1999; 31:342-351). This invention further relates to the prevention or treatment of disorders of inflammatory and immunomodulatory responses of the immune system involving: T helper ($T_H$), T suppressor ($T_S$), Th1 and Th2 lymphocytes, natural killer (NK) and other T cell subsets; the T cell receptor (TCR) and cellular signal transduction pathways initiated by TCR activation; the major histocompatibility complex (MHC) and cellular transduction pathways initiated by MHC activation. Inflammatory cytokine produced by T lymphocytes include but not limited to: IL-1alpha, IL-1beta, IL-2, IL-4, IL-6, IL-8, IL-9, IL-11, IL-12, IL-15, IL-16, IL-18, TNF-alpha or INFgamma. Lymphoid-specific and other ubiquitous transcription factors include but are not limited to NFAT, NF-IL2A, activated protein-1 (AP-1), nuclear factor-kappaB (NF-kappaB), Oct1, CD28; signal transducers and activator of transcription (STATs) which regulate DNA gene promoter sequences; oncogenes (e.g. c-myc, c-jun, c-fos), CD40/CD40L.

In another aspect, the present invention is directed to compounds including positional and optical isomers of the subject compounds having one or any combination of the following properties: anti-inflammatory activity, e.g. by blocking production of inflammatory cytokines; prevention of programmed cell death (apoptosis), e.g. in degenerative diseases; induction of programmed cell death (apoptosis), e.g. in neoplastic cells or malignancies; anti-proliferative activity by blocking mitosis or otherwise interrupting the cell cycle; anti-proliferative activity by promoting differentiation; anti-thrombotic or blood clot dissolving activity, e.g. inhibition of thrombin or GP IIb/IIIa; inhibitory effect on nitric oxide synthase (iNOS); inhibitory effect on matrix metalloproteinases (MMPase) e.g. gelatinases, collagenases, stromelysins, matrilysins, and/or their respective pro-enzymes; inhibition of the nuclear receptor, nuclear factor-kappaB (NF-kappaB); inhibition of the nuclear receptor, activated protein-1 (AP-1); and inhibition of the of the nuclear receptor, nuclear factor of activated T lymphocytes (NFAT).

In another aspect, the present invention generally relates to the treatment of diseases involving inappropriate apoptosis or inappropriate activation of the apoptotic programmed cell death pathway. Apoptotic regulators which malfunction resulting in pathological diseases or conditions include: fas/fasL, Apo-1/CD95, FADD, TRADD, Apo2L/TRAIL, the TNF receptor, caspases (in particular caspase-3), inducible nitric oxide (iNOS) gene transcription and nitric oxide production. Several of these components are regulated primarily or secondarily by PPARgamma and/or PPARalpha activation. (Delerive, et al., *J. Endocrinol.* 169 (3):453-9 (2001))

Synergistic Activation by PPARalpha and PPARgamma Ligands

Activation of both PPARalpha and PPARgamma have effects on metabolic risk factors that lead to chronic systemic inflammation that can result in diabetes, atherosclerosis, congestive heart failure, ulcerative colitis, rheumatoid arthritis, osteoporosis, Alzheimer's disease, multiple sclerosis, and other autoimmune and degenerative diseases (Pershadsingh, *Expert Opin. Investig. Drugs* 8:1859-1872 (1999); Neve et al., *Biochem. Pharmacol.* 60:1245-1250 (2000); McGeer et al., *J. Neural. Transm. Suppl.* 59:53-7 (2000); Bar-Or et al., *J. Neuroimmunol.* 100:252-9 (1999); Papadakis and Targan, *Annu. Rev. Med.* 51:289-98(2000)). Pharmacological co-activation of both subtypes provides for a synergistic therapeutic effect. An essential aspect of this invention is a unique and novel approach to the treatment of such diseases that involves the unexpected outcome, that simultaneous pharmacological activation of both PPARalpha and PPARgamma leads to superior efficacy, compared to the effects derived from the algebraic sum of the effects of activation of PPARalpha or PPARgamma, independently. Synergy may be achieved either with a ligand that co-activates both PPARalpha and PPARgamma subtypes, or therapeutic compositions consisting of a PPARalpha agonist and a PPARgamma agonist resulting in attenuating, arresting, reversing or preventing the target disease.

This aspect of the invention is illustrated in the unique approach to the treatment of atherosclerosis or psoriasis, that have dermatological or vascular manifestations of a chronic disease with inflammatory, proliferative and degenerative (apoptotic) components. The pathogenesis of both atherosclerosis and psoriasis involve inappropriate proliferation (vascular smooth muscle cells in atherosclerosis and epidermal keratinocytes in psoriasis) and expression of inflammatory cytokines, mediated by activation of the inflammatory transcription factors, NF-kappaB, AP-1 and NFAT (Neve et al., *Biochem. Pharmacol.*, 60:1245-1250 (2000) and Ellis et al., *Arch. Dermatol.* 136:609-16(2000)). Specific activation of PPARgamma on the one hand (Ellis et al., *Arch. Dermatol.* 136:609-16(2000)), and specific activation of PPARalpha on the other (Komuves et al., *J. Invest. Dermatol.* 115:353-60(2000)) have been shown to independently stimulate keratinocyte differentiation and inhibit and epidermal proliferation. Similarly, for example, activation of PPARgamma inhibits proliferation of vascular smooth muscle (VSM) cells, and iNOS production and matrix metalloproteinase (MMP) activity in the vessel wall, whereas activation of PPARalpha decreases the activity of cell adhesion moles and affects lipoprotein metabolism, resulting in a profound anti-dyslipidemic systemic effect (Neve et al., Biochem. Pharmacol. 2000; 60:1245-1250). Thus, unexpectedly, pharmacological co-activation of PPARalpha and PPARgamma can provide synergistic therapy in the treatment of atherosclerosis or psoriasis.

Via negative regulation of NF-kappaB and AP-1 signaling pathways, PPARalpha inhibits expression of inflammatory genes, such as interleukin-6, cyclooxygenase-2, endothelin-1, and the expression of monocyte-recruiting proteins such as vascular cell adhesion molecule (VCAM)-1, and recruitment of monocytes and foam cells in atherosclerotic lesions. Also via negative regulation of NF-kappaB and AP-1 signaling pathways, PPARgamma activation in macrophages and foam cells inhibits the expression of genes encoding iNOS, MMP-9, scavenger receptor A, VCAM-1. Therefore treatment modalities involving the simultaneous activation of PPARalpha and PPARgamma can provide a synergistic therapeutic effect and leading to superior improvement, resolution or prevention of systemic cardiovascular inflammation, including atherosclerosis, vascular restenosis, congestive heart failure and myocardial fibrosis (Takano et al., *Circ. Res.* 87:596-602(2000); Lee et al., *Circ. Res.*, 87:516-21 (2000); Fruchart et al., *Curt Opin. Lipidol.* 10:245-57 (1999)).

The compound may be a PPAR ligand with properties selected from the group consisting of: 1) a PPARgamma agonist, 2) a PPARgamma partial agonist (i.e. as SPARM (selective PPAR modulator), 3) a PPARgamma antagonist, 4) a PPARalpha agonist, 5) a PPARalpha partial agonist, 6) a PPARalpha antagonist, 7) a PPARdelta agonist, 8) a PPARdelta partial agonist, 9) a PPARdelta antagonist, 10) a PPARgamma/PPARalpha dual agonist), 11) a PPARgamma/PPARdelta dual agonist, 12) a PPARalpha/PPARdelta dual agonist, 13) a PPARgamma partial agonist that also activates PPARalpha, 14) a PPARgamma partial agonist that also activates PPARdelta, and 15) a ligand that activates all three PPAR isoforms, a PPARgamma/PPARalpha/PPARdelta pan-agonist.

In another aspect, the present invention relates to methods of associating a particular disease or condition with a particular nuclear receptor, for example, the nuclear receptor PPARgamma. By associating, is meant that a particular disease or condition can be treated by administration of a compound of this invention that activates or deactivates the particular nuclear receptor. As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

Compounds having formulae described herein can be prepared. The binding affinity of a compound of this invention to a particular receptor can be determined using well-described binding assays. The ability of a compound of this invention to activate a particular receptor can also be determined using well-described transcriptional activation assays.

Compounds According to the Invention

Exemplary compounds capable of interacting with PPAR receptors include the following:

Case 1 represents compounds of the formula:

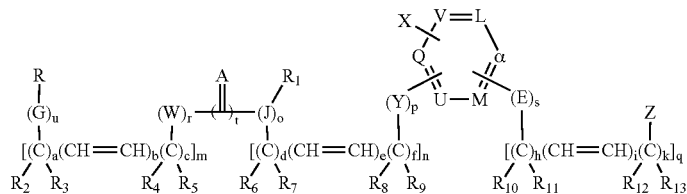

wherein the following apply:

a=0-8; c=0-8; d=0-8; f=0-8; h=0-8; k=0-8.

b=0-4; e=0-4; i=0-4 (when b, e or i are =1, double bonds are either E or Z; when b, e or i are >1, any mixture of E or Z diastereomers is possible).

m=0-4; n=0-4; q=0-4.

u=0, 1; r=0, 1; p=0, 1; s=0, 1; t=0, 1; o=0, 1.

A=O, S.

R, $R^1$-$R^{13}$=any combination of naught, H, lone pair of electrons, optionally substituted: alkyl, E or Z alkenyl, or alkynyl; heteroalkyl; E or Z heteroalkenyl, branched secondary or tertiary alkyl, branched secondary or tertiary E or Z alkenyl; branched secondary or tertiary heteroalkyl, branched secondary or tertiary E or Z heteroalkenyl. Optionally substituted (such as methyl, hydroxyl, thiol, carboxylate, aldehyde, heteroatom, and so on) cycloalkyl, benzocycloalkyl; alkylbenzocycloalkyl; hetero substituted alkylbenzocycloalkyl; alkylbenzocycloalkenyl; heterobenzocycloalkenyl; alkylcycloalkyl, alkylcycloalkenyl; alkenylcycloalkyl; alkenylcycloalkenyl. Optionally substituted (such as methyl, hydroxyl, thiol, carboxylate, aldehyde, heteroatom, and so on) spirobicycloalkyl, alkylspirobicycloalkyl, alkenylspirobicycloalkyl, alkylspirobicycloalkenyl, alkenylspirobicycloalkenyl, Optionally substituted (such as methyl, hydroxyl, thiol, carboxylate, aldehyde, heteroatom, and so on) bicycloalkyl; benzobicycloalkyl; alkylbenzobicycloalkyl; hetero substituted alkylbenzobicycloalkyl; alkylbenzobicycloalkenyl; heterobenzobicycloalkenyl; alkylbicycloalkyl, alkylbicycloalkenyl; alkenylbicycloalkyl; alkenylbicycloalkenyl; alkylbicycloalkyl, Optionally substituted (such as methyl, hydroxyl, thiol, carboxylate, aldehyde, heteroatom, and so on) tricycloalkyl; benzotricycloalkyl; alkylbenzotricycloalkyl; hetero substituted alkylbenzotricycloalkyl; alkylbenzotricycloalkenyl; heterobenzotricycloalkenyl; alkyltricycloalkyl, alkyltricycloalkenyl; alkenyltricycloalkyl; alkenyltricycloalkenyl; alkyltricycloalkyl; alkyltricycloalkyl. Optionally substituted (such as methyl, hydroxyl, thiol, carboxylate, aldehyde, heteroatom, and so on) tetracycloalkyl; benzotetracycloalkyl; alkylbenzotetracycloalkyl; hetero substituted alkylbenzotetracycloalkyl; alkylbenzotetracycloalkenyl; heterobenzotetracycloalkenyl; alkyltetracycloalkyl; alkyltetracycloalkyl; alkenyltetracycloalkyl; alkenyltetracycloalkenyl; alkyltetracycloalkyl; alkyltetracycloalkyl; alkyltetracycloalkyl. Optionally substituted (such as methyl, hydroxyl, thiol, carboxylate, aldehyde, heteroatom, and so on) bi-, tri-, tetra- and poly(heterocycloalkyll; alkyl bi-, tri-, tetra-, and poly(heterocycloalkyl); E or Z alkenyl bi-, tri-, tetra- and poly (heterocycloalkyl); polycycloalkyl; benzopolycycloalkyl; alkylbenzopolycycloalkyl; hetero substituted alkylbenzopolycycloalkyl; alkylbenzopolycycloalkenyl; heterobenzopolycycloalkenyl; alkylpolycycloalkyl; alkylpolycycloalkyl; alkenylpolycycloalkyl; alkenylpolycycloalkenyl; alkylpolycycloalkyl; alkylpolycycloalkyl; alkylpolycycloalkyl.

Optionally substituted (such as methyl, hydroxyl, thiol, carboxylate, aldehyde, heteroatom, and so on) aryl; alkylaryl; heteroaryl; alkylheteroaryl; ring-fused heteroaryls; alkyl substituted ring-fused heteroaryls; $R_6NH$, $R_6R_7N$, $R_8S$, $R_9SO$, $R_8SO_2$, $R_8SO_2NH$, $R_8SO_2NR_9$, $R_{10}CO$, $R_{10}OCO$, $R_{10}NHCO$, $R_{10}R_{11}NCO$, $R_{12}O$, $R_{13}SCO$, $R_{14}NCONHR_{15}$, $R_8NHSO_2NH$, $R_8NHSO_2NR_9$, $R_{10}NHCO$, $R_{10}OCONR_{16}$, $R_{10}NHCO$, $R_{10}R_{11}NCO$, $R_{13}SCONR_{17}$.

W=O, NH, $NR^1$, S, —S—S—, R or S or racemic —S(lone pair)O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

G=O, NH, $NR^1$, S, —S—S—, R or S or racemic —S(lone pair)O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

E=O, NH, $NR^1$, S, —S—S—, R or S or racemic —S(lone pair)O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

J=O, NH, $NR^1$ (e.g. N-Me), S, —S—S—, R or S or racemic —S(lone pair)O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—.

X=H, halogen, $OR^1$, O, NH, $NR^1$, S, —S—S—, R or S or racemic —S(lone pair)O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; —$CH_2$; —C=N—, with X attached either meta or para.

Y=H, O, $OR^1$, NH, $NR^1$, S, —S—S—, R or S or racemic —S(lone pair)=O—, —$SO_2$—, —SONH—, —NHSO—, —$NR^1SO$—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—, with Y attached either meta or para.

Q, L, M, V, α, and U are any combination of Q=CH, N,N-oxide; L=CH, N,N-oxide; M=CH, N,N-oxide, V=CH, N,N-oxide, α=CH, N,N-oxide, and U=CH, N and N-oxide; where the point of attachment of Y and X are usually via carbon atoms in the central ring. When X=OH and L=N, a 2- or 4-pyridinol is indicated, which automatically-includes the keto-tautomers, the 2- and 4-pyridones. The side chain ($Y_p$) can be attached via the pyridone N, or at one of the remaining positions. Also, the ring can be benzenoid, pyridinoid, pyrimidinoid, and so on where benzenoid is preferred.

Z=$CO_2R^1$; R or S or racemic 5-substituted-thiazolidine-2,4-dione; R or S or racemic 3-substituted-pyrrolidine-2,5-dione; all diastereomers of 3,4-disubstituted-pyrrolidine-2,5-dione; R or S or racemic 4-substituted-azetidine-2-one; R or S or racemic 3-substituted-azetidine-2-one; all diastereomers of 3,4-disubstituted-azetidine-2-one; 3-substituted-azetidine -2,4-dione; 1-substituted-1,3-diazetidine-2,4-dione; 1-substituted-1,3-diazetidine-2-one; all diastereomers of 1,4-disubstituted-1,3-diazetidine-2-one; 5-substituted-2,4-dihydro-[1,2,4]triazol-3-one; 4-hydroxy-5-substituted-1,2-dihydro-pyrazol -3-one; 4-alkoxy-5-substituted-1,2-dihydro-pyrazol-3-one; 4-alkoxy-substituted -1,2-dihydro-pyrazol-3-one; 5-substituted-2H-pyrazole-3,4-dione; 5-substituted-imidazole -2,4-dione; 3-substituted-pyrrole-2,5-dione; 3-Hydroxy-4-substituted-pyrrole -2,5-dione; 3-alkoxy-4-substituted-pyrrole-2,5-dione; 3-alkoxy-substituted-pyrrole-2,5-dione; 5-substituted-oxazolidine-2,4-dione; 5-substituted-imidazolidine-2,4-dione; 5-substituted-1,2-dihydro-pyrazol-3-one; 5-substituted-2H-tetrazole; 4-substituted-2H-[1,2,3]triazole; 3-substituted-1H-[1,2,4]triazole; R or S or racemic 5-substituted-3,5-dihydro-[1,2,3]triazol-4-one; 5-substituted-2,3-dihydro-[1,2,3]triazol-4-one; R or S or racemic 4-substituted-pyrazolidine-3,5-dione; 4-substituted-[1,2,4]

triazolidine-3,5-dione. Also, all benzo-fused examples of the above monocycles such as, but not limited to: 2, 3, 4 or 5-substituted-isoindole-1,3-dione; 3, 4 or 5-substituted-1,2-dihydro-indazol-3-one; 3, 4 or 5-substituted-2H-benzotriazole, and so on.

Compounds of Formula 1 are capable of interacting with PPAR receptors wherein Formula 1 corresponds to:

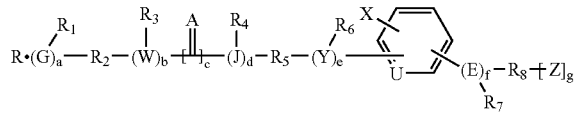

wherein the following apply:
  a=0 to 1; b=0 to 1; c=0-2; d=0 to 1; e=0 to 1; f=0 to 1.
  A=O or S.
  R, $R^1$-$R^{13}$=any combination of naught, H, lone pair of electrons, optionally substituted: alkyl, E or Z alkenyl, or alkynyl; heteroalkyl; E or Z heteroalkenyl; branched secondary or tertiary alkyl, branched secondary or tertiary E or Z alkenyl; branched secondary or tertiary heteroalkyl, branched secondary or tertiary E or Z heteroalkenyl. Optionally substituted (such as methyl, hydroxyl, thiol, carboxylate, aldehyde, heteroatom, and so on) cycloalkyl, benzocycloalkyl; alkylbenzocycloalkyl; hetero substituted alkylbenzocycloalkyl; alkylbenzocycloalkenyl; heterobenzocycloalkenyl; alkylcycloalkyl, alkylcycloalkenyl; alkenylcycloalkyl; alkenylcycloalkenyl. Optionally substituted (such as methyl, hydroxyl, thiol, carboxylate, aldehyde, heteroatom, and so on) spirobicycloalkyl, alkylspirobicycloalkyl, alkenylspirobicycloalkyl, alkylspirobicycloalkenyl, alkenylspirobicycloalkenyl, Optionally substituted (such as methyl, hydroxyl, thiol, carboxylate, aldehyde, heteroatom, and so on) bicycloalkyl; benzobicycloalkyl; alkylbenzobicycloalkyl; hetero substituted alkylbenzobicycloalkyl; alkylbenzobicycloalkenyl; heterobenzobicycloalkenyl; alkylbicycloalkyl, alkylbicycloalkenyl; alkenylbicycloalkyl; alkenylbicycloalkenyl; alkylbicycloalkyl, Optionally substituted (such as methyl, hydroxyl, thiol, carboxylate, aldehyde, heteroatom, and so on) tricycloalkyl; benzotricycloalkyl; alkylbenzotricycloalkyl; hetero substituted alkylbenzotricycloalkyl; alkylbenzotricycloalkenyl; heterobenzotricycloalkenyl; alkyltricycloalkyl, alkyltricycloalkenyl; alkenyltricycloalkyl; alkenyltricycloalkenyl; alkyltricycloalkyl; alkyltricycloalkyl. Optionally substituted (such as methyl, hydroxyl, thiol, carboxylate, aldehyde, heteroatom, and so on) tetracycloalkyl; benzotetracycloalkyl; alkylbenzotetracycloalkyl; hetero substituted alkylbenzotetracycloalkyl; alkylbenzotetracycloalkenyl; heterobenzotetracycloalkenyl; alkyltetracycloalkyl; alkyltetracycloalkenyl; alkenyltetracycloalkyl; alkenyltetracycloalkenyl; alkyltetracycloalkyl; alkyltetracycloalkyl.

Optionally substituted (such as methyl, hydroxyl, thiol, carboxylate, aldehyde, heteroatom, and so on) bi-, tri-, tetra- and poly(heterocycloalkyl); alkyl bi-, tri-, tetra-, and poly(heterocycloalkyl); E or Z alkenyl bi-, tri-, tetra- and poly(heterocycloalkyl); polycycloalkyl; benzopolycycloalkyl; alkylbenzopolycycloalkyl; hetero substituted alkylbenzopolycycloalkyl; alkylbenzopolycycloalkenyl; heterobenzopolycycloalkenyl; alkylpolycycloalkyl; alkylpolycycloalkenyl; alkenylpolycycloalkyl; alkenylpolycycloalkenyl; alkylpolycycloalkyl; alkylpolycycloalkyl; alkylpolycycloalkyl.

Optionally substituted (such as methyl, hydroxyl, thiol, carboxylate, aldehyde, heteroatom, and so on) aryl; alkylaryl; heteroaryl; alkylheteroaryl; ring-fused heteroaryls; alkyl substituted ring-fused heteroaryls; $R_6NH$, $R_6R_7N$, $R_8S$, $R_8SO$, $R_8SO_2$, $R_8SO_2NH$, $R_8SO_2NR_9$, $R_{10}CO$, $R_{10}OCO$, $R_{10}NHCO$, $R_{10}R_{11}NCO$, $R_{12}O$, $R_{13}SCO$, $R_{14}NCONHR_{15}$, $R_8NHSO_2NH$, $R_8NHSO_2NR_9$, $R_{10}NHCO$, $R_{10}OCONR_{16}$, $R_{10}NHCO$, $R_{10}R_{11}NCO$, $R_{13}SCONR_{17}$.

A=O, S.

W=, NH, $NR^1$, S, —S—S—, R or S or racemic —S(lone pair)O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

G=O, NH, $NR^1$, S, —S—S—, R or S or racemic —S(lone pair)O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

E=O, NH, $NR^1$, S, —S—S—, R or S or racemic —S(lone pair)O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—;

J=O, NH, $NR^1$ (e.g. N-Me), S, —S—S—, R or S or racemic —S(lone pair)O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—

X=H, halogen, $OR^1$, O, NH, $NR^1$, S, —S—S—, R or S or racemic —S(lone pair)O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—, with X attached either meta or para.

Y=H, O, $OR^1$, NH, $NR^1$, S, —S—S—, R or S or racemic —S(lone pair)=O—, —$SO_2$—, —SONH—, —NHSO—, —$NR^1$SO—, —$SONR^1$—, —$SO_2NH$—, —$NHSO_2$—, —$NR^1SO_2$—; —$SO_2NR^1$—, —$SO_3$— (sulfonate), C=O, —NHNH—, —N=N—, —NHO—, —ONH—; —$ONR^1$; $NR^1O$—, E or Z —CH=CH—; —C≡C—; $CH_2$; —C=N—, with Y attached either meta or para.

U=CH, N,N-oxide; where the point of attachment of Y and X are usually via carbon atoms in the central ring. When X=OH and U=N, a 2- or 4-pyridinol may be indicated, which automatically includes the keto-tautomers, the 2- and 4-pyridones. The side chain ($Y_p$) can be attached via the pyridone N, or at one of the remaining positions. Also, the ring can be benzenoid or pyridinoid, where benzenoid is preferred.

Z=$CO_2R^1$; R or S or racemic 5-substituted-thiazolidine-2,4-dione; R or S or racemic 3-substituted-pyrrolidine-2,5-dione; all diastereomers of 3,4-disubstituted-pyrrolidine-2,5-dione; R or S or racemic 4-substituted-azetidine-2-one; R or S or racemic 3-substituted-azetidine-2-one; all diastereomers of 3,4-disubstituted-azetidine-2-one; 3-substituted-azetidine-2,4-dione; 1-substituted-1,3-diazetidine-2,4-dione; 1-substituted-1,3-diazetidine-2-one; all diastereomers of 1,4-disubstituted-1,3-diazetidine-2-one; 5-substituted-2,4-dihydro-[1,2,4]triazol-3-one; 4-hydroxy-5-substituted-1,2-dihydro-pyrazol-3-one; 4-alkoxy-5-substituted-1,2-dihydro-pyrazol-3-one; 4-alkoxy-substituted-1,2-dihydro-pyrazol-3-one; 5-substituted-2H-pyrazole-3,4-dione; 5-substituted-imidazole-2,4-dione; 3-substituted-pyrrole-2,5-dione; 3-Hydroxy-4-substituted-pyrrole-2,5-dione; 3-alkoxy-4-substituted-pyrrole-2,5-dione; 3-alkoxy-substituted-pyrrole-2,5-dione; 5-substituted-oxazolidine-2,4-dione; 5-substituted-imidazolidine-2,4-dione; 5-substituted-1,2-dihydro-pyrazol-3-one; 5-substituted-2H-tetrazole; 4-substituted-2H-[1,2,3]triazole; 3-substituted-1H-[1,2,4]triazole; R or S or racemic 5-substituted-3,5-dihydro-[1,2,3]triazol-4-one; 5-substituted-2,3-dihydro-[1,2,3]triazol-4-one; R or S or racemic 4-substituted-pyrazolidine-3,5-dione; 4-substituted-[1,2,4]triazolidine-3,5-dione.

Also, all benzo-fused examples of the above monocycles such as, but not limited to: 2, 3, 4 or 5-substituted-isoindole-1,3-dione; 3, 4 or 5-substituted-1,2-dihydro-indazol-3-one; 3, 4 or 5-substituted-2H-benzotriazole, and so on.

In one embodiment the compound is BP-104:

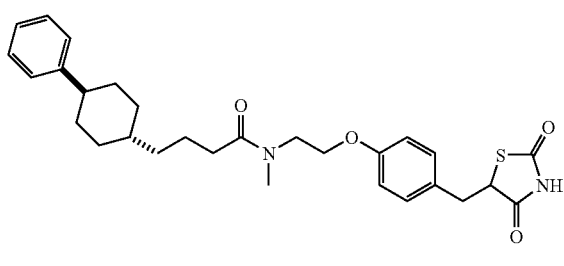

In another embodiment the compound is BP-105

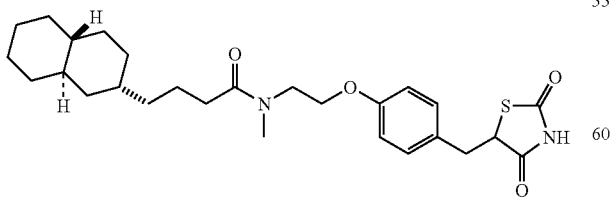

In another embodiment the compound is 5-adamantan-2-yl-pentanoic acid {2-[4-(2,4-dioxo-thiazolidin-5-yl-methyl)-phenoxy]-ethyl}-methyl-amide (BP-107):

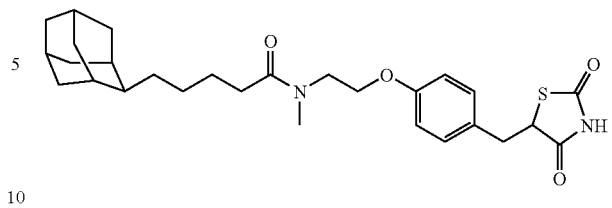

Schemes for Preparation of Compounds of the Disclosed Formulas

In view of the foregoing schemes, the disclosure herein, and knowledge in the art, the synthesis of the compounds of the invention described herein is possible by one skilled in the art of organic synthesis. Techniques available in the art are described, for example, in J. A. Joule and K. Mills "Heterocyclic Chemistry", Fourth Edition, Blackwell Science, Oxford. (2000), pp. 1-589; Gilchrist, T. L. "Heterocyclic Chemistry" 3$^{rd}$ Ed., Longman, Essex (England), 1997, pp. 1-414 pgs; "The Chemistry of Heterocyclic Compounds", Vols. 1-58, John Wiley & Sons, N.Y. 1950-1984 (Weissberger, A., Editor); 1985-current (E. C. Taylor, Ed.).

For the formulas noted, examples of starting materials that are either commercially available or have been constructed in the literature for preparing specific embodiments are provided by CAS registry number as shown below.

Formula 1, 6

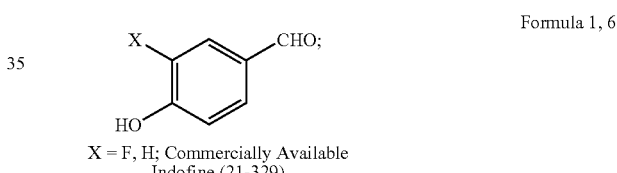

X = F, H; Commercially Available
Indofine (21-329)

Formula 2

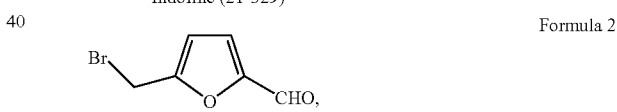

Commercially Available

Formula 3

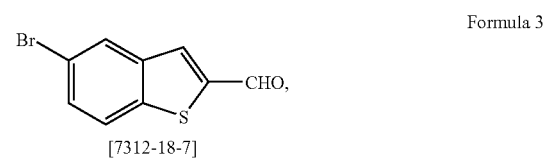

[7312-18-7]

Formula 4

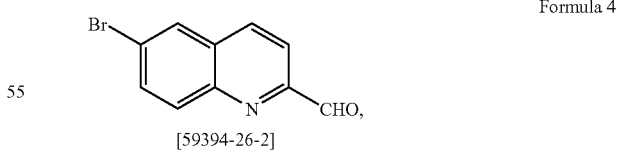

[59394-26-2]

Formula 7

commerically available

-continued

Formula 8

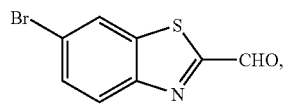
[53218-26-1]

Formula 9

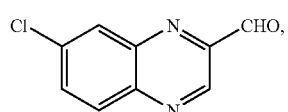
[1770-42-9]

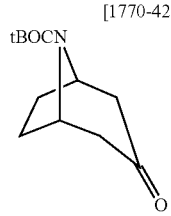
Fluka
(15515)

The synthetic preparation of examples for Case 1 is presented in the following Schemes. In these cases, substituted acids are required for coupling with appropriate amines to obtain required targets. Some representative acids are shown in Scheme 1, such as the cycloalkyl-alkyl acids 1-5; the aryl-alkyl acids 6-11; and the heteroaryl-alkyl acids 6 h-11 h. The acids are selected from Scheme 1 but are not restricted by the Scheme. For example, a quinolinylalkyl acid is representative of a benzo fused-heteroaryl alkyl acid. On the other hand, heterocycloalkyl R groups are represented by piperidinyl or piperazinyl moieties, or any other optionally substituted heterocyclic ring system such as those containing O, N and/or S, SO, SONH, $SO_2NH$, or $SO_2$. The acids 1-11 and 6 h-11 h are available commercially or can be prepared by known methods.

---

Scheme 1

R—$(CH_2)_n$—COOH
1, cyclohexyl hexanoic acid, n = 5
2, cyclopentyl hexanoic acid, n = 4
3, cyclopropyl hexanoic acid, n = 3
4, cyclohexyl pentanoic acid, n = 4
5, cyclopentyl pentanoic acid, n = 4
5a, Trans-4-phenylcyclohexyl butanoic acid, m = 4, n = 3
5b, Trans-4-(p-Chlorophenyl)cyclohexyl butanoic acid, m = 4, n = 3
5c, 4-(Decahydronaphthalen-2-yl)-butyric acid
5d, 4-Adamantan-2-yl-butyric acid
5e, 4-Adamantan-2-yl-pentanoic acid
5f, 5-(8-Aza-bicyclo[3.2.1]oct-3-yl)-pentanoic acid
5g, 5-N-tBOC-5-N-Methylamino pentanoic acid
5h, 5-(p-Chlorophenyl) pentanoic acid, m '2 4, n = 3

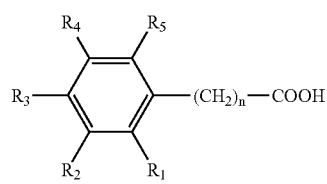

6, 5-Phenylvaleric acid, $R_1 = R_2 = R_3 = R_4 = R_5$ = H, n = 4
7, 4-phenylbutyric acid, $R_1 = R_2 = R_3 = R_4 = R_5$ = H, n = 3
7a, 4-(p-Cl-phenyl)butyric acid, $R_1 = R_2 = R_4 = R_5$ = H, $R_3$ = Cl, n = 3

---

-continued

Scheme 1

8, 3-Phenylpropionic acid, $R_1 = R_2 = R_3 = R_4 = R_5$ = H, n = 2
9, 5-Phenylacetic acid, $R_1 = R_2 = R_3 = R_4 = R_5$ = H, n = 1
10, 3-(3,4-dimethoxyphenyl)propionic acid, $R_1, R_4, R_5$ = H, $R_2 = R_3$ = OMe, n = 2
11, 3-(3,4-dimethoxyphenyl)acetic acid, $R_1, R_4, R_5$ = H, $R_2 = R_3$ = OMe, n = 1
R—X—$(CH_2)_n$—COOH
11a, 8-Acetylsulfanyl-octanoic acid; n = 7, X = S, R = $COCH_3$.
11b, 5-(tert-Butoxycarbonyl-methyl-amino)-pentanoic acid, n = 4, X = NHMe, R = tert-BOC

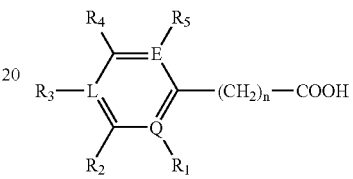

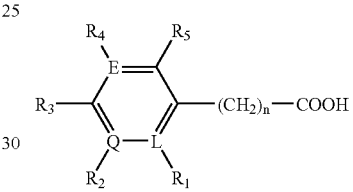

6h, 5-(2-pyridyl)valeric acid, $R_1$ = lp; $R_2 = R_3 = R_4 = R_5$ = H; Q = N; L, E = C, n = 4
7h, 4-(2-pyridinyl)butyric acid, $R_1, R_5$ = lp; $R_2 = R_3 = R_4$ = H; Q, E = N; L = C; n = 3
8h, 3-(3-pyrimidinyl)propionic acid, $R_1, R_3$ = lp; $R_2 = R_4 = R_5$ = H, Q, L = N, E = C, n = 2
9h, 2-(4-pyridyl)acetic acid, $R_1 = R_2 = R_3 = R_5$ = H, $R_4$ = lp; L = N; Q, E = C; n = 1
10h, 2-(3,4-dimethoxypyridyl)propionic acid, $R_1$ = lp; $R_5$ = H, $R_3 = R_4$ = OMe, Q = N; E, L = C; n = 2
11h, 2-(4,5-dimethoxypyrimidinyl)acetic acid, $R_1 = R_5$ lp; $R_4$ = H, $R_3 = R_4$ = OMe, Q, E = N; L = C; n = 1

(lp = lone pair of electrons)

As examples, the synthesis of compounds 17, 18, and 20 is shown (Scheme 3) in which, as Case 1, the following conditions apply: R=cyclopentyl; u, r, c, b, e, f, s, i and k=0; A, Y═O (at para position); h, q, m, n, o and p=1; $R_2, R_3, R_6, R_7, R_{10}, R_{11}$, X, =H; a=4; J=N, $R_1$═$CH_3$ and M═CH; □; d=2; L, Q, U, V, and Z═$CO_2CH_2CH_3$ (17); Z═$CO_2H$ (18); or Z═thiazolidine-2,4-dione (20).

Scheme 2

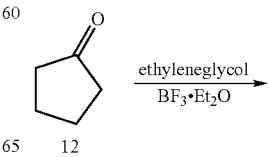

12

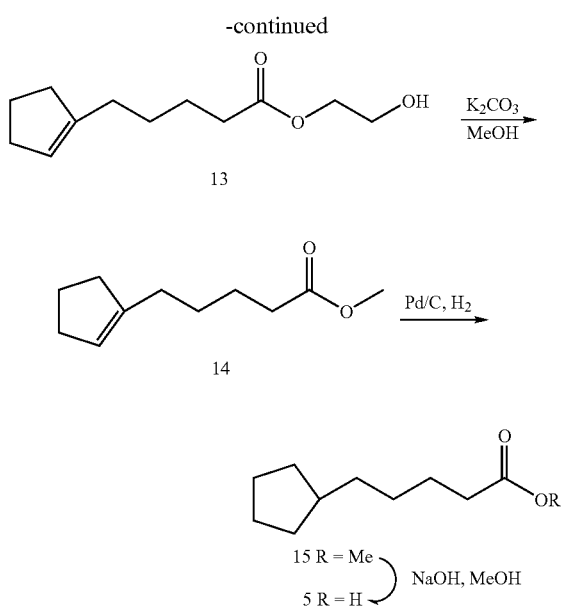

A precursor for Scheme 3,5-(Cyclopentyl)pentanoic acid 5, is prepared by employing a modified procedure to the one reported (Nagurnao, et al. *Tetrahedron* 49 (46), 1993, 10501-10510) starting from cyclopentanone 12 as shown in Scheme 2. Self-condensation of cyclopentanone 12 in the presence of ethylene glycol and boron trifluoride-etherate furnishes the hydroxy ethyl ester 13. Transesterification with methanol and potassium carbonate converts 13 into the methyl ester 14. Catalytic hydrogenation reduces the double bond to give methyl 5-(cyclopentyl)pentanoate 15. Ester hydrolysis of 15 occurs readily using sodium hydroxide to give the desired acid 5.

With the requisite acid(s) in hand, amide formation with the appropriate amines furnishes the desired targets. Linking the amine 16 with the acid 5 occurs under activation of the carboxylic acid with dicyclohexylcarbodiimide (DCC) to give the desired target 17 as shown in Scheme 3.

Other common methods of carboxylate activation such as by conversion to the acid chloride, N-hydroxysuccinamide/DCC, N-hydroxybenzotriazole/diisopropylcarbodiimide, etc. can be employed as well for these couplings. Hydrolysis of the ester 17, a prodrug of the bioactivated free acid, provides carboxylic acid 18. Alternatively, coupling of the known amino-thiazolidinedione 19 with acid 5 leads to the production of the cyclopentyl terminated thiazolidinedione 20.

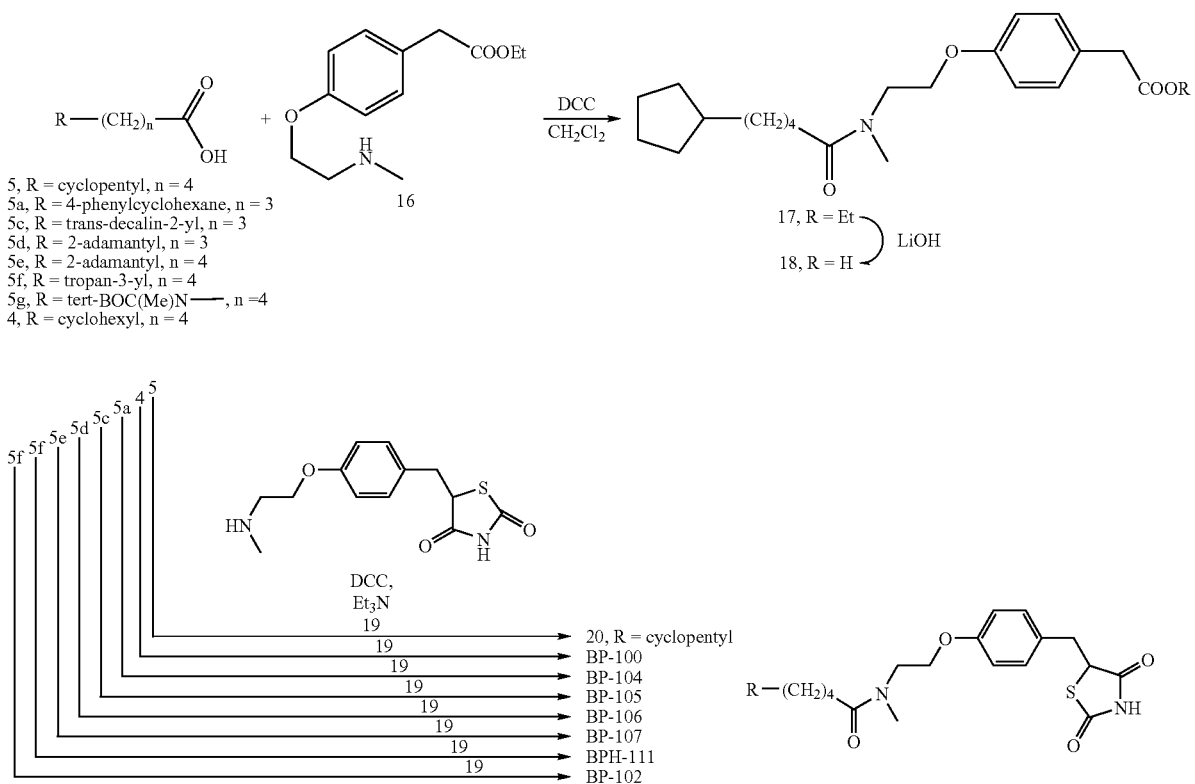

In Case 1, when R=cyclopentyl; u, r, c, b, e, f, s, i and k=0; A, Y=0 (at para position); h, q, m, n, o and p=1; $R_2$, $R_3$, $R_6$, $R_7$, $R_{10}$, $R_{11}$; a=4; J=N, $R_1$=CH$_3$; L, Q, U, V, and M=CH; and Z=CO$_2$CH$_2$CH$_3$, d=3 and X=m-Cl, the ethyl ester 25 is obtained (Scheme 4). Hydrolysis of this ester gives the carboxylic acid 26. The homologated precursor, amine (Berger, et al, *J. Biol, Chem,* 1999. 274: p. 6718-6725) 21, which is one carbon atom longer than 19, is prepared as shown in Scheme 4.

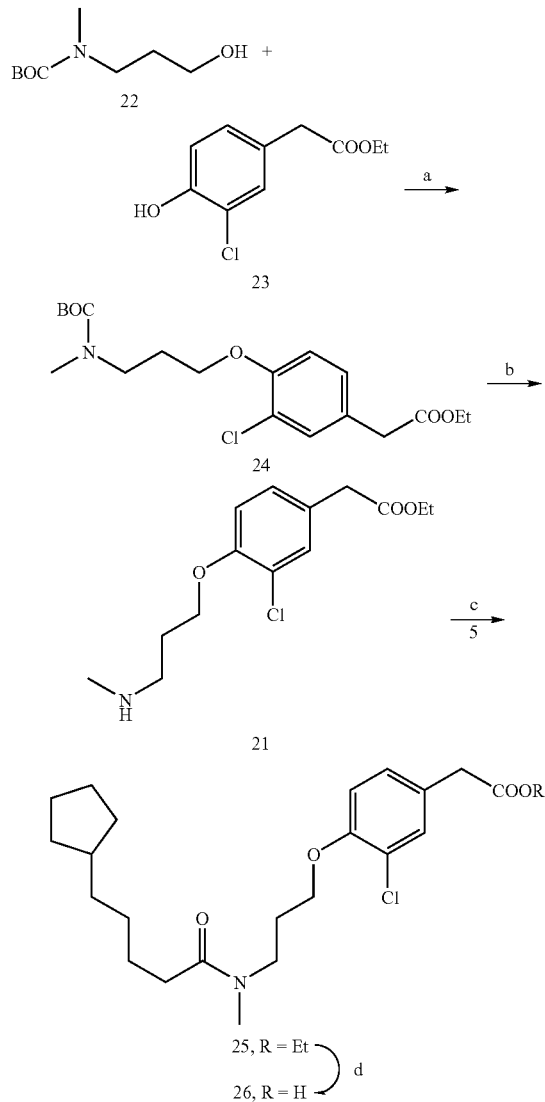

Key: a) 22, MsCl, Pyridine and then (23 + NaH); b) HCl, dioxane; c) DCC, dichloromethane, triethylamine and 5; then add 21; and d) NaOH, MeOH, water.

The phenol 23 is coupled with the t-BOC alcohol 22 via its mesylate to furnish the t-BOC protected amine 24. The t-BOC-protecting group is removed by acid treatment to furnish the desired amine 21. As in other cases, the final acid coupling occurs readily to afford the target amide 25. Hydrolysis of 25 smoothly furnishes the acid 26.

A similar strategy may be employed to prepare targets from Case 1, where (Y)$_p$ is oriented meta and X=para-methoxy as shown in Scheme 5. The alcohol 22 is coupled with ethyl homovanillate 27 to give the meta oriented t-BOC compound 28.

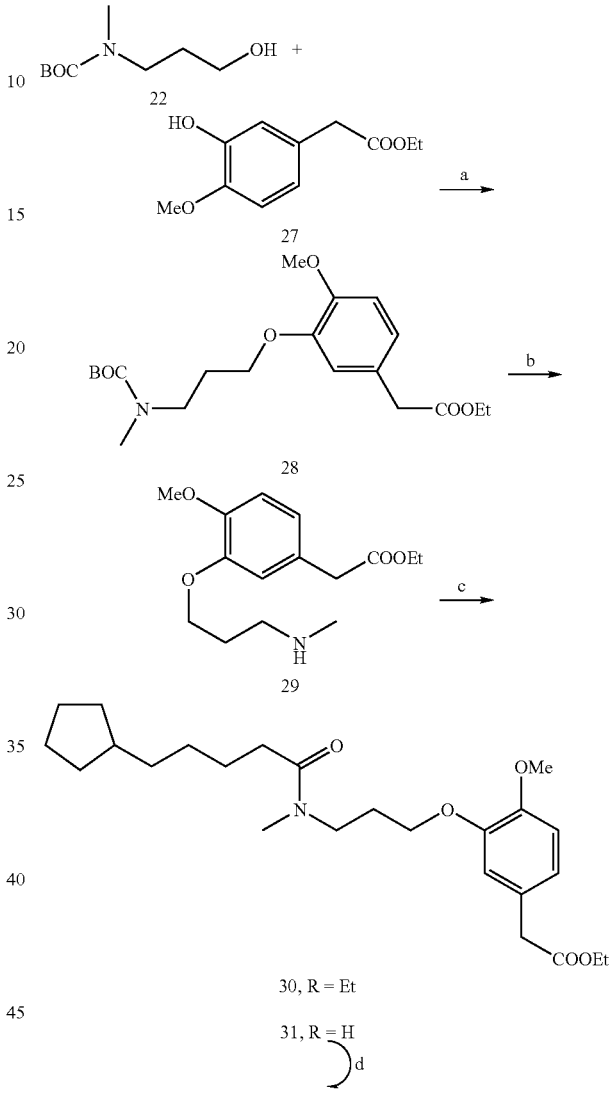

Key: a) 22, MsCl, Pyridine and then (27 + NaH); b) HCl, dioxane; c) DCC, dichloromethane, triethylamine and 5; then add 21; and d) NaOH, MeOH, water.

Deprotection of the t-BOC group furnishes the desired amine 29, which is coupled with acid 5 (or other examples, e.g. 1-11, 6 h-11 h) to give ethyl ester 30. Hydrolysis, as before, gives the acid 31. For targets as in Case 1, where Z is thiazolidinedione, a slightly different strategy is employed as depicted in Scheme 6. Isovanillin 32 is first coupled with t-BOC alcohol 22 via the mesylate to finish the aldehyde 33. The aldehyde 33 thus formed is then condensed with thiazolidinedione (Bernhard, et al. *J. Med. Chem.* 35, 1992, 1853-1864; Clark, et al. *J. Med. Chem.* 34, 1991, 319-325), to provide the adduct 34, which is reduced using sodium dithionite to give the desired TZD compound 35. Deprotection of the T-BOC group gives the amine 36, which is coupled with desired acids (e.g. 1-11, 6 h-11 h), which in Scheme 6 was phenylvaleric acid 6.

23

Scheme 6

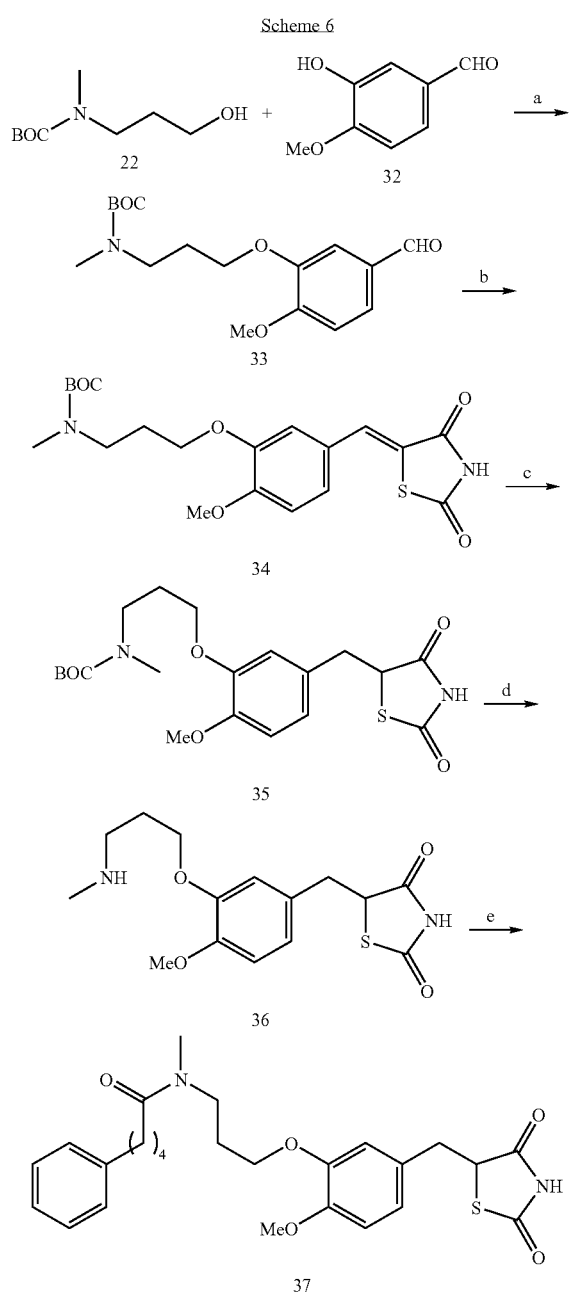

Key: a) 22, MsCl, pyridine and then (32 + NaH); b) 2,4-Thiazolidinedione, NaOAc, AcOH; c) Sodium dithionite; d) HCl, dioxane; and e) DCC, dichloromethane, triethylamine and 6; then add 36.

In certain instances a totally different approach needs to be employed to prepare these targets as represented in Scheme 7.

Scheme 7

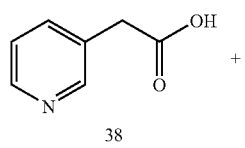

24

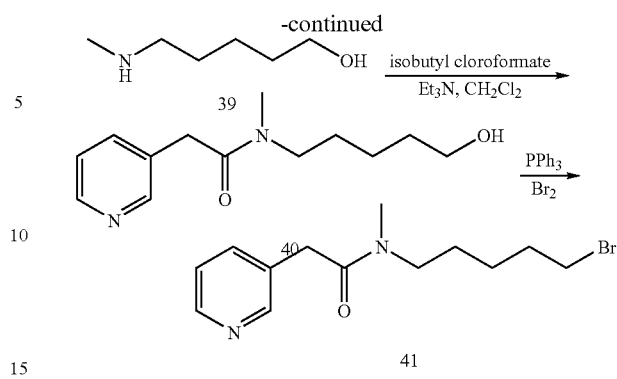

The acid 38 is first coupled with the amino alcohol 39 via the mixed anhydride prepared in situ using isobutyl chloroformate and triethylamine. The resulting alcohol 40 is then converted to the bromide 41 using bromine and triphenylphosphine. Wagner, et al. *J. Chem. Soc. Chem. Comm.* 1989, 1619. With the bromo compound 41 in hand, coupling to the phenols 34-39 corresponding to the different structural classes via the phenoxides provides the desired targets.

Scheme 8

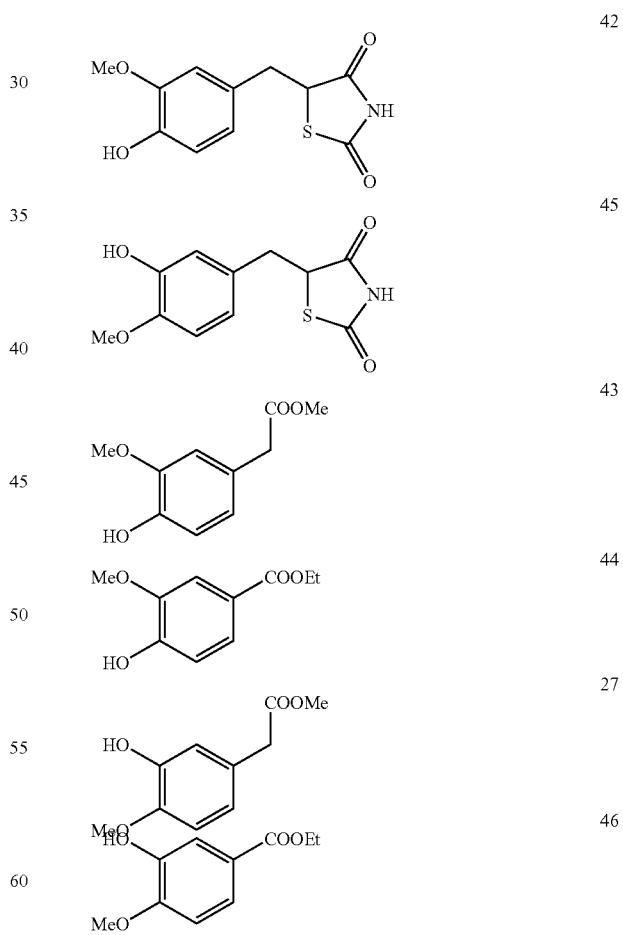

For those targets as in Case 1, where p=0 a different strategy is employed, as described in Scheme 9. The phenol 45 is converted to the triflate 47 by treating it with PhNTf$_2$ in the presence of DMAP.

The triflate 47 is then coupled with the iodocompound 51 (Piber, et al. *Org. Lett.* 1999, 1323-1326), which is prepared from its alcohol 50 by treating with iodine and triphenylphosphine, to give the t-BOC compound 48. The t-BOC group is removed in the presence of acid to give the free amine 49 which is coupled with the acids 1-11, 6 h-11 h to arrive at the targets as shown in Scheme 9.

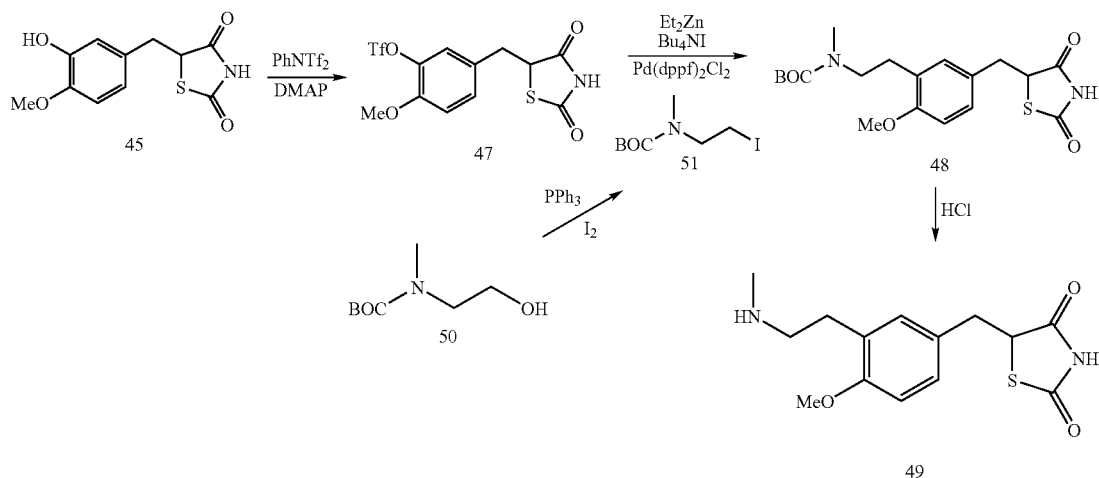

Cinnamates such as 55-58 (Scheme 11) are excellent stereoelectronic mimetics for the corresponding thiazolidine-2,4-diones (e.g. 56 vs. 20). An overlay of 20 with 56 (FIG. 1) shows near perfect alignment of the acidic protons, the aryl rings, and the terminal cyclopentyl rings. These same space-filling and hydrogen bonding capabilities are confirmed in docking studies with PPAR-γ.

A prodrug of the carboxyl group is a logical necessity for optimization of oral or topical bioavailability, such as, but not limited to, the simple ethyl ester 55. Synthesis of 55 and 56 follow from previous schemes, and are shown in Schemes 10 and 11. The first step is to prepare the cinnamyl amine (54, Scheme 10) followed by coupling to a carboxylic acid. In Scheme 11, the cyclopentyl (55, 56) and phenyl (57, 58) R groups were arbitrarily selected as examples of the method.

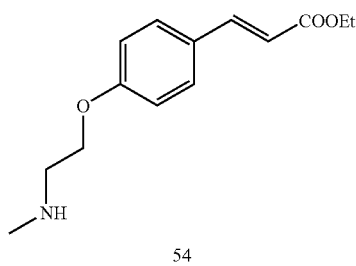

Key: a) 22, MsCl, pyridine and then (52 + NaH); b) HCl, dioxane.

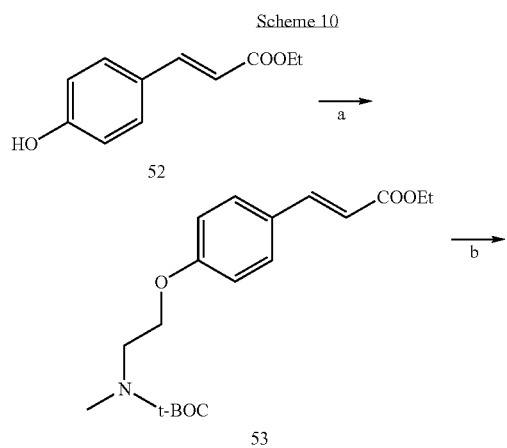

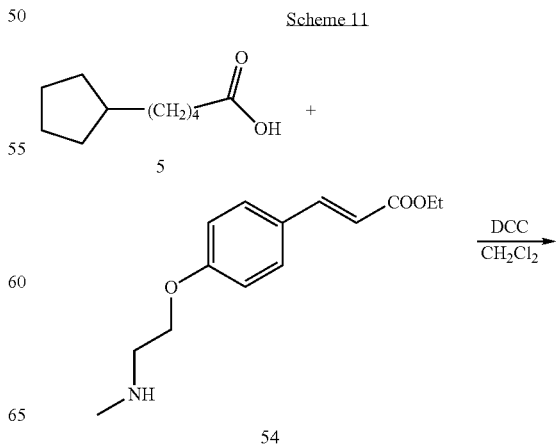

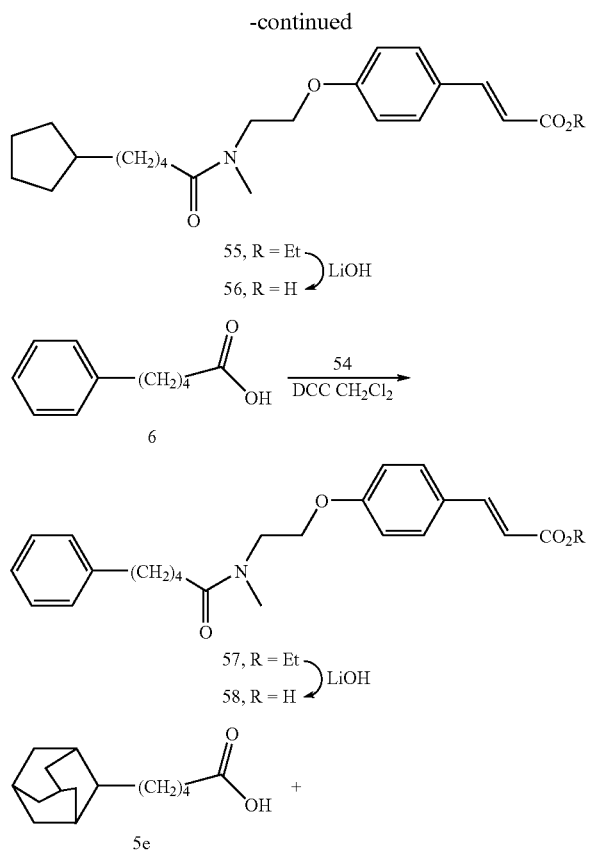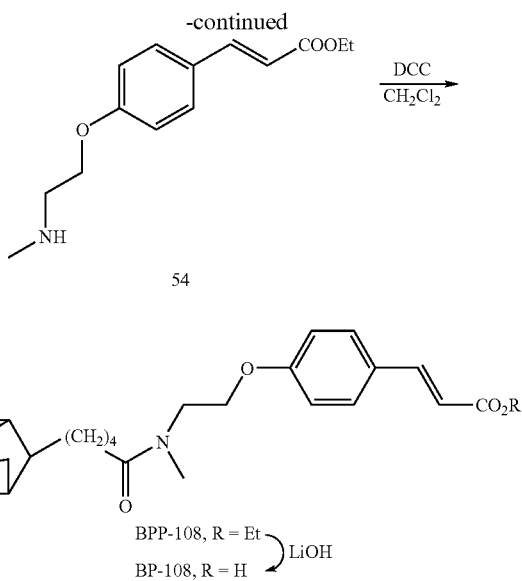

In addition to benzoic acids, arylacetic acids, aryloxyacetic acids, cinnamic acids, and 5-thiazolidine-2,4-diones (TZD), many other acidic moieties can substitute successfully for the TZD "head group" of PPAR-α, γ and/or δ ligands. A limited set of examples of heterocyclic "head groups" that can substitute for the TZD moiety is shown in FIG. 2. For example, the succinamide analog 64, a 3-substituted pyrrolidine-2,5-dione in which X=CH$_2$, could be prepared as shown in Scheme 13.

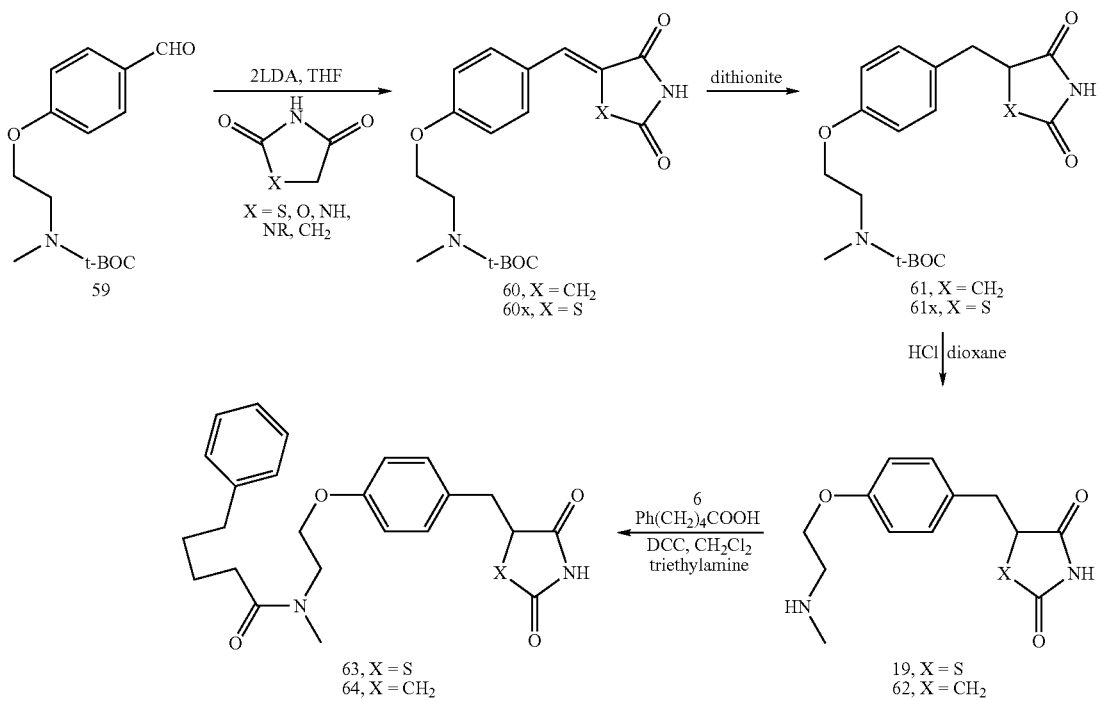

Alternatively, when X=S, the thiazolidinedione 63 is afforded. Using the known t-BOC protected benzyaldehyde-amine 59 for Aldol condensation with succinamide furnishes the conjugated benzylidenylsuccinamide 60, or TZD analog, 60x. Reduction, as with the TZD analog, occurs with dithionite to give either 61x (X=S), or alternatively, occurs readily with hydrogenation conditions (H$_2$/Pd—C), or even dissolving metal (Al—Hg amalgam, wet THF) when X=CH$_2$, to give 61. Now, as before, t-BOC deprotection with anhydrous HCl in dioxane affords 62, and finally, coupling of the amine with whatever carboxylic acid is desired, in this case 6 is selected, to provide targets 63 or 64. Obvious extensions of the chemistry presented to this point are to include heteroatoms via the azine and dizaine classes, and to prepare the corresponding carboxylic acids for coupling with 19 or 62 as before in Scheme 13.

While many other possibilities exist, the synthesis of 65 as in Scheme 14 is instructive for the entire class, essentially, and is based on the availability of the corresponding azine aldehyde. The route to interconvert the aryl aldehyde to the saturated acid is simply to conduct a crotonic phosphonate derived Horner Emmons condensation to homologate the aldehydes up to the corresponding pentadieneoic acids as shown in Scheme 15.

The 2H-tetrazole ring is a good isoelectronic replacement for a carboxylic acid or TZD group. As shown in Scheme 16, the tetrazole variant 81 is readily prepared from the corresponding nitrile 78 upon treatment with azide ion, followed by t-BOC deprotection and coupling to the pyridyl acid 80.

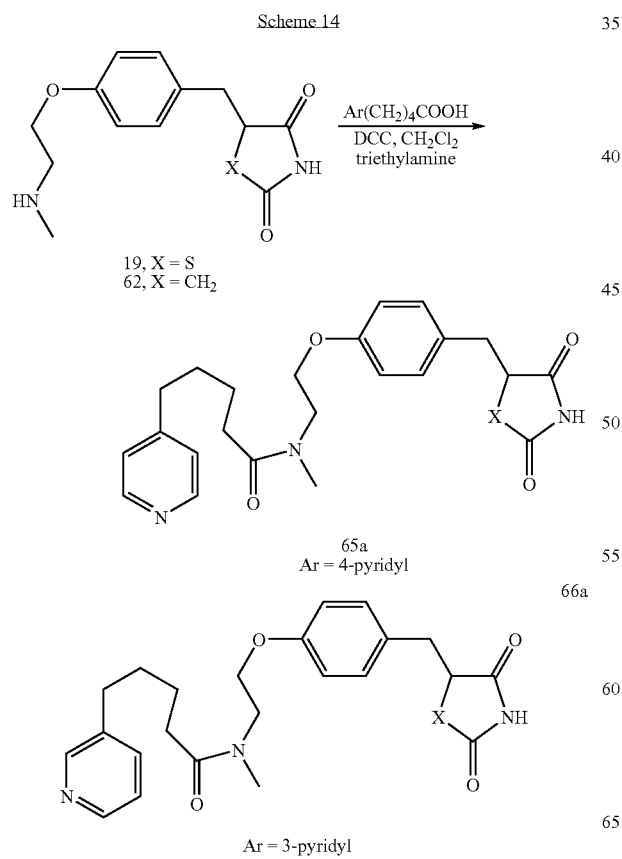

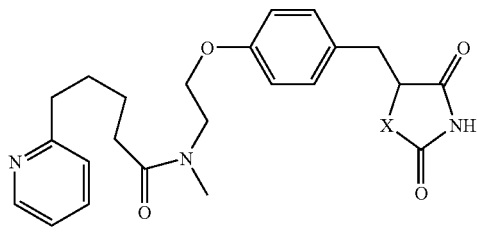

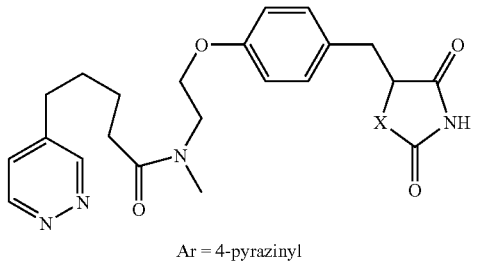

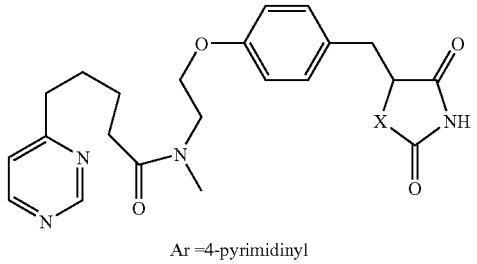

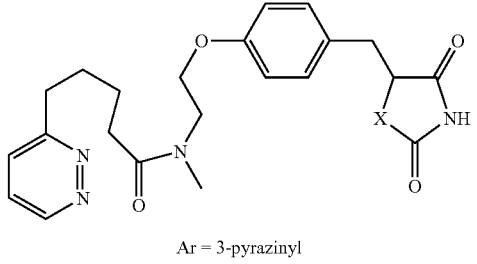

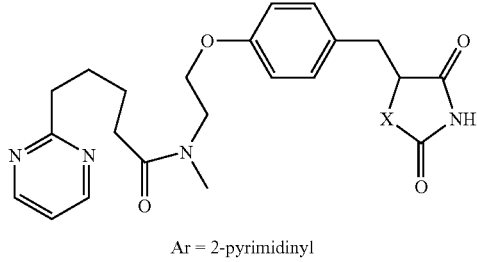

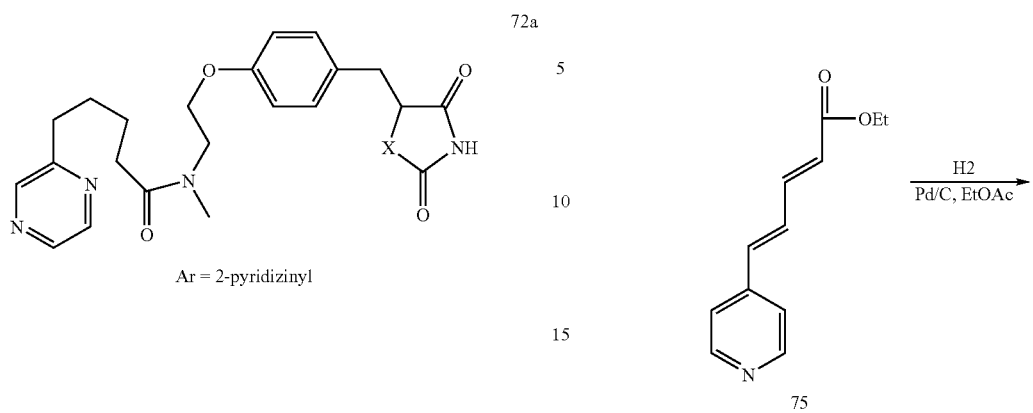
Scheme 15
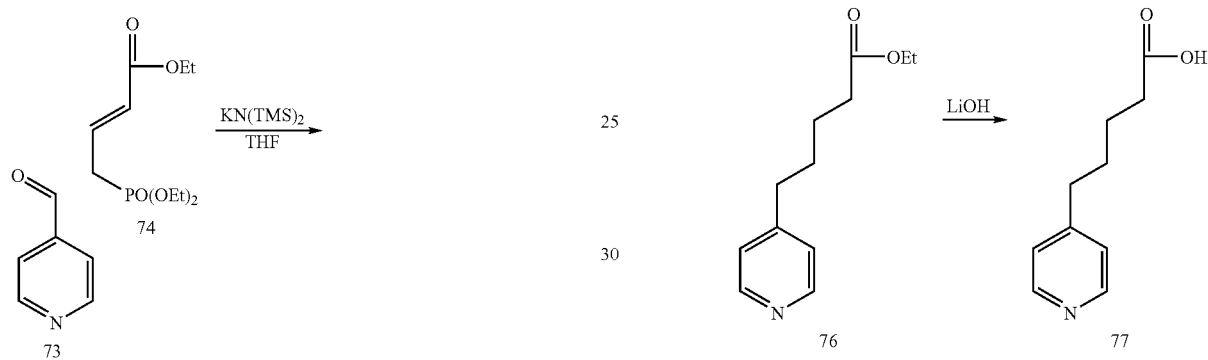
Scheme 16
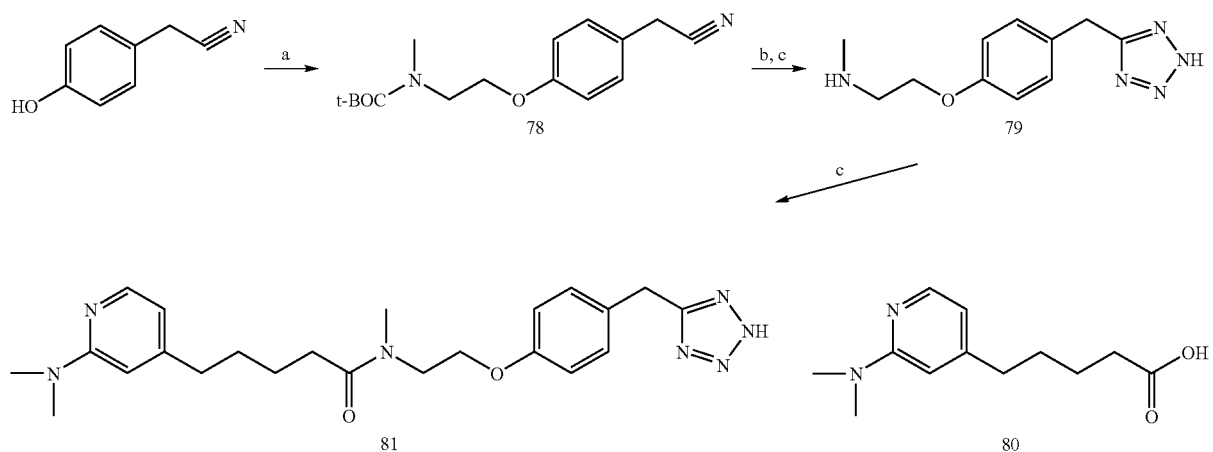
Key: a) 22, MsCl, pyridine, CH₂Cl₂; then [(p-hydroxyphenyl)acetonitrile + NaH]; b) NaN₃, DMF; c) HCl, dioxane; d) DCC, then 79.

Other non-limiting examples of possible Z groups is provided by the 5-substituted 1,2-dihydropyrazol-3-one 69, the 4-substituted 1,2-dihydropyrazol-3-one 70, the 4-substituted pyrazolidine-3,5-dione 71, or the β-lactam derivative, a potentially subversive substrate, shown in FIG. 3.

The synthesis of the cyclohexylphenyl derivative BPH-109 is readily accomplished (Scheme 17) by chiral alkylation of an O-Ethyl glycolamide 84 and the BOC protected benzylic chloride 83. After workup and loss of the TMS group, the phenol is replaced by a Mitsunobu reaction to afford the BOC amide 83 tig reaction, after mild acid hydrolysis, the pseudoequatorial aldehyde 89 is obtained. Now, Horner Emmons reaction with methyl g-diethylphosphonocrotonate, NaH and tropinal 89 fimnishes the diene-ester 90. Catalytic hydrogenation followed by base hydrolysis furnishes the acid 91. Simple active-ester coupling of 91 with the furane amine 92 gives the penultimate intermediate 93. Dilute HCl in dioxane provides the product BP-110.

Synthesis of the tropane containing ring system requires preparation of the acid 91 from the ketone 88. We have used this sequence of operations before, employing any one of a

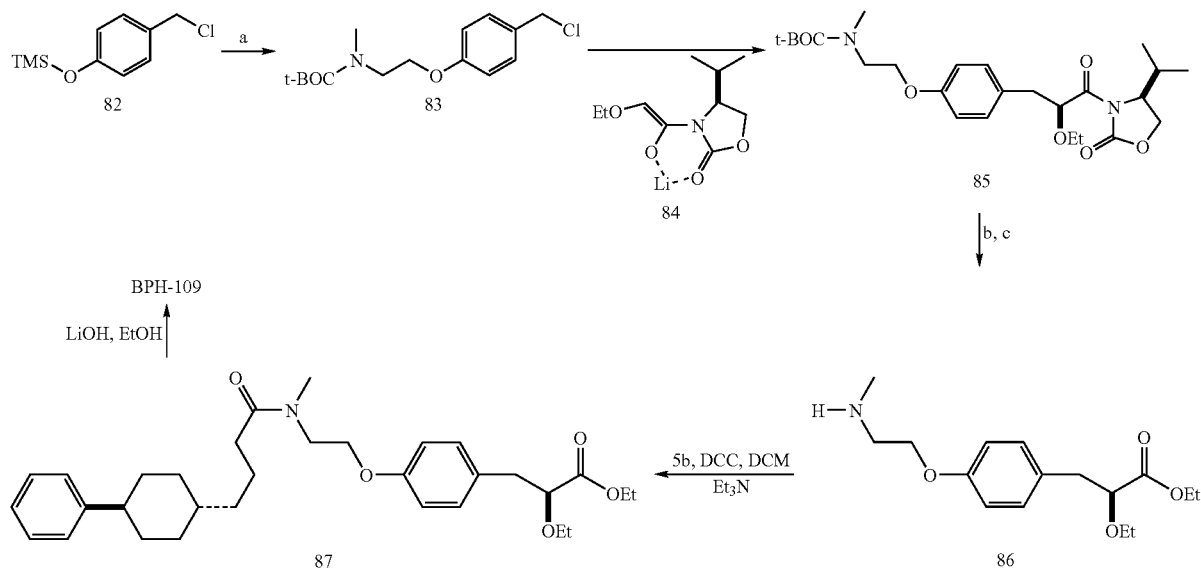

Alkylation of the O-ethylglycolamide of oxazolidindione prepared from either R or S valinol could give either R or S a-ethoxypropionic acid in the final step. In any even, the BOC group is removed with TFA and the free amine is coupled with the acid 5b to afford the prodrug form of target BPH-109.

The Tropinone BPH-110 can be prepared from commercially available N—BOC tropin-3-one by the sequence outlined in Scheme 18. The ketone is first homologated to the aldehyde by a simple methoxymethylphosphorane Witnumber of one carbon ketone to aldehyde homologations. The most well known is the Wittig reaction of MeOCHLiP $(Ph_3)_3$ with 88, and the intermediate enol ether readily hydrolyzes in workup with dilute aq. acid to afford the pseudoequatorial aldehyde 89. Now, quite simply, $(EtO)_2POCH_2CH=CHCOOMe$ treated with NaH affords a Horner Emmons reagent that homogates the aldehyde 89 to the diene 90. Simple hydrogenation and ester hydrolysis then provides the required acid 91.

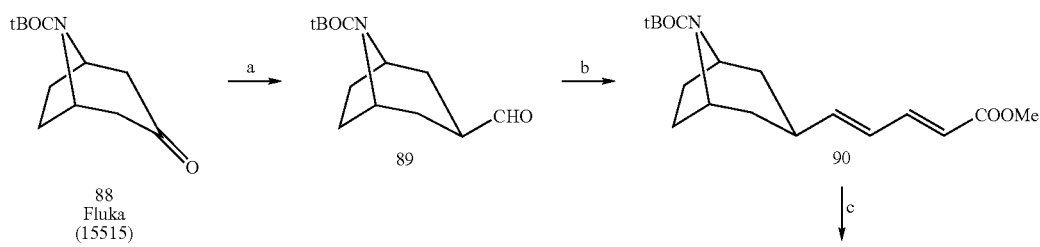

-continued

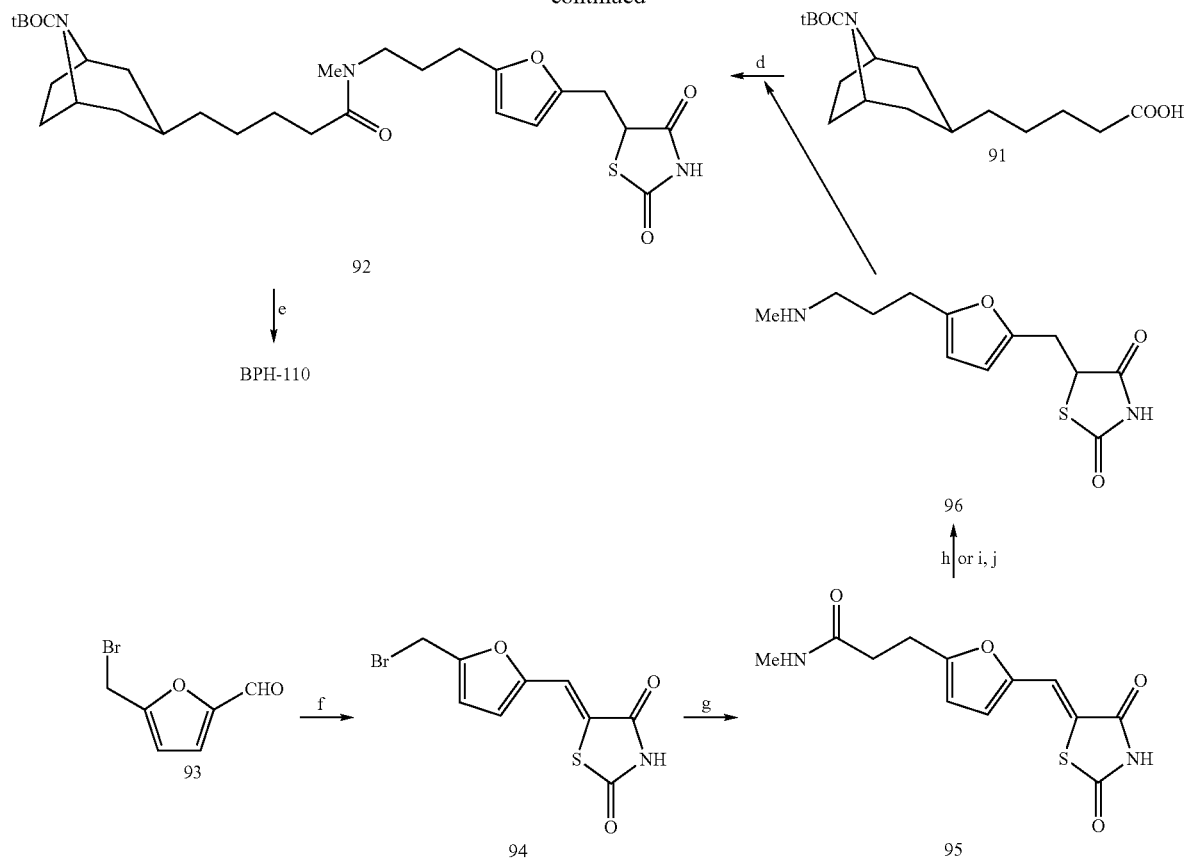

Key: a) MeOCHLi(PPh₃)₃, THF; aq. acid workup; b) (EtO)₂POCH₂CH=CHCOOMe, BuLi, THF; c) H₂, Pd/C, MeOH; then filter and add aq. NaOH; d) DCC; DCM, Et3N; e) HCl, dioxane; f) 1,3-thiazolidine-2,4-dione, NaH; -78° C. → room temperature; g) MeNHCOCH3, 2nBuLi, THF; 94; h) AlH₃, ether; or i) H₂, Pd/C, MeOH; j) NaH, then AlH₃, ether.

The other half of the target, BP-110, can be prepared from the commercially available furan 93 as shown in the Scheme. Some degree of chemoselectivity is required in the first aldol reaction, requiring low temperatures. Once the TZD ring is in place, the allylic bromide is readily displaced by the dianion of N-methylacetamide to afford 95. Now, reduction with AlH3 results in reduction of the double bond and the amide carbonyl. However, it may be necessary to carry this sequence out for better yields in a two step fashion. First, the TZD double bond is reduced by hydrogenation, and then, the TZD anion becomes unreactive towards deoxygenation whilst the amide O is readily removed to afford the requisite amine 96.

Scheme 19

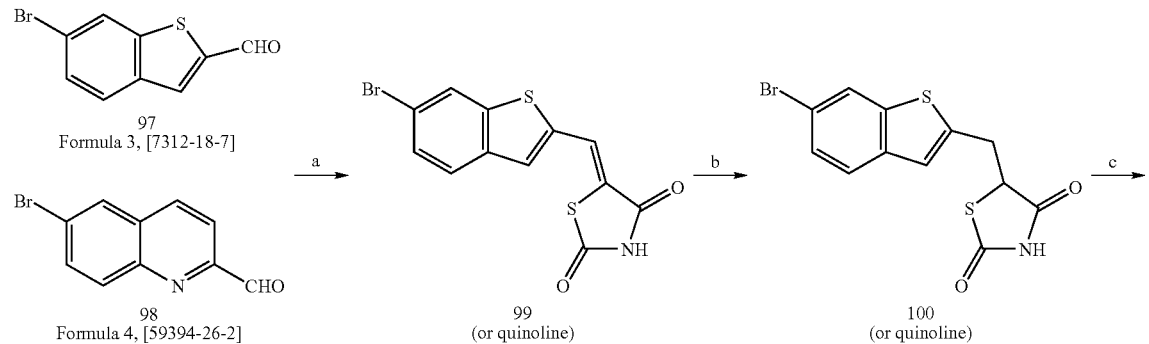

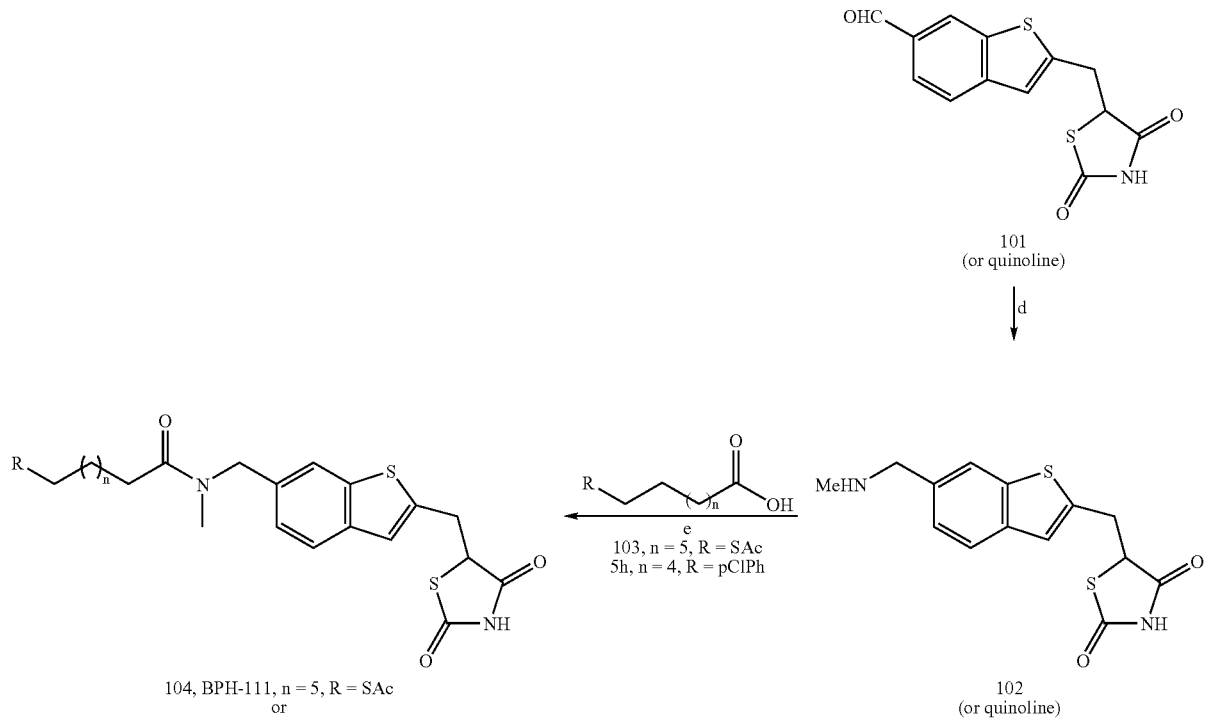

101
(or quinoline)

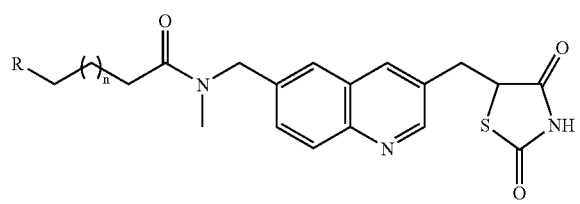

104, BPH-111, n = 5, R = SAc
or 103, n = 5, R = SAc
5h, n = 4, R = pClPh 102
(or quinoline)

105, BPH-112, n = 5, R = pClPh

Key: a) 1,3-thiazolidine-2,4-dione, 2NaH; -78° C. → room temperature, THF; b) Mg, MeOH; c) Pd(0), CO, HCO$_2$H, Et$_3$N; d) MeNH$_2$, NaCNBH$_3$, buffer, THF; e) 102, DCC, DCM; then 101, Et$_3$N.

As shown in Scheme 19, for BP-111 and 112, a common approach dictated largely by available starting materials is employed wherein either 97 or 98 (benzothiophenal, quinolinal, respectively) are condensed in the usual manner with thiazolidinedione and base (e.g. 2NaH) to afford the unsaturated aldol adduct 99 (or the corresponding quinoline adduct, not shown). Reduction of the unsaturated system can be conducted in a number of different ways, with sodium dithionite or with Mg metal in MeOH, to achieve chemoselectivity over the aryl bromide. With the benzylic TZDs in hand (e.g. 100 or the quinoline, not shown), the bromide can now be converted to the aldehyde under mild formylation conditions with Pd(0) and formic acid (base) furnishing 101 or its quinoline analog. Reductive amination is now possible under mild conditions with buffered sodium cyanoborohydride, or with Ti(iOPr)$_4$/NaBH4, to give the secondary amine 102 (or quinoline analog). Finally, coupling with the appropriate acid as usual (DCC, DCM, Et3N) gives the adducts 104 (BPH-111) or 105 (BPH-112).

The cinnamate BPH-113 (115) can be synthesized as shown in Scheme 20. Starting from biphenylcarboxaldehyde 106, a four carbon homologation is conducted via Horner Emmons reaction to afford the dienal 107, catalytic hydrogenation of which gives the aldehyde partner in an ensuing Horner Emmons reaction with 113. For synthesis of 113, commercially available 109 is converted to the ethyl cinnamate by routine Horner Emmons condensation to give 110. Then, alkylation with excess 1,3-dibromopropane gives rise to bromide 111. Now, Arbutzov reaction with triethylphosphite affords the phosphonate ester 112. In order to ensure a that a Z olefin is formed, the modification of the Horner Emmons reaction is employed in which the diethyl ester groups are replaced by trifluoroethanol moieties by simple exchange in excess trifluoroethanol. With olefin 114 in hand, a final chiral cyclopropanation can be conducted using Rh carbene complexes with chiral ligands on Rh. An example is provided by Kwong, Hoi-Lun, et. al *Tetrahedron: Asymmetry* (2001), 12(19), 2683-2694.

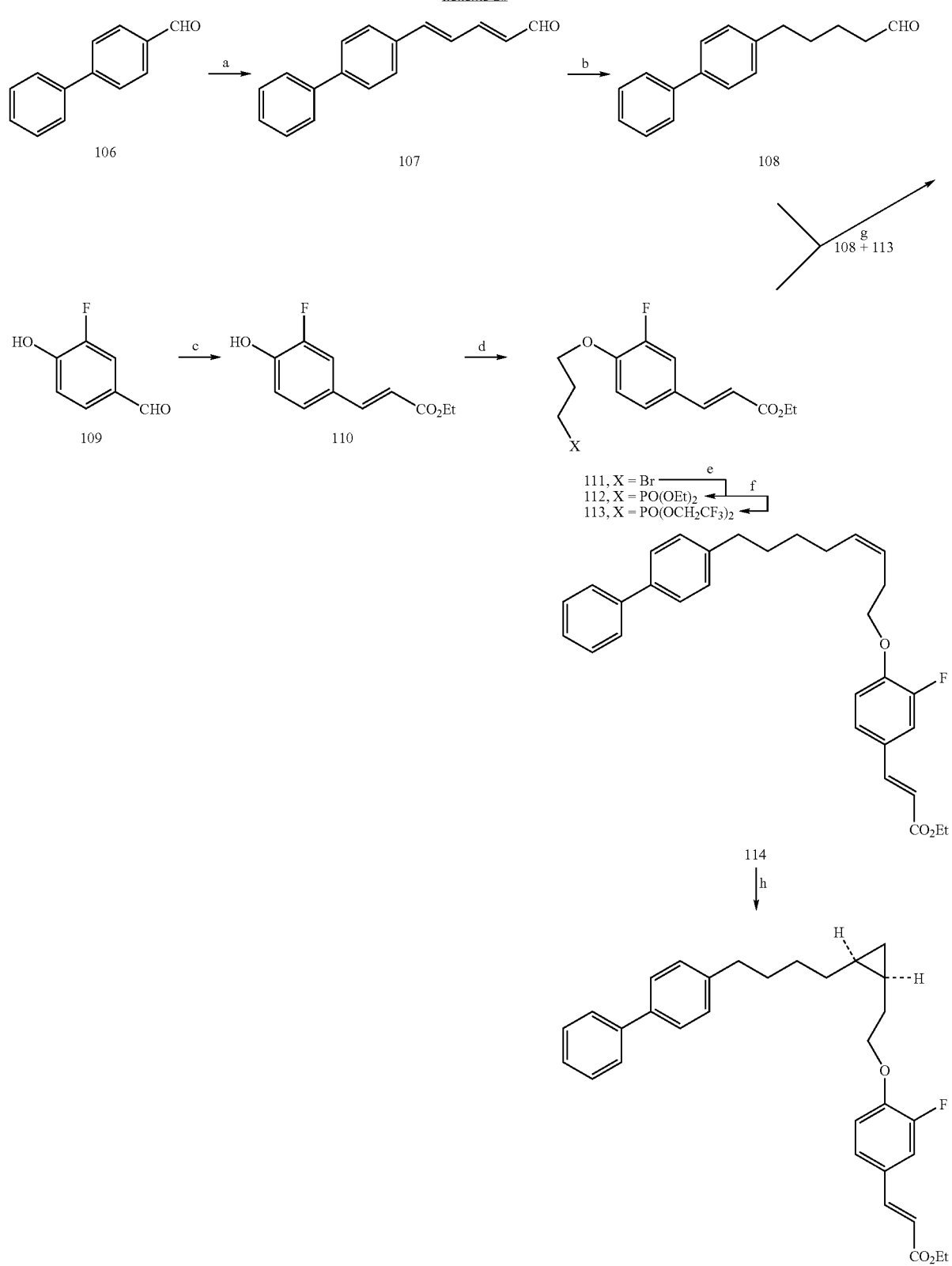
Key: a) (EtO)$_2$POCH$_2$CH=CHCHO, NaH; -78° C. → room temperature, THF; b) H$_2$, Pd/C, MeOH; c) (EtO)$_2$POCH$_2$CO$_2$Et, NaH, THF; d) excess Br(CH$_2$)$_3$Br, Et$_3$N; e) EtO$_3$P, toluene, Δ; f) CF$_3$CH$_2$OH, excess, Δ; g) 113 + NaH, THF; then 108; h) Chiral cyclopropanation.

The 5-ketotetrazole, BPH-114, is somewhat similar to the aforementioned example in Scheme 20 in that a carbonyl compound must be homologated and then coupled to an imidazole ring N, and is shown in Scheme 21. The known spiroketone 116 is easily converted to the aldehyde and reacted with a Horner Emmons reagent to afford the homolog required for olefinic coupling. Thus, trimethylsilyl chloromethyllithium reacts with 116 to afford transiently, the epoxide 117, that upon facile rearrangement gives the one carbon homolog aldehyde 118. Now, reaction with (EtO)$_2$POCH$_2$CO$_2$Et, NaH gives rise to the dienal 119. Hydrogenation of 119 provides the requisite partner for Wittig reaction, 120. For the other moiety, 1,4-dibromobutane reacts with the anion of imidazole-4-carboxaldehyde to give the N-bromobutyl imidazoleCHO, 121. Next, reaction of the aldehyde of 121 with N-PMB protected lithio tetrazole 122 gives the alcohol 123, oxidation of which leads to the second synthon, 124. Finally, Horner Emmons reaction of 120 with 124 gives the protected version of the final product, 125. Oxidative cleavage of the PMB group then furnishes the target BPH-114.

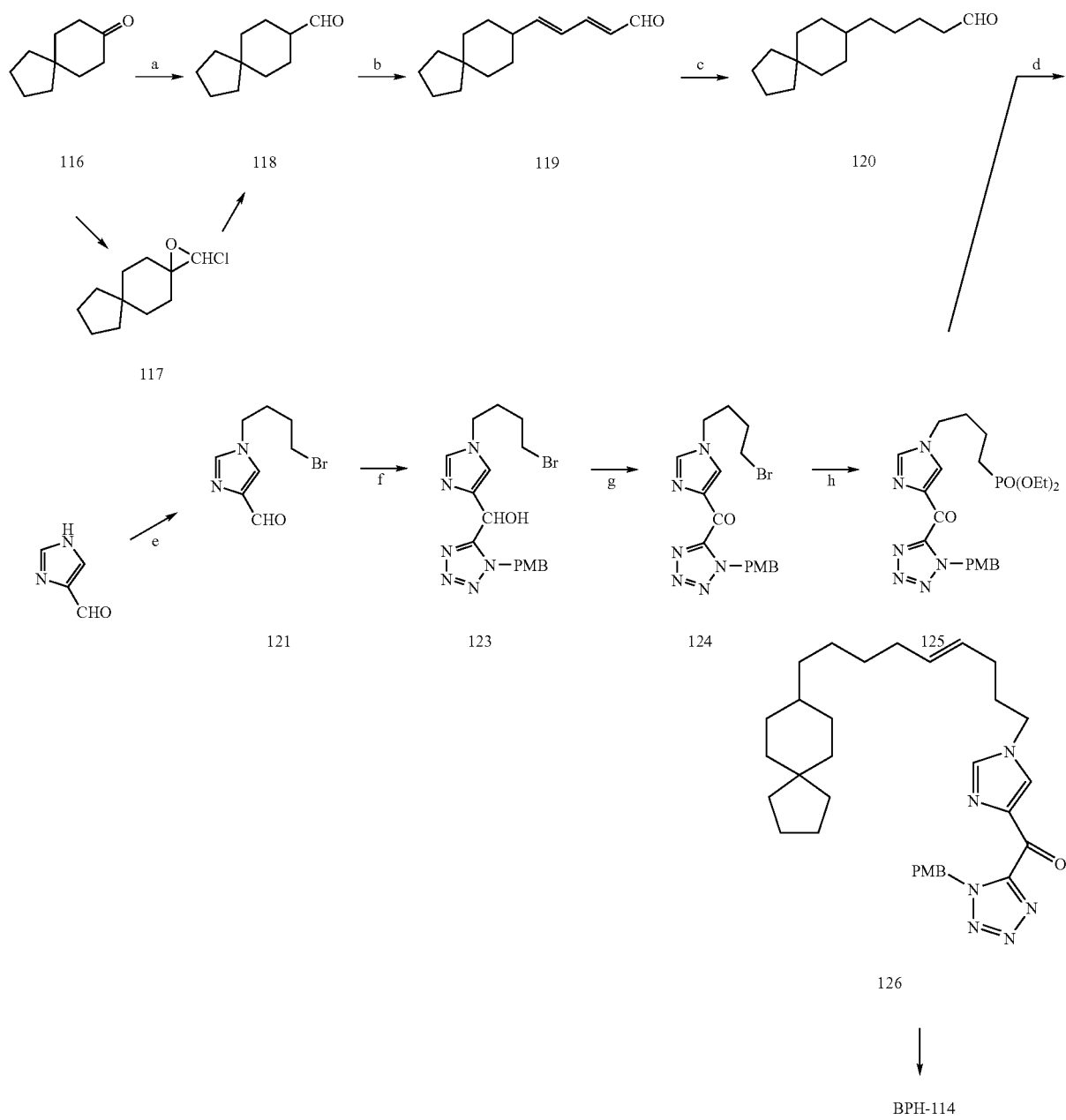

Scheme 21

Key: b) (EtO)$_2$POCH$_2$CH=CHCHO, NaH; -78° C. → room temperature, THF; c) H$_2$, Pd/C MeOH; d) 125 + NaH, THF; then 120; e) excess Br(CH$_2$)$_4$Br, Et$_3$N; f) 5-lithio-1N-PMB-tetrazole 122; g) Swern oxidation; h) EtO$_3$P, toluene, Δ; i) CAN, HOH, DCM or TFA/DCM.

The final two illustrative examples are shown in the following Scheme 22, both compounds BPH-115 (128) and 116 (129) employing essentially similar chemistry but different starting materials. Either aldehyde 130 or 131 condenses with TZD and base to afford intermediate α,β-unsaturated TZDs. These are reduced as in Scheme 21 with Mg in MeOH to afford the aryl halides 132 and 133. In the case of the benzothiazole 132, coupling of the propargylic ZnCl reagent, formed from the propargyl chloride with Zn metal, is coupled via Pd(0) to provide the acetylenic TZD, 138. The S atoms may provide sufficient poisoning for a Pd/C hydrogenation to be controlled, or alternatively, Lindelars catalyst may be employed to afford the desired Z olefin 128, BPH-115. For the quinoxaline 133, a benzylic halide is converted to a benzylic ZnCl and coupled to the aryl chloride with Pd(0). The resulting product is the required BPH-116.

Scheme 22
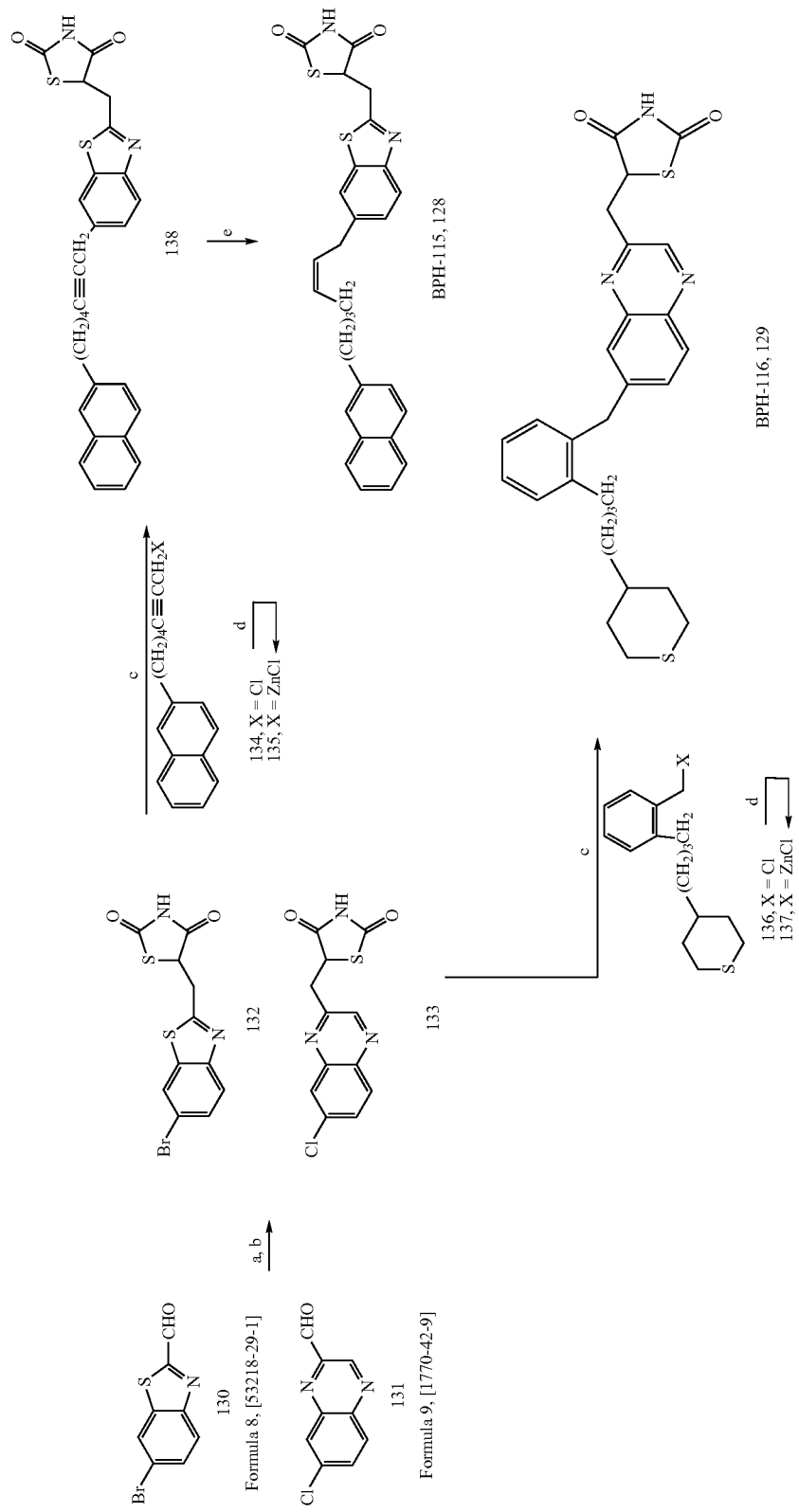
Key: a) thiazolidinedione, 2NaH, THF; b)Mg, MeOH; c) Pd(0), DIPEA, benzene; d) 134 + Zn powder, microwave, THF; e) Lindelar's Catalyst, H₂, EtOAc.

Methods of Use of the Compounds

The compounds can be used in a variety of therapeutic applications.

This invention relates to the prevention and treatment of diseases involving tissues that express PPARgamma and/or PPARalpha, and/or PPARdelta and to new methods for treating inflammatory, proliferative, degenerative diseases, and diseases involving angiogenesis and neovascularization, deriving from organs and tissues of all embryological origins. These include vitreoretinopathies and uveitis, hereditary and non-hereditary degenerative neural (e.g. multiple sclerosis) and retinal diseases (e.g. retinitis pigmentosa), diseases resulting from hypoxia or vascular ischemia (e.g. ischemnic heart disease), diseases involving angiogenesis and neovascularization (e.g. neoplastic diseases), age-related degenerative diseases (e.g. of the retina and skin) such as those associated with diabetes, ischemia and aging, and degenerative or dystrophic diseases or involving premature apoptosis (e.g. retinal dystrophies and retinopathies resulting from glaucoma), and chronic systemic diseases (e.g. diabetes, congestive heart failure, asthma, chronic obstructive pulmonary disease, cardiomyopathy, hypertension, atherosclerosis, myocardial fibrosis, osteoporosis, inflammatory bowel diseases). This invention relates to the treatment of diseases tissues and organs regardless of etiological agent. For example, the treatment of corneal injury or ulceration caused by unrelated etiological agents: 1) foreign body (e.g. contact lens), infectious agent (e.g. *candida albicans, chlamydia trachomatis*, cytomegalovirus or human immunodeficiency virus), physical agent (e.g. UV radiation), chemical agent (e.g. acids, caustic solvents) chronic systemic disease (e.g. autoimmune or collagen vascular diseases).

The invention can be used to treat various diseases. Some examples of specific embodiments of this invention are described below.

The compounds can be used to treat the group of metabolic diseases associated with insulin resistance, that consists of: obesity, type 2 diabetes mellitus, gestational diabetes, impaired glucose tolerance, Cushing's syndrome (e.g. secondary to chronic glucocorticoid therapy), polycystic ovarian syndrome. The compounds can be used to treat the metabolic disease, osteoporosis.

The compounds can be used to treat inflammatory, proliferative or degenerative skin disease, such as psoriasis, keratitis, hidradenitis, ichthyosis, acne vulgaris, rosacea, verrucae and other HPV infections, atopic dermatitis, allergic dermatitis, chemical (irritant) dermatitis, seborrheic dermatitis, solar dermatitis, acute and chronic eczema, seboirheic keratosis, senile keratosis, actinic keratosis, photo-induced keratosis, skin aging, thinning skin, dry skin, wrinkle formation, photo-induced skin aging, keloids, lichen planus, acute or chronic pruritus.

The compounds can be used to treat occlusive vascular disease, such as atherosclerosis, thrombosis, thromboembolism, restenosis after an invasive procedure (e.g. angioplasty and vascular grafting).

The compounds can be used to treat cardiovascular disease, such as arteritis, endarteritis, endocarditis, myocarditis, arterial plaque (fibrous cap) rupture, acute coronary syndrome, unstable angina, myocardial infarction, myocardial ischemia, ischemic cardiomyopathies, non-ischemic cardiomyopathies, post-myocardial infarction cardiomyopathy and myocardial fibrosis, drug-induced cardiomyopathy, congestive heart failure.

The compounds can be used to treat occlusive vascular disease associated with hyperglycemia, hyperinsulinemia, or obesity.

The compounds can be used to treat ophthalmic inflammatory disease such as uveitis, uveoretinitis, panuveitis, retinitis, iridocyclitis, immunological endophthalmitis, choroiditis, vitreitis, keratitis, dry eye syndrome, corneal ulceration, age-related macular degeneration, glaucoma, conjunctivitis, and conjunctival ulceration, and neovascular proliferative disease such as age-related macular degeneration, exudative macular degeneration, atrophic macular degeneration, crystalline retinopathy, retinal toxicosis of systemic medications, idiopathic central serous choroidopathy, macular edema, or primary or secondary retinal detachment.

The compounds can be used to treat inflammatory disease such as retinovascular disease or retinopathy, vitreoretinopathy or vasculopathy of vasculo-occlusive or idiopathic etiology, or associated with telangiectasias or aneurysms, or associated with lupus erythematosus, rheumatoid arthritis, multiple sclerosis, myasthenia gravis, uveoretinitis or diabetes mellitus, or associated with intraocular surgery or primary or secondary retinal detachment resulting from a disease or injury.

The compounds can be used to treat inflammatory autoimmune disease mediated by T lymphocytes, such as chronic rheumatoid arthritis, juvenile rheumatoid arthritis, systemic lupus erythematosus, Hashimoto's disease, Crohn's disease, ulcerative colitis, type 1 diabetes mellitus, autoimmune neuritis.

The compounds can be used to treat inflammatory, degenerative disease such as steatosis, fibrosis, and/or cirrhosis of the liver induced by drugs (e.g. HMG-CoA inhibitos, isoniazid), chronic alcohol consumption, or resulting from poisonous toxins (e.g. mushroom poisoning).

The compounds can be used to treat inflammatory disease that is a result of rejection of an allograft transplantation and is associated with acute allograft rejection, chronic allograft rejection, graft versus host disease.

The compounds can be used to treat inflammatory disease that is a neuro-degenerative such as Alzheimer's disease, HIV-related dementia, Parkinson's disease, amyotropic lateral sclerosis, multiple sclerosis, Guillain-Barre syndrome, chronic pain, allodynia, encephalitis, encephalomyelitis, neuritis, myesthenia gravis, Eaton-Lambert syndrome, congenital and secondary ataxias.

The compounds can be used to treat inflammatory disease that are non-carcinogenic and ischermic such as disease associated with angiogenesis and neovascularzation (e.g. ischemic heart disease, retinal and choroidal angiogenesis).

The compounds can be used to treat proliferative, inflammatory disease such as angiogenesis and neovascularization that is associated with a carcinogenic (neoplastic) disease.

The compounds can be used to treat carcinogenic disease such as fibrosarcoma, myxosarcoma, liposarcoma, chondrosarcoma, osteogenic sarcoma, chordoma, angiosarcoma, enthotheliosarcoma, lymphangiosarcoma, lymphangioendotheliosarcoma, synovioma, mesothelimoa, Ewing's tumor, leiomyosarcoma, rhabdomyosarcoma, colon carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The compounds can be used to treat inflammatory disease associated with dysfunction of a T lymphocyte, or T lymphocyte subtype, leading to development of an autoimmune disease.

The compounds can be used to treat any disease that involves pathological apoptosis (programmed cell death). A compound of this invention may be effective to slow, reverse, prevent or treat said disease, wherein the disease is an ischemic disease (cardiomyopathies, congestive heart failure), atherosclerosis, or an autoimmune disease (multiple sclerosis, Alzheimer's disease, Parkinson's disease, hepatic fibrosis or cirrhosis, myelodysplasis, arthritis and joint-disease).

The compounds can be used to treat pulmonary disease such as asthma, chronic obstructive pulmonary disease, reactive airway disease, pulmonary fibrosis, or pulmonary hypertension.

The methods of treatment in one aspect of this invention are practiced by administering to a human in need thereof a dose of a compound (or pharmaceutically acceptable salts and solvates thereof in acceptable pharmaceutical excipients) that modifies the activity of PPAR. The methods include treating a human subject prophylactically to alter inflammation, apoptosis, proliferation, angiogenesis, neovascularization, immune dysfunction, and expression of oncogenes and other genes controlling cell metabolism. The present method includes both medical therapeutic and/or prophylactic treatment, as necessary.

The methods of treatment provided by this invention are practiced by administering to a human or vertebrate animal in need a dose of a compound, or a pharmaceutically acceptable salt, ester, solvate or tautomer thereof, that activates either PPARgamma, or PPARalpha, or PPARdelta or compounds that activate more than one of these receptors. In another aspect, the novel compounds used to practice this invention are set forth above. The specific diseases and associated disorders that can be treated with the compounds described in this invention are listed in Tables I through X. Using a method of the invention, therapeutic compounds are typically administered to human patients topically to the skin or mucous membranes, by extra-ocular application, intraocularly (by chemical delivery system or invasive device), or systemically (e.g. sublingually, by suppository, by oral ingestion, intradermallyi by inhalation, intramuscularly, intra-articularly, intravenously, or other parenteral route). Parenteral administration by a particular route is used in appropriate circumstances apparent to the practitioner. Oral administration is the preferred route for chronic diseases. Topical administration is the preferred route for dermatological diseases. Extra-ocular application is the preferred route for ocular diseases involving the anterior segment of the eye, or chronic diseases Preferably, the compositions are administered in unit dosage forms suitable for single administration of precise dosage amounts.

To prepare a topical formulation for the treatment of ophthalmological or dermatological or other disorders listed in Tables I through X, a therapeutically effective concentration of the compound in one embodiment is placed in a vehicle such as a dermatological one that is known in the art. The amount of the therapeutic compound to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

Administration

The therapeutic compound is optionally administered topically by the use of a transdermal therapeutic system (see Barry, Dermatological Formulations, (1983) p. 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

For ophthalmic applications the therapeutic compound is formulated into solutions, suspensions, and ointments appropriate for use in the eye. The concentrations are usually as discussed above for topico-local preparations. For ophthalmic formulations, see Mitra (ed.), Ophthalmic Drug Delivery Systems, Marcel Dekker, Inc., New York, N.Y. (1993) and also Havener, W. H., Ophthalmic Pharmacology, C. V. Mosby Co., St. Louis (1983).

The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

The concentration of the therapeutic compound used depends on the mode of delivery. For topical ophthalmic and extraocular formulations, the concentration of the therapeutic compound is in the range of about 0.01% weight/weight (w/w) to about 10% w/w. For example, the concentration of the therapeutic compound for this mode of delivery is in the range of about 0.025% w/w to about 2.5% w/w. Solid dispersions of the therapeutic compound as well as solubilized preparations can be used. For intraocular formulations (chemical delivery or delivery by invasive device), the therapeutic compound in one embodiment is delivered at a concentration high enough to achieve a final concentration in the range of about 0.1 micromol/L to about 10 micromol/L within the target ophthalmic compartment (e.g. the posterior chamber for the treatment of retinal diseases). Typically, for this mode of delivery, the final concentration of the therapeutic compound is in the range of about 0.25 micromol/L to about 5 micromol/L. Solid dispersions of the therapeutic compound as well as solubilized preparations can be used. Thus, the precise concentration is subject to modest but not undue experimental manipulation well within the skill of the ordinary medical practitioner in order to optimize the therapeutic response. Suitable vehicles include oil-in-water or water-in-oil emulsions for preparation of ointments using mineral oils, petrolatum, lanolin, glycerin and the like as well as gels such as hydrogel. A preferred embodiment of the present invention involves administration of semi-solid or solid implants containing PPARgamma agonists.

Compounds useful for the application of methods described in this invention include all existing synthetic and naturally occurring PPARgamma agonists. Preferred PPARgamma agonists useful for the application of methods described in this invention include the novel compounds described in this invention and in the following submitted patent applications: Pershadsingh H A, Avery M A. 1,2-Dithiolane Derivatives, (U.S. patent application Ser. No. 09/520,208) and Pershadsingh H A. Novel Dithiolane Derivatives, (U.S. Provisional Patent No. 60/157,890). Preferred PPARgamma agonists may include other drugs, which may be in slow release form for topical or systemic delivery. This may be accomplished in a preferred embodiment by using instrumentation and techniques described in U.S. Pat. No. 5,817,075 and U.S. Pat. No. 5,868,728.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. In one embodiment the therapeutic compound is prepared in an aqueous solution (discussed below) in a concentration of from about 0.1 to about 100 mg/ml. More typically, the concentration is from about 1 to 10 mg/ml or about 20 mg/ml. Concentrations below 1 mg/ml may be necessary in some cases depending on the solubility and potency of the compound selected for use. The formulation, which is sterile, is suitable for various topical or parenteral routes including sublingual, by suppository (e.g. per-rectum or vaginal application), oral, intravascular, intradermal, by inhalation, intramuscular, intra-articular, intravenous, or other parenteral route.

In addition to the therapeutic compound, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention may include a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration areknown to those of skill. See generally Remington's Pharmaceutical Science 15th ed., Mack Publishing Co., Easton, Pa. (1980).

Slow Release Delivery

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

Delivery by Invasive Device

As mentioned above, delivery intravascularly, intra-articularly, intramuscularly, intra-articularly, intradermally, or other parenteral route can be accomplished by injection, cannula or other invasive device designed to introduce precisely metered amounts of a desired formulation to a particular compartment or tissue. For example, delivery to certain areas within the eye, in situ, can be accomplished by injection, cannula or other invasive device designed to introduce precisely metered amounts directly or contained in a reservoir for slow release in situ, of a desired formulation to a particular compartment or tissue within the eye (e.g. anterior or posterior chamber, uvea or retina). Preferably, a solid or semisolid implant can be delivered subretinally using the instrumentation and methods described in U.S. Pat. No. 5,817,075 and U.S. Pat. No. 5,868,728.

Routes of Administration

Therapeutic agents of the invention are usually delivered or administered topically for treating disorders involving the eye that are listed in Tables I through X. Oral administration is preferred for disorders in Tables I through X that cannot be treated effectively by topical therapy. Additionally, the agents can be delivered parenterally, especially for treatment of retinitis and degenerative retinal diseases, and for other conditions in Tables I through X, that do not respond to oral or topical therapy, or for conditions where oral or topical therapy is not feasible. Parenteral therapy is typically oral, intraocular, transcutaneous, intradermal; intrathecal, intramuscular, intra-articular, by inhalation, intravascular, sublingual, by suppository (e.g. per-rectum or vaginal application), by inhalation, or other parenteral route.

A preferred way to practice the invention for dermatological or ophthalmic disorders in Tables I through X to which this method is applicable, is to apply the compound of interest, in a cream, lotion, ointment, or oil based carrier, or some other suitable vehicle directly to the lesion. For example, the concentration of therapeutic compound in a cream, lotion, or oil is 0.025 to 2.5%. In general, the preferred route of administration is oral, topical, intraocular or parenteral. Topical administration is preferred in treatment of lesions of the skin as in psoriasis, external eye as in conjunctivitis, keratitis, scleritis, squamous cell carcinoma, corneal erosion, dry eye syndrome, and anterior compartment of the eye as in glaucoma, uveitis and other diseases of the uveal tract, where such direct application is practical and clinically indicated.

Oral administration is a preferred alternative for treatment of other lesions discussed in Tables I through X, where direct topical application is not useful as in the treatment of chronic or acute systemic diseases, and diseases of the posterior segment of the eye, as in uveitis, glaucoma, optic neuritis or retinitis. Intravascular (intravenous being the preferred route) administration may be necessary in disorders that cannot be effectively treated by topical or oral administration. Administration by inhalation is preferred for lung diseases such as broncho-constrictive disease, asthma, and chronic obstructive pulmonary disease.

Intraocular, transcutaneous, intradermal, intrathecal, intramuscular, intra-articular injections or other invasive technique are preferred alternative in cases where the practitioner wishes to treat one or a few specific areas or lesions depending on their location within the eye. Usually, the compound is delivered in an aqueous solution. Additionally, the therapeutic compounds are injected directly into lesions (intra-lesion administration) in appropriate cases. Intradermal administration is an alternative for extraocular lesions. Intra-lesional and intradermal injections are alternative routes of application for certain lesions, e.g. extraocular neoplastic or hyperplastic lesions such as squamous cell carcinoma and condyloma, respectively. Inhalation therapy is preferred for pulmonary diseases, sublingual and intra-rectal suppository is preferred for rapid delivery or in clinical situations where delivery via the oral or intravascular route is inconvenient or problematic. Application via vaginal topical formulation or via suppository formulation is preferred for diseases localized to the vagina or other segment of the urogenital tract.

The compounds of this invention can be formulated to have a wide spectrum of solubility properties, where the oil/water diffusion coefficient (o/w) values may range from <1 (very hydrophilic) to >6 (very hydrophobic). For pulmonary applications, preferred therapeutic compounds are ester derivatives, formulated into solutions, suspensions, aerosols and particulate dispersions appropriate for application to the pulmonary system. The therapeutic agent may be inhaled via nebulizer, inhalation capsules, inhalation aerosol, nasal solution, intra-tracheal as a solution via syringe, or endotracheally tube as an aerosol or via as a nebulizer solution. Similarly, structures derivitized as acetates, succinates, glycinates, etc., and rendered water soluble, are best suited for delivery across the gastrointestinal mucosa.

Dosage and Schedules

An effective quantity of the compound of interest is employed in treatment. The dosage of compounds used in accordance with the invention varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. A typical dose may range from 1 mg/day to 500 mg/day of the compound depending on the ability of the compound to influence the PPAR receptors of interest and the disease under consideration.

PPARgamma/PPARalpha Co-Ligands (Co-Activators):

In one embodiment, ligands that are dual activators (co-activators) of PPARgamma and PPARalpha, are those compounds with an EC50 for PPARgamma transactivation within about 100-fold of the EC50 for PPARalpha transactivation. More typically, the preferred EC50s for PPARgamma and PPARalpha transactivation are within about 10 to 20-fold of one another. However, the EC50s for activation of PPARalpha and PPARgamma could be within 1000 fold of each other.

The $EC_{50}$ is the concentration of a compound required to bind to or activate 50% of the receptor in a sample or a subject. Broadly, for a PPAR ligand, e.g. a thiazolidinedione, the oral dose in one embodiment may be determined from the following formula:

$$\text{oral dose (in mg)} = (k_1)(EC_{50})(k_2)\,(LBW)(MW);$$

wherein $k_1$ is a dimensionless constant of 5 to 100; $EC_{50}$ is the concentration (amount) of compound required to activate or bind to 50% of PPARgamma or PPARalpha in the sample or patient and is in mole/L units; $k_2$ is the fractional water content of the lean body weight (LBW) of the patient=0.72 L/kg, (see, GEIGY SCIENTIFIC TABLES, VOL. 1, Lentner (ed.), p 217, Giba-Geigy Ltd., Basle, Switzerland (1981); and MW is the molecular weight of the compound in g/mole.

For example, troglitazone is a compound encompassed by the methods of this invention. A man with diagnosis of early stage prostate cancer in situ has a lean body weight (LBW) of 70 kg. If $k_1$=10; the $EC_{50}$ for troglitazone=$2.4 \times 10^{-6}$ mol/L and the molecular weight of troglitazone=442 g/mol, then the oral dose in milligrams=$(10)(2.4 \times 10^{-6}$ mol/L$)(0.72$ L/kg$\times 70$ kg$)(442$ g/mol$)$ or 535 mg. Similarly, an effective dose of rosiglitazone in milligrams for an average man is $(10)\,(0.06 \times 10^{-6}$ mol/L$)\,(0.72$ L/kg$\times 70$ kg$)\,(304$ g/mole$)$ or 9.2 mg.

Typically, the dosage per day of the PPAR ligand of this invention will depend on the its affinity for PPARgamma or PPARalpha or PPARdelta. The dosages of compounds with high affinity, e.g., like rosiglitazone, will fall between about 0.1 mg to about 10 mg per day. The dosages of compounds of intermediate affinity, e.g. like pioglitazone, will range from about 10 mg to about 100 mg per day. The dosages of compounds with low affinity, e.g., like troglitazone, will fall from about 100 mg to about 1000 mg per day.

An oral dosing schedule is typically, a single dose once a day. However, more than one dose can be given per day. Because of the lower incidence of undesirable side effects, the compounds of this invention can be given until improvement in the inflammatory process or disease involving neovascularization is observed. Because the compounds of this invention are to some degree fat-soluble, in a preferred embodiment, the compounds are administered with food. The fats in food provide a lipid micellular phase in which the particular PPAR ligand of this invention can solubilize and be more effectively absorbed.

Depending on the EC50 for PPAR activation, a dosage range for local treatment is about 0.025% to about 10% (weight/volume) in a suitable solvent applied that permits release of the compound into the prostate tissue. For high affinity ligands, a preferred range is about 0.025% to 0.1%. For intermediate affinity ligands, a preferred range is about 0.1% to 0.5%. For low affinity ligands, a preferred range is about 0.5% to 5%. One of skill will realize that the dosage for local treatment will vary depending on the compound used, its hydrophobicity and hydrophilicity, and the EC50 for PPARgamma and/or PPARalpha activation and/or PPARdelta activation. For example, the PPAR ligands of this invention may have vastly different affinities for PPARalpha and PPARgamma, or the may be similar, i.e. within about one to two orders of magnitude. Typically, the greater the affinity, the more effective the compound, and the lower the dosage that is an effective amount. Therefore, a lower concentration of a drug (with a higher affinity) in a unit dosage form comprises an effective amount.

Typically, the local dosage is administered at least once a day until a therapeutic result is achieved. The dosage can be administered twice a day, but more or less frequent dosing can be recommended by the clinician. Once a therapeutic result is achieved, the compound can be tapered or discontinued. Occasionally, side effects warrant discontinuation of therapy.

An effective quantity of the compound of interest is employed in treatment. The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 0.1 mg to about 1000 mg once or twice a day depending on the binding affinity of the compound for PPARgamma or PPARalpha or PPARdelta. For example, the typical oral dose of the thiazolidinediones, rosiglitazone and pioglitazone, presently approved for the treatment of type 2 diabetes mellitus, is 4 to 8 mg and 15 mg to 45 mg daily, respectively.

Using rosiglitazone as the prototype agent for the purpose of this invention, a convenient oral dose for an adult patient is 4 to 8 mg once a day, or 2 to 4 mg twice a day. A dosage range for topical treatment is about 0.1% to about 1% (weight/volume) in a gel, cream or ointment, applied twice a day. A usual dose for intramuscular or intraocular injection is 0.25 to 2.5 mg, depending on the compartment of the eye to be treated and on the lean body mass of the patient. A typical dosage for intra-dermal administration is about 2.5 to 25 mg per injection per site. A typical dosage for intravenous or intramuscular administration in an adult patient would be between 50 and 250 mg per day given in single or divided doses depending on the judgement of the practitioner.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

This invention further relates to the use of each of the subject compounds in the treatment of the diseases listed in Tables I through Table X, administered as either as a single agent, or in combination with a natural or synthetic compound selected from one or more of the following categories: PPARalpha agonist, a PPARdelta agonist, or PPARgamma agonist; a rexinoid or other RXR agonist; a vitamin D derivative or other VDR agonist; a glucocorticoid or other GR agonist; a LXR or LXR/RXR agonist (e.g. an oxysterol); a FXR or FXR/RXR agonist (e.g. farnesol, chenodeoxycholic acid, a bile acid); an HMG-CoA reductase inhibitor; a CETP inhibitor, e.g. a substituted-1,2,3,4-tetrahydroquinoline; a pharmacological agent that increases the expression or upregulates ABC1; a beta3-adrenoceptor agonist; a calcineurin inhibitor (e.g. cyclosporine A, tacrolihmus, sirolimnus); an anti-hypertensive angiotensin converting enzyme (ACE) inhibitor; and an anti-hypertensive angiotensin receptor blocker (ARB)

Synergistic therapeutic effects can be achieved by oral or topical administration of the drugs encompassed in the current invention together with a second agent selected from the above-identified categories of compounds, administered orally, topically or intravenously. A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without PPARgamma activators. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D, calcipotriene and calcipotriol. The dosage range and routes and frequency of administration of PPARgamma activators required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. The dosages and the modes and frequency of administration of the vitamin D or retinoid related compounds for synergistic topical therapy would be similar to those ordinarily recommended for these agents when given without PPARgamma activators. The dosage range and the modes and frequency required for topical administration of the flavonoid thiazolidine derivatives given in combination with vitamin D or retinoid related compounds are the same as those described elsewhere in this disclosure.

Synergistic therapeutic effects can be achieved by oral or topical administration of the drugs encompassed in the current invention together with orally, topically or intravenously administered natural or synthetic antioxidants. These include ascorbic acid and its derivatives (e.g. vitamin C), the tocopherols (e.g. vitamin E, vitamin E succinate), carotenes and carotenoids (e.g. beta-carotene), alpha-lipoic acid, probucols, flavones, isoflavones and flavonols (e.g. quercetin, genistein, catechin, apigenin, lutein, luteolin), glutathione and its derivatives (e.g. N-acetylcysteine and dithiothreitol), and phytoestrogens and phenolic anthocyanidin and procyanidin derivatives (e.g. resveratrol, cyanidin, cinnamic acid).

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving myocardial fibrosis, myocardial ischemia, pathological conditions secondary to the autoimmune response to allograft transplantation, the splanchnic blood flow, including hepatic fibrosis, cirrhosis and oesophagal varices, the compounds of the invention can provide cytoprotection.

Screening Assays and Cell Systems

Assays for screening for compounds that modify the activity of PPARgamma and/or PPARalpha and/or PPARdelta can be conducted using methods known in the art such as PPAR transactivation (Willson et al. *J. Med. Chem.* 43:527-50 (2000)) and the fluorescence resonance energy (FRET) assay (Zhou G., et al., *Mol Endocrinol* 12(10):1594-604 (1998). In one embodiment the following cell systems are employed. Human endothelial cells and vascular smooth muscle (VSM) cells which are known to express both PPARgamma and PPARalpha can be used. Alternatively, isolated human peripheral T lymphocytes from normal healthy donors or a mammalian cell line such as a Jurkat T cell line poorly express PPARalpha and PPARgamma can be used. To test specific PPARgamma activating compounds, lymphocytes or Jurkat cells are transfected with the PPARgamma expression vector. To test mixed PPARalpha and PPARgamma activating compounds, (PPARalpha/PPARgamma co-ligands), lymphocytes or Jurkat cells are transfected with both PPARalpha and PPARgamma expression vectors. Other cells expressing PPARdelta may also be employed.

The binding of agonist ligands to the receptor results in changes in the expression level of mRNAs encoded by PPAR target genes. This process, "transactivation", is determined by cell-based assays which monitor this functional activity. Transactivation assays use cells that have been transfected with a vector expressing the receptor as well as a second vector containing a DNA direct repeat (DR-1) response element and a reporter gene, which encodes an enzyme such as chloramphenicol acetyltransferase, secreted placental alkaline phosphatase, or firefly luciferase. Activation of the receptor by agonist ligands leads to induction of reporter enzyme expression, which can be conveniently assayed using standard colorimetric or photometric methods, A procedure used to test the compounds of this invention is the PPAR-GAL4 transactivation assay, which uses chimeric receptors where the PPAR LBD is fused to the DBD of the yeast transcription factor GAL4 and employs a reporter gene containing a GAL4 response element, and has previously been described in detail (Lehmann et al., *J. Biol. Chem.* 1995, 270, 12953-12956). Briefly, cells are incubated with 10% delipidated fetal calf serum and the test compound at the appropriate concentration. After an additional 24 h, cell extracts are prepared and assayed for alkaline phosphatase and beta-galactosidase activity. Alkaline phosphatase activity was corrected for transfection efficiency using the beta-galactosidase activity as an internal standard. Compounds which elicited on average at least 70% activation of PPAR versus rosiglitazone (positive control for PPARgamma specific activation) or versus Wy-14643 (positive control for PPARalpha specific activation) were considered full agonists (Willson et al., *J. Med. Chem.* 2000; 43:527-50; Henke et al. *J. Med. Chem.* 1998; 41:5020-36).

The scenarios described below employ representative compounds of these classes for screening assays and in examples wherein they are administered to human subjects in the treatment of specified diseases. The following examples on screening the compounds for certain functional activities of interest and for using the compounds to treat various clinical disorders are included for illustrative purposes and are not intended to limit the scope of methods for screening and using the compounds of the current invention.

The invention will be further understood by the following non-limiting examples.

EXAMPLES

Example 1

Method for Evaluating the Activity of Compounds Developed Using this Invention—Binding Assay For the binding assay, bacterial expression plasmids for the ligand binding domains of the PPAR subtypes, cDNAs encoding the hinge and ligand binding domains of hPPAR (amino acids 167-468), MPPAR (amino acids 167-468), xPPAR (amino acids 174-474), and xPPAR (amino acids 178-477) are obtained. GST-PPAR fusion proteins or glutathione S-transferase (GST) alone as a control are expressed in BL21(DE3) plysS cells and extracts prepared by freeze-thawing the cells in bacterial lysis buffer (10 mM Tris, pH 8.0/250 mM KCl/1 mM DTT/1% Triton X-100) followed by centrifugation at 40,000×g for 30 min. Glycerol is added to the bacterial extracts to a final concentration of 10%. Bacterial extracts are dialyzed extensively against bacterial lysis buffer containing 10% glycerol to remove glutathione that might interfere with the stability of the various FAs and eicosanoids in the competition binding assays. For saturation binding analysis or competition binding assays, bacterial extracts (50 microg protein) containing either GST-xPPAR or GST-xPPAR are incubated at 4° C. for 2-3 hr in buffer containing 10 mM Tris (pH 8.0), 50 mM KCl, and 10 mM DTT with [3H]GW2331 in the presence or absence of unlabeled GW2331 or the various FAs or eicosanoids. Bound radioactivity was separated from free radioactivity by elution through 1 ml Sephadex G-25 protein desalting columns (Boehringer Mannheim). Bound radioactivity eluted in the column void volume and was quantitated by liquid scintillation counting.

Several radioligands are now available for use in conventional competition binding assays: [3H]GW 2331 for PPARalpha; [3H]rosiglitazone (B3RL49653), [3H]AD-5075, and [125I]SB-23663643 for PPARgamma; and [3H]GW 243344 and [3H]L-78348345 for PPARdelta. Each of these radioligands is reported to show specific binding to the corresponding PPAR subtype. Initial PPAR binding assays used gel filtration to separate the bound radioligand from the free ligand. The use of scintillation proximity assay (SPA) technology has greatly increased the throughput of PPAR competition binding assays. SPA beads emit light when held in close proximity to a suitable radionuclide (e.g. 3H or 125I). If the receptor is attached to the SPA bead, binding of a radioligand to the PPAR LBD leads to a readily detectable signal. Displacement of the radioligand by a test compound leaves the free radioligand in solution, where it can no longer promote emission by the SPA bead. This technology removes the need to separate free radioligand from the bound ligand, greatly simplifying automated high-throughput screening. The homogeneous format of the SPA binding assay allows determination of equilibrium binding affinities and also permits the use of relatively low-affinity radioligands.

Example 2

Method for Evaluating PPAR Activity of the Compounds of this Invention Using a Transactivation Assay or FRET Assay The binding of agonist ligands to a nuclear receptor results in transactivation, i.e., changes in the expression level of mRNAs encoded by PPAR target genes. Cell-based assays have been developed which monitor this functional activity. Transactivation assays use cells that have been transfected with a vector expressing the receptor as well as a second vector containing a DR-1 response element and a reporter gene, which encodes an enzyme such as chloramphenicol acetyltransferase, secreted placental alkaline phosphatase (SPAP), or firefly luciferase. Activation of the receptor by agonist ligands leads to induction of reporter enzyme expression, which can be conveniently assayed using standard colorimetric or photometric plate readers.

In the case of PPARs, an ideal assay is the PPAR-GAL4 transactivation assay using chimeric receptors where the PPAR LBD is fused to the DBD of the yeast transcription factor GAL4. This assay employs a reporter gene containing a GAL4 response element. Since mammalian cells do not contain GAL4, only the transfected PPAR-GAL4 chimeric receptors can activate the reporter gene, effectively eliminating interference from endogenous nuclear receptors. In general, PPAR agonists show comparable potency and efficacy in assays using either the PPAR-GAL4 chimeras or the full-length receptors.

COS-1 cells are maintained as described above for the mammalian two-hybrid system. The following plasmids are used for transfection: respective reporter plasmid (1 microg) containing the pGL-GAL4-UAS (17-merx2-globin promoter-luciferase) cotransfected with 0.1 microg of pM(GAL4-DBD)-PPAR (DEF) or pM-PPAR (DEF-AF-2) with or without 1 microg of SRC-1, TIF2, or TRAP220 expression vector. As a reference plasmid for normalization, 10 ng of pRL-CMV plasmid (Promega) is used. Bluescribe M13+(Stratagene) is used as the carrier to adjust the total amount of DNA to 3 microg. added to the medium 12 h after transfection and every 8 h thereafter at each exchange of medium. After 48 h, firefly luciferase activity (from GAL4-UAS) is used to measure transfection efficiency by *Renilla* luciferase activity (from pRL-CMV) as described previously.

Using methods know to those skilled in the art, fluorescence resonance energy tranfer (FRET) assays were used to determine the PPAR activities of representative compounds of the current invention. The assay is an approach for characterizing nuclear receptor agonists or antagonists; individual ligands and determining their potencies that are predictive of in vivo effects (Zhou, et al., Mol. Endocrinol. 12(10):1594-604 (1998)). Example 16 shows FRET assay results demonstrating PPAR activity of representative compounds of the current invention.

Example 3

Method for Screening for Compounds that Modify the Activity of PPARgamma and PPARalpha Based on Inhibition of NF-kappaB Activation Compounds are tested for the ability to inhibit activity of NF-kappaB. Human endothelial cells and vascular smooth muscle cells (VSMC) are known to express both PPARgamma and PPARalpha (Neve B P, et al. Biochem Pharmacol. 2000; 60:1245-1250). Alternatively, isolated human peripheral T lymphocytes from normal healthy donors or a mammalian cell line such as a Jurkat T cell line transfected with the PPARalpha and/or the PPARgamma expression vector may be used in these experiments. One of these selected cell types is stimulated with a concentration of one or a combination of: phytohemagglutinin/phorbol-12-myristate-13-acetate (PHA/PMA), TNF-alpha, interferon-gamma or some other factor that activates NF-kappaB. Activation of NF-kappaB is determined by electrophoretic mobility shift assay similar to that previously described (Rossi A, et al. Proc Natl Acad Sci USA 1997; 94:746-50). Preincubation of the same cells with 5 micromolar of the test compound 2 hours prior to addition of an activator of NF-kappaB inhibits the activation of NF-kappaB otherwise observed in the absence of the benzodithiolanyl derivative.

Example 4

Method for Screening for Compounds that Modify the Activity of PPARgamma and PPARalpha Based on Inhibition of NFAT Activation Isolated human peripheral T lymphocytes from normal healthy donors or a mammalian cell line such as a Jurkat T cell line transfected with the PPARalpha and/or the PPARgamma expression vector, is stimulated with a concentration of one or a combination of PHA/PMA, TNF-alpha, interferon-gamma or some other factor that activates NFAT. Transcriptional activation of NFAT is determined by electrophoretic mobility shift assay similar to that described by Yang et al., *J Biol. Chem.* 2000; 275:4541-4. Preincubation of the same cells with 5 micromolar of the test compound for 2 hours prior to addition of an activator of NFAT inhibits the activation of NFAT otherwise observed in the absence of said compound.

Example 5

Method for Screening for Compounds that Modify the Activity of PPARgamma and PPARalpha Based on Inhibition of IL-2 Production Isolated human T lymphocytes or a mammalian cell line such as a Jurkat T cell line transfected with the PPARalpha and/or the PPARgamma expression vector is stimulated with a concentration of one or a combination of PHA/PMA, TNF-alpha, interferon-gamma or some other factor that activates induction of IL-2 gene expression. Production of IL-2 is determined measuring the concentration of IL-2 in the supernatant from cells using Endogen kits (Wolburn), as described by Yang et al., *J. Biol. Chem.* 2000; 275:4541-4. Preincubation of the same cells with 5 micromolar of the test compound for 12 hours prior to addition of an activator of IL-2 production inhibits the activation of IL-2 production otherwise observed in the absence of said compound.

Example 6

Methods of Determining the Anti-apoptotic Effect of PPAR Ligands in PPARalpha and/or PPARgamma-expressing Cells Inhuman peripheral T lymphocytes from normal healthy donors or a mammalian cell line such as a Jurkat T cell line transfected with the PPARalpha and/or the PPARgamma expression vector, apoptosis (cell death) is induced by adding TNF-alpha (10 ng/ml) and interferon (INF)-gamma (10 ng/ml) (Genzyme, USA). The inhibitory activity of a test compound in preventing this apoptosis is determined by using dexamethasone as the standard, a compound known to have apoptosis inhibitory activity. An aliquot of RPMI-1640 culture medium (containing 10 weight % of fetal bovine serum) is added to each well of a 96-well microplate. Then a test solution of the candidate compound in dimethylsulfoxide is added to the culture medium to give the desired final concentration (0.1 to 10 micromolar). Subsequently, TNF-alpha (40 ng/ml, final concentration) and INF-gamma (10 ng/ml) are added to the culture medium, and cells incubated for 72 hours at 37 degree C. in the presence of 5% carbon dioxide in air. After cultivation, the culture medium is removed from wells by aspiration, and 50 microliter of a 5% (w/v) crystal violet/70% (v/v) methanol solution added to each well to stain living cells. The wells are washed and dried and apoptosis inhibitory activity of the test compound is obtained by determining the optical density by using an absorptiometer [Microplate Reader Model 450, produced by Bio-Rad] at the wavelengths of 570 nm. Dexamethasone standard is compared to the test compound at a final concentration of 1 micromolar.

Example 7

Treatment of Primary or Secondary Glaucoma and Glaucomatous Retinopathy by Oral Administration of a Compound of this Invention:—A Clinical Trial Early disease: A patient having early ophthalmic manifestations of glaucoma and increased intra-ocular pressure is selected for therapy. The patient weighs 70 kilograms, and if female of child-bearing capacity, is given a pregnancy test to confirm that she is not pregnant. Provided that the patient is not pregnant and does not plan to become pregnant during treatment, a compound of this invention is screened and it's ED50 for PPAR subtypes determined. Using the mathematical algorithm described above, a therapeutically efficacious dose is selected by one skilled in the art. The patient is evaluated by an ophthalmologist experienced in the ophthalmic manifestations of glaucoma and glaucomatous lesions. Regression of the disease or improvement in his clinical status is evaluated by monitoring intraocular pressure, visual fields, and visual reflexes. For more intractable or recalcitrant cases, the daily oral dose is increased about 1 to 3 fold. Additionally, a complete blood count, including white cell count and differential, a platelet count, and liver function tests (such as levels of alkaline phosphatase, lactate dehydrogenase, and aminotransferases) are checked prior to treatment and monthly thereafter. The selected dosage is continued, depending on the response to therapy. The dose may be tapered to a lower (maintenance) dose, again depending on the response to therapy.

Late disease: A similar patient with late ophthalmic manifestations of chronic glaucoma, in particular, with retinal manifestations including maculopathy, retinopathy and retinal ischemia, is selected for therapy. The approach is the same as for the foregoing patient, except that the starting doses are generally higher.

Example 8

Treatment of Optic Neuritis, or a Retinitis, or a Retinopathy, or Macular Degeneration by Oral Administration of a Compound of this Invention—A Clinical Trial Early disease: A patient having early ophthalmic manifestations of retinitis pigmentosa is selected for therapy. The patient weighs 70 kilograms, and if female of child-bearing capacity, is given a pregnancy test to confirm that she is not pregnant. Provided that the patient is not pregnant and does not plan to become pregnant during treatment, a compound of this invention is screened and it's ED50 for PPAR subtypes determined. Using the mathematical algorithm described above, a therapeutically efficacious dose is selected by one skilled in the art. The patient is evaluated by an ophthalmologist experienced in the ophthalmic manifestations of retinitis pigmentosa lesions. Regression of the disease or improvement in his clinical status is evaluated by monitoring the visual fields. Additionally, a complete blood count, white cell count and differential, a platelet count, and liver function tests (such as levels of alkaline phosphatase, lactate dehydrogenase, and aminotransferases) are checked prior to treatment and monthly thereafter. The dosage is tapered to a maintenance dose of 4 mg.

Late disease: A similar patient with late ophthalmic manifestations of retinitis pigmentosa is selected for therapy. The approach is the same as for the foregoing patient, except that the doses are generally higher. After 12 months, the dose is decreased to a lower (maintenance) dose of 4 mg or 8 mg once daily.

Example 9

Therapy for Preventing Acute and Chronic Allograft Rejection—A Clinical Trial A patient who is a candidate for kidney, liver or heart transplantation or other form of organ transplantation is selected for a therapy. The patient may or may not be receiving other therapies for transplant rejection. A compound of this invention, referred to as the test drug, is orally administered in a dosage effective to achieve suppression of T cell activation as known to those with skill in the art. Using the mathematical algorithm described above, a therapeutically efficacious dose is selected by one skilled in the art. Therapy is initiated 2 weeks prior to transplantation. Within 24 to 48 hours post-operatively, therapy with the test drug is resumed and the patient is monitored for changes in symptoms and signs consistent with acute (usually occurring within days) or chronic (within 2 to 6 months) rejection, as known to a practitioner skilled in the art of managing post-transplantation allograft rejection/survival. Additionally, a complete blood count, including white cell count and differential, a platelet count, and plasma IL-2 levels, serum creatinine and BUN levels, liver function tests (such as levels of alkaline phosphatase, lactose dehydrogenase, and transaminases), lipid profile, blood glucose, urinary protein and other tests or evaluations known to a practitioner skilled in the art of managing post-transplantation allograft rejection/survival, are checked prior to allograft transplantation, immediately post-operatively (for monitoring acute rejection) and periodically thereafter for the ensuing months, up to 6 months (for monitoring chronic rejection). Administration of a compound of this invention prevents or decreases signs or symptoms of allograft rejection. The administration of the therapy also enables the clinician to decrease the dose of other conventionally used immunosuppressive agents without increasing the risk of allograft rejection. The patient experiences fewer side effects associated with the other conventional immunosuppressive agents.

Example 10

A Clinical Trial of Synergistic (Adjunctive) Therapy for Preventing Acute and Chronic Allograft Rejection The balance between acute rejection and infection after transplantation continues to be of significant clinical concern, especially during the early post-transplantation period. Acute rejection is a significant risk factor for chronic rejection, and chronic rejection is an important cause of late graft loss. Monoclonal antibodies that selectively block the interleukin-2 receptors on activated T-helper cells are used for immunoprophylaxis or anti-lymphocyte globulins for induction therapy to provide reduced dosing of cyclosporine A throughout the early post-transplantation course.

In the context of the present invention, a PPARgamma agonist, or a PPARgamma/PPARalpha co-agonist of this invention is used as effective adjunctive therapy for preventing acute and chronic allograft rejection. The PPAR-gamma agonist is useful for providing reduced dosing of immunosuppressive therapy, including cyclosporine A, tacrolimus, azathioprine, mycophenolate or other related therapy to preventing allograft rejection throughout both early and late phases post-transplantation. The PPARgamma agonist is used with one or more anti-rejection drug, or in combination with a RXR agonist, or a PPARgamma/RXR agonist, and/or a vitamin D receptor agonist, and/or a glucocorticoid receptor agonist, and/or an estrogen receptor agonist, and/or an androgen receptor agonist.

To achieve a synergistic effect, the treatment can be modified to include combination therapy with a PPAR-gamma/RXR heterodimer ligand (a rexinoid) or another immunosuppressive compound traditionally used for preventing allograft rejection. Examples of such compounds that provide for synergistic effect when given in combination with the drugs encompassed by the current invention include ligands for the glucocorticoid nuclear receptor ligand (e.g. prednisone), inhibitors of purine synthesis (e.g. azathioprine and mycophenolate), and inhibitors of the calcineurin-dependent cytokine synthesis in activated lymphocytes (e.g. cyclosporine, tacrolimus, sirolimus). One or a combination of these compounds are employed (at dosages described above in the section on *Dosage and Schedules*) in clinical trials similar to the one described above in Examples 5 and 6, or in doses sufficient to prevent or treat allograft rejection. Examples of synergistic combinatibns are as follows:

a. A PPARgamma or a PPARalpha/PPARgamma co-activator, both compounds of this invention, is administered in combination with prednisone at an FDA-approved dose.

b. A PPARgamma or a PPARalpha/PPARgamma co-activator is administered in combination with prednisone and cyclosporine A or tacrolimus at an FDA-approved dose, or sirolimus at a dose use in clinical trials.

c. A PPARgamma or a PPARalpha/PPARgamma co-activator is administered in combination with prednisone and cyclosporine A or tacrolimus or sirolimus, and azathioprine or mycophenolate.

d. A PPARgamma or a PPARalpha/PPARgamma co-activator, is administered in combination with one or more FDA-approved immunosuppressive transplant rejection therapeutic compound, as described in examples a, b and c above.

e. A rexinoid PPARgamma/RXR heterodimer ligand (e.g. LG100754) is administered in combination with one or more FDA-approved immunosuppressive transplant rejection therapeutic compound at approved dosages as described in examples a, b and c above.

Example 11

Treatment of Chronic Recalcitrant Multiple Sclerosis by Oral Administration of a Compound of this Invention—A Clinical Trial The following is an example for treating individuals with chronic recalcitrant multiple sclerosis with an PPARgamma or a PPARalpha/PPARgamma co-activator. This method also applies to the treatment of relapsing, remitting multiple sclerosis, to prevent recurrent exacerbations of the disease.

Early disease: The patient presents acutely with the neurological manifestations of multiple sclerosis, and the diagnosis is confirmed by clinical laboratory and pathological diagnostic tests. The patient is evaluated by a neurologist experienced in the clinical and laboratory manifestations of multiple sclerosis lesions. The patient weighs 70 kilograms, and if female of child-bearing capacity, is given a pregnancy test to confirm that she is not pregnant. Provided that the patient is not pregnant and does not plan to become pregnant during treatment, a compound of this invention is screened and it's ED50 for PPAR subtypes determined. Using the mathematical algorithm described above, a therapeutically efficacious dose is selected by one skilled in the art. A compound of this invention is administered daily during the acute episode, and is titrated up 0.5 to 3-fold higher doses at weekly intervals. Regression of the disease or improvement in his clinical status is evaluated by monitoring improvement in motor deficits. Reduction of the systemic inflammation associated with the disease is assessed by performing bi-monthly measurements of high sensitivity-C-reactive protein (hs-CRP). A reduction in the hs-CRP by 50% within 3 months of initiating therapy is considered to be a positive response to the therapy. Additionally, a complete blood count, white cell count and differential, a platelet count, liver function tests (such as levels of alkaline phosphatase, lactate dehydrogenase, and aminotransferases), erythrocyte sedimentation rate and plasma interleukin-2 levels are checked prior to treatment and monthly thereafter. After 6 months treatment, the dosage is tapered to a lower (maintenance) dose.

Example 12

Combination Treatment of a PPAR-Mediated Inflammatory, Proliferative Dermatological (Skin) Disease with PPARgamma Agonist or a Mixed PPARgamma/PPARalpha Agonist (Co-Ligand) and a Vitamin D Derivative—A Clinical Trial The PPAR-mediated disease is an inflammatory, proliferative or degenerative skin disease such as psoriasis, keratitis, hidradenitis, ichthyosis, acne, rosacea, verrucae and other HPV infections, atopic dermatitis, allergic dermatitis, chemical (irritant) dermatitis, seborrheic dermatitis, solar dermatitis, acute and chronic eczema, seborrheic keratosis, senile keratosis, actinic keratosis, photo-induced keratosis, skin aging, thinning skin, dry skin, wrinkle formation, photo-induced skin aging, keloids, lichen planus.

The PPARgamma agonist or mixed PPARgamma/PPARalpha agonist of this invention is administered at doses consistent with the EC50 for PPARalpha and PPARgamma, and with the pharmacokinetic area under the curve (AUC), and is given as a once or twice daily oral dose, or in a pharmaceutical composition for topical administration, with active ingredient at a concentration ranging from 0.01 to 2.0%, 0.25% of the preferred PPAR agonist are selected. An orally administered vitamin D derivative is selected from: dihydrotachysterol (1 mg daily), 1,25-dihydroxycholecalciferol (1 mcg daily), 25-hydroxycholecalciferol (0.1 mg daily), ergocholecalciferol (1.25 mg daily), and cholecalciferol (1 mg daily). Synthetic vitamin D derivatives are administered topically and is selected from the group consisting of calcipotriene and calcitriol (both at a concentration of 0.005% in an ointment or lotion or shampoo). These pharmacological compositions may be used to treat acute or chronic disease or may be used prophylactically to prevent the onset of the disease.

Example 13

Use of Compounds of this Invention as Synergistic (Adjunctive) Therapy in the Treatment of a Neuro-Degenerative Disease or an Autoimmune Disease—A Clinical Trial Multiple sclerosis is the example of the neuro-degenerative, autoimmune disease. Current therapies for MS consist of three interferonbeta preparations (Betaseron, Avonex, and Rebif), Copolymer 1 (Copaxone), and Novantrone. According to this invention, a PPARalpha and/or PPARgamma agonist may be used adjunctively in combination therapy with any of the existing (approved) therapies (identified above) for treating MS. For the purpose of this example, a compound of this invention, a PPARgamma agonist or a PPARgamma/PPARalpha co-agonist, is selected for adjunctive use gap code doses are selected as outlined above. The patient presents acutely with the neurological manifestations of multiple sclerosis, and the diagnosis is confirmed by clinical laboratory and pathological diagnostic tests. The patient is evaluated by a neurologist experienced in the clinical and laboratory manifestations of multiple sclerosis lesions. The patient is a male weighing 70 kilograms or a female weighing 50 kilograms and being treated with an interferonbeta preparation, Copaxone, or Novantrone. An adjunctive PPARgamma agonist, or a PPARalpha and PPARgamma co-agonist (co-activator), is selected from the compounds described in this invention. Adjunctive therapy is initiated at one-half the preferred dose as indicated above. The dose is doubled within 6 to 8 wks of initiation of said adjunctive therapy. The patient is monitored for improvement based on laboratory and clinical findings. The regime is continued as medically indicated to one of skill in the art of treating MS.

Example 14

Assay of PPAR Activity

The ability of representative compounds of this invention to activate PPARgamma was tested in a cell based transactivation assay in vitro system using standard methods familiar to those skilled in the art. The following-Table shows the EC50s for activation of the various PPAR isoforms of the following compound of the current invention.

TABLE A

EC50s for PPAR isoforms by a compound of this invention

| Compound | EC50 for PPAR isoforms |
|---|---|
| BP 107 | PPARgamma < 1nanomolar<br>PPARalpha > 10 micromolar<br>PPARdelta > 10 micromolar |

These findings demonstrate that the representative compound of this invention is an extremely potent activator of PPARgamma. Because many thiazolidinediones and non-thiazolidinediones do not activate PPARgamma, particularly at this extreme level of potency, the current results are surprising. Moreover, the compounds are significantly more effective in activating PPARgamma than rosiglitazone, the most potent ligand for PPARgamma approved for clinical use in the United States. Compounds that activate PPARs are known to be effective in the treatment of a variety of disorders involving alterations in cell proliferation, inflammation, and or disturbances in carbohydrate or lipid metabolism. Thus, the compounds of this invention will have utility for treating and preventing type II diabetes, hypertension, atherosclerosis, restenosis after angioplasty, psoriasis, various malignancies, rheumatoid arthritis, asthma, chronic obstructive pulmonary diseases and other clinical disorders that may be affected by activation of PPARs as described in this document. Because the compounds of the invention are potentially more potent in activating PPARgamma than rosiglitazone, they represent a significant improvement for the treatment of clinical disorders for which rosiglitazone might be used as therapy. Because of the extensive homology between PPARgamma and other isoforms of PPAR (PPARalpha and PPARdelta), the compounds of the invention herein also may be useful for the treatment of clinical disorders influenced by either PPARalpha or PPARdelta or both.

Example 17

Use of a Compound of this Invention to Treat a Metabolic and/or Inflammatory Disease This example illustrates a clinical trial and therapy by oral administration. A patient having type 2 diabetes mellitus, or a dyslipidemia (e.g. hypercholesterolemia or hypertriglyceridemia), or chronic generalized psoriasis, with or without psoriatic arthritis, or rheumatoid arthritis, or inflammatory bowel disease (e.g., ulcerative colitis) is selected for therapy. The patient weighs 80 kilograms. For infants or children the doses suggested are lowered in a linear fashion based on body weight or surface area. The female patient of childbearing potential is given a pregnancy test to confirm that the patient is not pregnant. Provided that the patient is not pregnant and does not plan to become pregnant during treatment, according to this invention, a PPARgamma agonist or a PPARgamma partial agonist (SPARM) or a PPARalpha/PPARgamma dual agonist or a PPARalpha/PPARgamma partial agonist, or a PPARgamma/PPARdelta dual agonist is orally administered in a dosage of 0.1 to 500 milligrams once or twice daily, more typically 2 to 25 mg once or twice daily. The patient is monitored for improvement in the manifestations of the index disease. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is maintained or tapered when the manifestations of the disease subside, as judged by one skilled in the art of medicine.

Example 17

BP107 Shows a Much Better Anti-Psoriatic Effect than Other PPAR Gamma Ligands

Background: Human psoriasis skin engrafted onto severe combined immunodeficient (SCID) mice maintains its abnormal histologic characteristics in the absence of any treatment. Treatment of this SCID mouse, human skin transplant model of psoriasis with anti-psoriatic drugs will improve the histologic phenotype of the transplanted psoriatic skin. Thus, the SCID mouse with transplanted human psoriatic skin represents a useful model of psoriasis and can be used to test the therapeutic effects of antipsoriatic drugs (as described in the following references: 1) Nickoloff B J, Kunkel S L, Burdick M, Strieter R M. Severe combined immunodeficiency mouse and human psoriatic skin chimeras. Validation of a new animal model. *Am J Pathol.* 1995; 146:580-588. 2) Ellis C N, Varani J, Fisher G, Zeigler M E, Pershadsingh H A, Benson S C, Kurtz T W. Troglitazone improves psoriasis and normalizes models of proliferative skin disease: Ligands for peroxisome proliferator activated receptor gamma inhibit keratinocyte proliferation. *Archives of Dermatology* 136:609-616, 2000).

Methods: Keratome pieces of lesional psoriasis skin were transplanted onto immunodeficient mice (such as CB17 strain) as previously described (Nickoloff B J, Kunkel S L, Burdick M, Strieter R M. *Am J Pathol.* 1995; 146:580-588. Ellis C N, Varani J, Fisher G, Zeigler M E, Pershadsingh H A, Benson S C, Kurtz T W. *Archives of Dermatology.* 136:609-616, 2000). The transplanted tissue was allowed to heal for four weeks after which six animals were treated once daily for 4-8 weeks by topical application of BP107 to the psoriatic skin in concentrations sufficient to exert an antipsoriatic effect (concentrations ranging from 0.1 micromolar to 10 millimolar in appropriate amounts of vehicle such as DMSO, propylene glycol, or other vehicles familiar to those skilled in the art). At the end of the treatment period, the animals were sacrificed, tissue pieces were fixed in 10% buffered formalin, embedded in paraffin, sectioned, stained with hematoxylin and eosin, and evaluated histologically using techniques familiar to those skilled in the art. Animals topically treated with the corresponding vehicle without any BP107 were used as controls.

Results: In the animals treated with BP107 topically, the overall skin thickness was reduced, there was a more normal pattern of epidermal differentiation, the granular layer (which is decreased or lacking in the untreated psoriatic skin) was present in much of the epidermis, and the inflammatory response was reduced. This anti-psoriatic effect of BP107 in the treated animals was clearly evident compared to the control animals that were not treated with BP107. Moreover, the antipsoriatic effect of BP107 was much better than that observed in animals treated with weaker PPAR gamma activators such as troglitazone or rosiglitazone. Similar beneficial effects of BP107 can be observed in animal models of other dermatologic disorders including those listed in the tables of this patent application including but not limited to eczema, atopic dermatitis, solar-aged or ultra-violet light aged skin, and various forms of alopecia.

Example 18

Synthesis of Compounds of the Invention

General Procedure for the Preparation of Butanoic Acids:

Sodium bis(trimethylsilyl)amide (2.74 g, 15 mmol) in THF (30 mL) was added to a solution of triethyl 4-phosphonocrotonate (3.75 g, 15 mmol) in THF (20 mL) and the mixture was stirred at ambient temperature for 30 mint. Ketone/aldehyde (10 mmol) in THF (20 mL) was then added and the mixture was stirred at ambient temperature for 90 min. After completion of the reaction, the reaction mixture was quenched with saturated $NH_4Cl$, extracted with EtOAc. The combined organic layers were washed with water, brine and dried over $Na_2SO_4$ and the solvent was evaporated in vacuo.

The crude olefin was dissolved in EtOAc and subjected to hydrogenation with 10% Pd—C at 30 psi and at ambient temperature for 2 h. The mixture was then filtered through Celite and washed with EtOAc, and the solvent was evaporated and purified by column chromatography. Hydrolysis of the resulting ester with LiOH yielded corresponding acid.

4-(4-Phenyl-cyclohexyl)-butyric acid ethyl ester: 49% (two steps); $^1$HNMR ($CDCl_3$, 400 MHz): δ 7.25 (m, 5H);

4.10 (q, 2H); 2.75 (m 0.5H); 2.60 (m, 0.5H); 2.50 (m, 0.5H); 2.30 (t, 2H), 2.12 (m, 0.5H); 1.93 (m, 2.5H); 1.80 (m, 0.5H); 1.67 (m, 6.5H); 1.40 (m, 2H); 1.32 (t, 3H); 1.08 (m, 0.5H).

4-(Decahydro-naphthalen-2-yl)-butyric acid ethyl ester: 69% (two steps); $^1$HNMR (CDCl$_3$, 400 MHz): δ 4.11 (q, 2H); 2.23 (t, 2H), 1.80 (m, 1H); 1.70 (m, 6H); 1.54 (m, 1H); 1.40 (m, 3H); 1.31 (m, 2H); 1.18 (m, 9H); 0.84 (m, 2H).

4-Adamantan-2-yl-butyric acid ethyl ester: 67% (two steps); $^1$HNMR (CDCl$_3$, 400 MHz): δ 4.14 (q, 2H); 2.31 (m, 2H), 2.03 (m, 1H), 1.85 (m, 5H); 1.70 (m, 6H); 1.60 (m, 3H); 1.45 (m, 4H); 1.23 (t, 3H).

General Procedure for the Preparation of Pentanoic Acids:

Sodium bis(trimethylsilyl)amide (2.74 g, 15 mmol) in THF (30 mL) was added to a solution of (4-carboxybutyl) triphenyl phosphonium bromide (6.65 g, 15 mmol) in THF (20 mL) and the mixture was stirred at ambient temperature for 30 min. ketone (10 mmol) in THF (20 mL) was then added and the mixture was stirred at ambient temperature for 90 min. The reaction was quenched with water and followed by extraction with diethyl ether. The aqueous layer was acidified with 10% HCl extracted with EtOAc, washed with saturated aqueous NaCl, dried (Na$_2$SO$_4$) and the solvent was evaporated in vacuo.

The crude olefin was dissolved in EtOAc and subjected to hydrogenation with 10% Pd—C at 30 psi and at ambient temperature for 2 h. The mixture was then filtered through Celite and washed with EtOAc, and the solvent was evaporated and purified by column chromatography.

5-Adamantan-2-yl-pentanoic acid: 65% (two steps); $^1$HNMR (CDCl$_3$, 300 MHz): δ 2.36 (t, 2H); 1.84 (m, 5H); 1.67 (m, 10H); 1.50-1.39 (m, 4H); 1.33 (m, 2H).

5-Cyclohexyl-pentanoic acid: 72% (two steps); $^1$HNMR (CDCl$_3$, 300 MHz): δ 2.31 (t, 2H); 1.57 (m, 8H); 1.31 (m, 2H); 1.12 (m, 5H); 0.82 (m, 2H).

General Procedure for the Preparation of Thiazolidine Amide Derivatives:

In a 250 ml round bottomed flask was taken 0.802 g (2.6 mmol) of hydrochloride salt of 5-({4-[2-(methylamino) ethoxy]phenyl}methyl)-1,3-thiazolidine-2,4-dione in 30 ml of dry dichloromethane. 0.370 ml (2.6 mmol) triethylamine was added at 0° C. and the mixture was stirred at this temperature for an additional 10 minutes. 2.7 mmol of butanoic/pentanoic acid was dissolved in 50 ml of dichloromethane in a separate round bottomed flask and was cooled to 0° C. To this was added 0.370 ml (2.6 mmol) of triethylamine followed by 2.6 ml of isopropyl chloroformate (1M solution in toluene) drop wise over 10 minutes. The mixture was stirred for an additional 10 minutes at this temperature. The mixed anhydride thus formed was canula tranferred to the other flask containing the free amine. The combined mixture was stirred at 0° C. or 1 hr. Water was added and the aqueous layer was extracted with 2×50 ml of dichloromethane. The combined organic layer was washed with 10% sodium bicarbonate and brine. The dichloromethane was removed under vacuum and the residue chromatographed over silica gel (eluent MeOH:CHCl$_3$, 1:99) to yield corresponding amide.

N-{2-[4-(2,4-Dioxo-thiazolidin-5-ylmethyl)-phenoxy]-ethyl}-N-methyl-4-(4-phenyl-cyclohexyl)-butyamide BP-104:

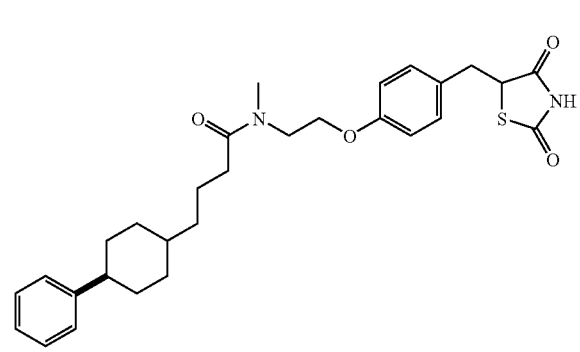

Yield: 63%

$^1$H-NMR (CDCl$_3$ 400 MHz): 9.91 (bs, 1H); 7.30-7.11 (m, 7H); 6.83 (d, J=8.6 Hz, 2H); 4.44 (dd, J=3.7 Hz, 9.6 Hz, 1H); 4.11 (t, J=6.7 Hz, 2H); 3.75 (t, J=6.9 Hz, 2H); 3.45 (dd, J=3.7 Hz, 12.8 Hz, 1H); 3.16 (s, 3H); 3.04 (dd, J=9.5 Hz, 14.1 Hz, 1H); 2.50 (m, 0.5H); 2.46 (m, 1H); 2.36 (t, 2H); 2.10 (m, 1H); 1.90 (m, 1.51H); 1.64 (m, 7H); 1.46 (2H); 1.28 (m, 1H).

$^{13}$C-NMR (CDCl$_3$ 100 MHz): 23.6(t), 29.2(t, 2C), 30.4(t), 33.8(d, 0.5C), 34.4(t), 34.6(d, 0.5C), 38.1(t), 38.2(q), 44.8(d, 0.5q), 45.1(d, 0.5C), 48.2(t), 54.2(d), 67.1(t), 115.1(d, 2C), 126.1(d), 127.4(d, 2C), 128.7(s), 128.8(d, 2C), 130.9(d, 2C), 147.9(s), 158.4(s), 171.5(s), 174.4(s), 175.3(s).

4-(Decahydro-naphthalen-2-yl)-N-{2-[4-(2,4-dioxo-thiazolidin-5-ylmethyl)-phenoxy]-ethyl}-N-methyl-butyramide, BP-105:

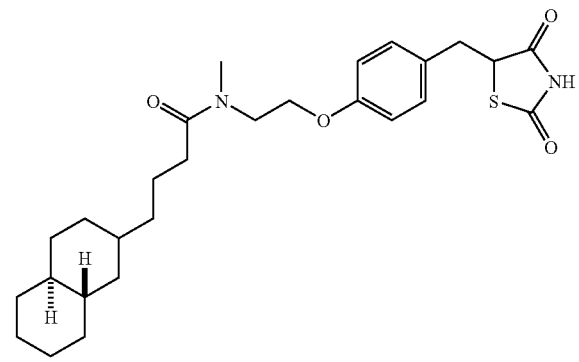

Yield: 71%

$^1$H-NMR (CDCl$_3$ 400 MHz): 10.0 (bs, 1H); 7.13 (d, J=8.08 Hz, 2H); 6.81 (d, J=8.6 Hz, 2H); 4.43 (dd, J=3.6 Hz, 9.63 Hz, 1H); 4.05 (t, 2H); 3.72 (t, 2H); 3.45 (dd, J=3.0 Hz, 14 Hz, 1H); 3.16 (s, 3H); 3.03 (dd, J=9.5 Hz, 14 Hz, 11); 2.29 (t, 2H); 1.64 (m, 6H); 1.44 (m, 7H); 1.23 (m, 6H); 0.91 (m, 2H).

$^{13}$C-NMR (CDCl$_3$ 100 MHz): 21.4(t), 22.8(t), 26.2(t), 27.5(t), 28.1(t), 32.8(t), 32.9(t), 33.0(t), 34.3(t), 34.5(d), 36.3(d), 36.4(d), 38.1(q), 38.3(t, 2C), 38.6(d), 48.4(t), 54.2 (d), 67.1(d), 115.0(d, 2C), 128.7(s), 130.8d, 2C), 158.4(s) 171.5(s), 174.5(s), 175.4(s).-

5-Adamantan-2-yl-pentanoic acid {2-[4-(2,4-dioxo-thia-zolidin-5-ylmethyl)-phenoxy]-ethyl}-methyl-amide, BP-107:

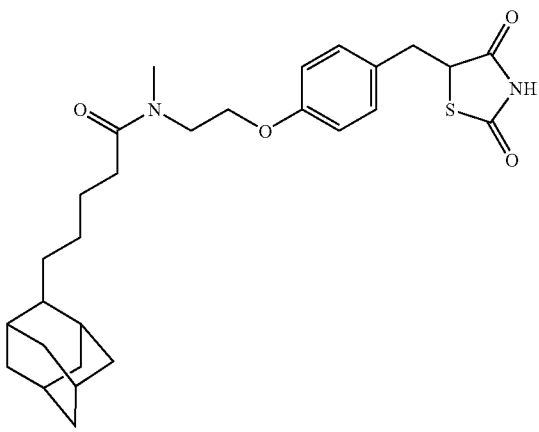

Yield: 79%

$^1$HNMR (CDCl$_3$ 400 MHz): 10.4 (bs, 1H); 7.10 (d, J=8 Hz, 2H); 6.78 (d, J=8.6 Hz, 2H); 4.38 (dd, J=3.7 Hz, 9.6 Hz, 1H); 4.05 (t, J=6.7 Hz, 2H); 3.69 (t, J=6.7 Hz, 2H); 3.43 (dd, J=3.7 Hz, 14.2 Hz, 1H); 3.11 (s, 3H); 3.00 (dd, J=9.5 Hz, 13.8 Hz, 1H); 2.31 (t, J=7.4 Hz, 2H); 1.78 (m, 6H); 1.57 (m, 9H); 1.41 (m, 4H); 1.24 (m, 2H).

$^{13}$CNMR (CDCl$_3$ 100 MHz): 25.7(t), 27.8(t), 28.5(d), 28.8(d), 32.0(t, 2C), 32.3(q), 32.8(t), 34.0(t), 34.5(d), 38.0 (d), 38.3(t), 38.9(t), 39.6(t, 2C), 44.6(d), 48.4(t), 54.2(d), 67.0(t), 115.0(d, 2C), 128.8 (s), 130.7(d, 2C), 158.4(s), 171.6(s), 174.6(s), 175.5(s).

Diseases or Disorders Treatable with Methods Described in this Invention

Tables I through X provides further examples of diseases or disorders treatable with methods described in this invention:

TABLE II

Examples of psychiatric disorders treatable using compounds described in this invention Depression, primary depression or depression secondary to chronic diseases and medications
Dysphoric mood disorders
Obsessive compulsive disorder
Dysthymic disorders
Manic depressive (unipolar or bipolar) disorder
Anxiety states including panic disorder and agoraphobia
Post menstrual syndrome
Schizophrenia
Chronic fatigue syndrome
Substance abuse and drug addiction
Anorexia nervosa and anorexia bullemia

TABLE III

Examples of neurological/neurodegenerative disorders treatable using compounds described in this invention Migraine headaches (e.g. vascular headaches, common migraine)
Primary (e.g. Alzheimer's disease) and secondary (e.g. HIV-related) dementias
Degenerative CNS diseases (e.g. Parkinson's disease, amyotropic lateral sclerosis)
Demyelinating diseases (e.g.multiple sclerosis, Guillain-Barre syndrome)
Pain disorders including algesia, hyperalgesia, acute and chronic pain, allodynia
Primary and secondary encephalitis and encephalomyelitis (e.g. autoimmune encephalomyelitis, allergic encephalomyelitis)
Primary and secondary neuritis, autoimmune neuritis
Other autoimmune diseases (e.g. myesthenia gravis, Eaton-Lambert syndrome)
Congenital and secondary ataxias

TABLE I

Examples of dermatological disorders treatable using compounds described in this invention Keratinizing skin diseases, keratitis, hidradenitis, ichthyosis
Psoriasis (all forms, including *p. vulgaris, p. guttata, p. discoidea, p. anthropica, p. universalis, p. pustulosa, p. annularis, p. palmaris, p. diffusa*, and *p. punctate*)
Acne (all forms, including *a. vulgaris, a. rosacea, a. inversa*, cystic acne)
Warts, verruca (all forms, including common warts, anogenital (venereal) warts, viral warts including human papilloma virus (HPV) infections, conjunctival warts, Oral/buccal warts)
Acute and chronic dermatitides (inflammation of the skin), atopic dermatitis, allergic dermatitis, contact dermatitis, cosmetic dermatitis, chemical dermatitis, seborrheic dermatitis, solar dermatitis, acute and chronic eczema, diaper rash, sunburn
Lupus associated skin lesions
Keratoses such as seborrheic keratosis, senile keratosis, actinic keratosis, photo-induced keratosis, skin aging, thinning skin, dry skin, wrinkle formation, photo-induced skin aging, keratosis follicularis
Keloids and prophylaxis against keloid formation
Leukoplakia, lichen planus
Urticaria, pruritus
Androgenic alopecia in men and women, hirsutism in women

TABLE IV

Examples of inflammatory and metabolic disorders associated with allograft ransplantation treatable using compounds described in this invention The compounds described herein are useful as monotherapy or adjunctive therapy with existing immunosuppressive agents for the promotion and maintenance of allograft survival, post-transplantation.
Examples of inflammatory and proliferative conditions or diseases associated with allograft transplantation and immune suppression include:
1. Acute allograft rejection
2. Chronic allograft rejection
3. Graft versus host disease
4. Post-transplantation de novo malignancy (e.g. lymphoma and epidermal cancers)
5. Osteoporosis and osteopenia
6. Hyperlipidemia
7. Insulin resistance and diabetes mellitus
8. Hypertension
9. Atherosclerosis
10. Endarteritis associated with heart allograft transplantation
11. Glomerulonephritis associated with renal allograft transplantation
12. Cardiomyopathy and congestive heart failure associated with allograft transplantation, in particular heart transplantation

TABLE V

Examples of diseases of various organ systems treatable using compounds described in this invention

| Organ System | Disease/Pathology |
|---|---|
| Cardiovascular | Hypertension, vasculo-occlusive diseases including atherosclerosis, arteritis, endarteritis, endocarditis, myocarditis, arterial plaque (fibrous cap) rupture, thrombosis, restenosis after any invasive vascular procedures; acute coronary syndromes such as unstable angina, myocardial infarction, myocardial ischemia and other ischemic cardiomyopathies, non-ischemic cardiomyopathies, post-myocardial infarction cardiomyopathy and myocardial fibrosis, drug-induced cardiomyopathy. |
| Endocrine | Obesity, type 1 diabetes mellitus, type 2 diabetes mellitus, gestational diabetes, impaired glucose tolerance, Cushing's syndrome (e.g. secondary to chronic glucocorticoid therapy), polycystic ovarian syndrome, osteoporosis, osteopenia, accelerated aging of tissues and organs, e.g. Werner's syndrome. |
| Urogenital | Prostatitis, endometritis, endometriosis, benign prostatic hypertrophy, leiomyoma, polycystic kidney disease (e.g. autosomal dominant PKD), acute tubular necrosis, nephrotic syndrome, diabetic nephropathy, glomerulonephritis, erectile dysfunction in men and women. |
| Pulmonary | Asthma, chronic obstructive pulmonary disease (COPD), reactive airway disease, pulmonary fibrosis, pulmonary hypertension. |
| Connective tissue Joint | Rheumatoid arthritis, Raynaud's phenomenon/disease, Sjogren's syndrome, systemic sclerosis, systemic lupus erythematosus, inflammatory bowel disease (ulcerative colitis, Crohn's disease) vasculitides, ankylosing spondylitis, osteoarthritis, reactive arthritis, psoriatic arthritis, fibromyalgia, osteoarthritis, sarcoidosis. |
| Liver/Other | Hepatic fibrosis, hepatic cirrhosis, hepatic steatosis, all etiologies, e.g. alcohol-induced (e.g. ethanol), drug-induced (e.g. tylenol), and toxin-induced (e.g. mushroom poisoning)<br>Fibrocystic breast disease, fibroadenoma |

TABLE VIa

Examples of neoplastic diseases treatable using compounds described in this invention

| Organ System | Malignancy/Cancer type |
|---|---|
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone receptor positive or negative subtypes, soft tissue tumors. |
| Metastasis | Metastases resulting from all neoplasms. |
| Other | Angiomata, angiogenesis associated with the neoplasms. |

TABLE VIb

Further examples of neoplastic diseases treatable using compounds described in this invention

| Location | Malignancy/Cancer type |
|---|---|
| Various | fibrosarcoma, myxosarcoma, liposarcoma, chondrosarcoma, osteogenic sarcoma, chordoma, angiosarcoma, enthotheliosarcoma, lymphangiosarcoma, |

TABLE VIb-continued

Further examples of neoplastic diseases treatable using compounds described in this invention

| Location | Malignancy/Cancer type |
|---|---|
| | lymphangioendotheliosarcoma, synovioma, mesothelimoa, Ewing's tumor, leiomyosarcoma, rhabdomyosarcoma, colon carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. |

TABLE VII

Examples of viral infections and related pathologies treatable according to the methods of this invention

| Virus | Viral infection/cancer or other virus-associated pathology |
|---|---|
| HTLV | T-cell leukemia/lymphoma, HTLV-associated arthritides/myelopathies. |
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, varicella-zoster, chicken pox, herpes zoster, post-herpetic neuralgia, conjunctivitis, keratoconjunctivitis, keratitis. |
| HHV | Exanthem subitum, infectious mononucleosis. |
| EBV | Infectious mononucleosis, chronic fatigue syndrome, lymphoma, conjunctivitis, keratitis, and related infections of the eye. |
| Adenoviruses | Upper and lower respiratory tract infections, pneumonia, conjunctivitis. |
| RSV | Upper and lower respiratory tract infections, pneumonia. |
| PMV | Mumps and related manifestations, e.g., conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumonia. |

HIV, Human Immunodeficiency Virus;
HTLV, Human T-cell Lymphocyte Virus;
HPV, Human Papilloma Virus;
HAV, Hepatitis A Virus;
HBV, Hepatitis B Virus;
HAV, Hepatitis C Virus;
CMV, Cytomegalovirus;
HSV, Herpes Simplex Virus (Types I & II);
HHV, Human Herpes Virus;
EBV, Epstein-Barr Virus;
RSV, Respiratory Syncytial Virus;
VZV, Varicella-Zoster Virus;
PMV, Paramyxovirus;
MV, Measles (Rubeola) Virus;
RV, Rubella Virus

TABLE VIII

HIV related infections and diseases treatable using compounds described in this invention

| Organ system | Viral infection/manifestation or other HIV-associated disease |
|---|---|
| Immunologic | AIDS, primary HIV infection. |
| Dermatological | Anogenital cancers including rectal and cervical cancer, Kaposi's |

TABLE VIII-continued

HIV related infections and diseases treatable using compounds described in this invention

| Organ system | Viral infection/manifestation or other HIV-associated disease |
|---|---|
| | sarcoma, atopic dermatitis, squamous cell carcinoma, hairy leukoplakia, molluscum contagiosum, warts (HPV infections), seborrheic dermatitis, psoriasis, xeroderma, HSV and varicella-zoster infections. |
| Hematologic | Non-Hodgkin's lymphoma, B cell lymphoma, anemia, neutropenia, thrombocytopenia. |
| Gastrointestinal | Anorexia, gastroparesis, diarrhea, malabsorption, gastrointestinal CMV infections, esophagitis, colitis, hepatitis, lymphoma. |
| Ophthalmic | Conjunctivitis, keratitis, keratoconjunctivitis, uveitis, retinitis, chorioretinitis, CMV retinitis, iridocyclitis, vitreitis, choroiditis, papilledema, Kaposi's sarcoma, lymphoma, ocular palsies, conjunctival warts, pre-neoplastic and neoplastic diseases of the eye. |
| Cardiac | Myocarditis, endocarditis, pericarditis. |
| Pulmonary | CMV pneumonitis, lymphoid interstitial pneumonitis. |
| Nephrologic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome, chronic pain, psychoses, substance abuse disorders and drug addiction. |
| General | Lymphoma, metastatic lymphoma, Kaposi's sarcoma, wasting syndrome, psychosis. |

TABLE IX

Diseases of the eye treatable using compounds described in this invention

| Disease | Virus |
|---|---|

1. Inflammatory eye diseases associated with viral infections

| | |
|---|---|
| Blepharitis | HSV, VZV, Vaccinia, HPV, molluscum contagiosum |
| Conjunctivitis | HSV, VZV, EBV, Adenovirus, Vaccinia, Variola, HPV, molluscum contagiosum, influenza |
| Follicular c. | Newcastle, measles, mumps, rubella, molluscum contagiosum |
| Hemorrhagic c. | Enterovirus, coxsackie |
| Catarrhal c | Rubella |
| Keratitis | HSV, VZV, EBV, Adenovirus, Vaccinia, Variola, HPV, molluscum contagiosum |
| Keratoconjunctivitis | HSV, VZV, EBV, Adenovirus, Vaccinia, Variola, HPV, molluscum contagiosum |
| Retinitis | CMV |
| Uveitis | HPV |
| Conjunctival warts | HPV |
| C. epithelial neoplasms | HPV |

2. Oularplastic diseases

| | |
|---|---|
| Benign tumors: | Keratocanthoma, molluscum contagiosum, dermoid cysts, neurofibroma, neurofibromatosis, schwannoma (neurilemoma), pleiomorphic adenoma |
| Malignant tumors: | Basal cell carcinoma, squamous cell carcinoma, mucoepidermoid carcinoma, melanoma, retinoblastoma, embryonal rhabdomyosarcoma, meningioma, adenoid cystic carcinoma, lymphoid tumors of the orbit, mesenchymal tumors (fibrous hystiocytoma) of the orbit, nasopharyngeal carcinoma. |
| Vascular lesions: | Hemangioma, lymphangioma. |

Ophthalmic diseases treatable using compounds described in this invention
Disease Category/Examples of Diseases, Causes or Associated Conditions*

| | |
|---|---|
| Conjunctivitis | Acute allergic conjunctivitis (e.g. drug-related inflammation, hypersensitivity reactions), chronic (vernal) conjunctivitis, contact lens-associated conjunctivitis, e.g. giant papillary |

TABLE IX-continued

| | |
|---|---|
| | conjunctivitis, conjunctival ulceration, including ulceration associated with mucous membrane, conjunctival warts |
| Blepharitis | Inflammatory etiologies, e.g. blepharitis secondary to rosacea |
| Ophthalmic fibrosis | Steven's-Johnson syndrome with progressive fibrosis and scarring, cicatrization and symblepharon. |
| Corneal injury | Corneal abrasion or ulceration (e.g. contact lens-related injury), or corneal injury of any etiology*. |
| Dry eye syndrome | See Table below<br>Pterygium, pinguecula<br>PemphigoidIncludes ophthalmic pemhigori<br>Scleritis/Episcleritis<br>Iridocyclitis<br>Endophthalmitis |
| Uveal tract diseases | Including glaucoma (primary and secondary etiologies) Uveitis, uveoretinitis, panuveitis, all etiologies* |
| Vitreitis, retinitis | e.g. congenital retinitis, retinitis pigmentosa |
| Infectious retinitis | Viral (e.g. herpes, cytomegalovirus, HIV), tuberculous, syphititic, fungal (e.g. histoplasmosis) |
| Chorioretinopathies | Chorioretinitis, choroiditis, vitreitis, |
| Retinopathies | e.g. Diabetic retinopathy, hypertensive retinopathy Maculopathiesage-related-macular degeneration, white dot syndromes |
| Cataract | Related to diabetes, age, collagen vascular diseases Ocular palsies |

*Etiologies of ophthalmic diseases treatable according to the methods of this invention include diseases induced or caused by physical agents (e.g. UV radiation), chemical agents (e.g. acids, caustic solvents) immunological etiologies (e.g. collagen vascular diseases, auto-immune, T lymphocyte-related), infectious agents such as viruses (HSV, CMV, HIV), mycoplasma, tuberculosis, syphilis, fungae (histoplasmosis)

Etiologies of dry eye syndrome

I. Conditions Characterized by Hypofunction of the Lacrimal Gland:
    A. Congenital
        Familial dysautonomia (Riley-Day syndrome), aplasia of the lacrimal gland (congenital alacrima), trigeminal nerve aplasia, ectodermal dysplasia
    B. Acquired
        1. Systemic Diseases, e.g. Sjogren's Syndrome, progressive systemic sclerosis, sarcoidosis, leukemia, lymphyoma, amyloidosis, hemochromatosis,
        2. Infection, e.g. mumps
        3. Injury, e.g. surgical removal of lacrimal gland, irradiation, chemical burn
        4. Medications, e.g. antihistamines, antimuscarinics (atropine, scopolamine), general anesthetics (halothane, nitrous oxide), beta-adrenergic blockers (timolol, practolol), neurogenic, neuroparalytic (facial nerve palsy)
II. Conditions Characterized by Mucin Deficiency
    Avitaminosis A, Stevens-Johnson syndrome, ocular pemphigoid, chronic conjuncitivitis (e.g. trachoma), chemical burns, drugs and medications
III. Conditions Characterized by Lipid Deficiency
    Lid margin scarring, blepharitis
IV. Defective Spreading of Team Film Caused by the Following:
    A. Eyelid abnormalities
    1. Defects, colboma
    2. Ectropion or entropion
    3. Keratinization of lid margin
    4. Decreased or absent blinking secondary to: neurologic disorders, hyperthyroidism, contact lens, drugs and medications, herpes simplex keratitis, leprosy, conjunctival abnormalities, pterygium, symblepharon, proptosis

Non-hereditary and hereditary degenerative diseases

| | |
|---|---|
| Macular disorders: | All etiologies and manifestations, including age-related macular degeneration, exudative macular degeneration, atrophic macular degeneration, crystalline retinopathies, retinal toxicosis of systemic medications, idiopathic central serous choroidiopathy, macular edema |
| Retinovascular diseases and retinopathies: | Retinopathy, vasculo-occlusive r., ischemic r., idiopathic r., hypertensive r., proliferative r., diabetic r., vitreoretinopathy, vasculopathies associated with telangiectasias or aneurysms, retinopathies associated with lupus erythematosus, rheumatoid arthritis, multiple sclerosis, myasthenia gravis, uveoretinitis or diabetes mellitus, glaucomatous retinopathies |

TABLE IX-continued

Glaucoma: All etiologies and manifestations, including primary and secondary open-angle glaucoma, angle-closure glaucoma, glaucoma associated with intraocular inflammation, elevated intraocular pressure associated with acute glaucoma, steroid-induced glaucoma, glaucoma associated with intraocular hemorrhage, pseudoexfoliative syndrome, glaucomatous optic neuropathy and other degenerative changes (e.g. retinopathy) associated with glaucoma Cataract: All etiologies and manifestations, including age-related (UV radiation) cataract, cataract associated with systemic diseases such as collagen vascular disease, diabetes mellitus, Wilson's disease Other diseases: Primary or secondary retinal detachment
Congenital degenerative retinopathies 1. Primary pigmented retinopathies, all gene types
   Autosomal dominant retinitis pigmentosa, e.g. rod-cone and cone-rod degenerations
   Autosomal recessive retinitis pigmentosa, e.g. rod-cone and cone-rod degenerations, Lerner's amaurosis congenita
   X-linked recessive pigmented retinopathies, e.g. choroideremia
2. Secondary pigmented retinopathies (retinopathies associated with systemic diseases)
   Autosomal dominant pigmented retinopatbies, e.g. Paget's disease, Charcot-Marie-Tooth, disease, Steinert's disease, Pierre-Marie syndrome
   Autosomal recessive pigmented retinopathies, e.g. diabetes mellitus, mannosidoses, mucopolysccharidoses, Batten's d., Refsum's d., Usher syndrome
   X-linked recessive pigmented retinopathies, e.g. Hunter syndrome

TABLE X

Diseases or conditions treatable using compounds described in this invention

I. Promote healing in the following clinical situations:
   Surgical or traumatic wounds to healthy tissues or organs
   Wounds caused by chemical or physical agents, e.g. ulcers caused by caustic or erosive chemicals, pressure sores, etc.
   Wounds associated with disease states, e.g. diabetic ulcers etc.
   Wounds in diseased tissues or organs
II. Promote cell survival and prevent apoptosis in neurodegenerative diseases:
   Alzheimer's disease
   Parkinson's disease
   Amyotrophic lateral sclerosis
   Spinal cord injury or transection secondary to trauma or disease
III. Attenuation or arrest of the following conditions or processes:
   The natural aging of cells and tissues
   Aging induced by chemical or physical agents, e.g. sun-induced skin aging
   Accelerated aging associated with diseases, e.g. Werner's syndrome
IV. Vitalization and revitalization of organs and tissues
   Promoting cell growth and preventing cell death in the aging process
   Promoting therapeutic or non-pathological angiogenesis as a therapeutic approach to treating diseases such as congestive heart failure and cardiomyopathy
   Promoting growth of organs and tissues for repair or transplantation

REFERENCES

Technical background for the methods of synthesis and therapeutic use of compounds of the present invention are described in the following provisional patent applications, patent applications, patents, published applications and publications:

U.S. Pat. No. 09/520,208
U.S. Provisional Appl. No. 60/157890
U.S. Pat. No. 6,150,371
U.S. Pat. No. 6,103,742
U.S. Pat. No. 6,100,403
U.S. Pat. No. 6,087,385
U.S. Pat. No. 6,087,384
U.S. Pat. No. 6,028,088
U.S. Pat. No. RE36,575
U.S. Pat. No. 6,022,897
U.S. Pat. No. 6,011,036
U.S. Pat. No. 6,011,031
U.S. Pat. No. 6,008,237
U.S. Pat. No. 5,990,139
U.S. Pat. No. 5,985,884
U.S. Pat. No. 5,977,365
U.S. Pat. No. 5,972,970
U.S. Pat. No. 5,972,959
U.S. Pat. No. 5,965,589
U.S. Pat. No. 5,962,470
U.S. Pat. No. 5,952,509
U.S. Pat. No. 5,965,584
U.S. Pat. No. 5,952,356
U.S. Pat. No. 5,939,442
U.S. Pat. No. 5,932,601
U.S. Pat. No. 5,925,656
U.S. Pat. No. 5,910,592
U.S. Pat. No. 5,902,726
U.S. Pat. No. 5,889,032
U.S. Pat. No. 5,889,025
U.S. Pat. No. 5,886,014
U.S. Pat. No. 5,885,997
U.S. Pat. No. 5,869,495
U.S. Pat. No. 5,859,051
U.S. Pat. No. 5,847,008
U.S. Pat. No. 5,843,970
U.S. Pat. No. 5,834,501
U.S. Pat. No. 5,827,865
U.S. Pat. No. 5,824,694
U.S. Pat. No. 5,811,439
U.S. Pat. No. 5,801,173
U.S. Pat. No. 5,741,803
U.S. Pat. No. 5,693,651
U.S. Pat. No. 6,090,836

-continued

U.S. Pat. No. 6,057,343
U.S. Pat. No. 6,037,359
U.S. Pat. No. RE36,575
U.S. Pat. No. 6,028,109
U.S. Pat. No. 5,994,554
U.S. Pat. No. 5,935,934
WO 00/053601A1 Sep. 14, 2000
WO 00/037077A1 Jun. 29, 2000
WO 00/000194A1 Jan. 06, 2000
WO 00/027832A2 May 18, 2000
WO 00/023407A2 Apr. 27, 2000
WO 00/008002A1 Feb. 17, 2000
WO 09/948915a1 Sep. 30, 1999

Takada I, et al. Mol Endocrinol. 2000; 14: 733-40.
Kliewer SA, et al. Proc Natl Acad Sci USA. 1997; 94: 4318-23.
Buckle DR, et al. Bioorg Med Chem Lett 1996; 6: 2121-6.
Buckle DR, et al. Bioorg Med Chem Lett 1996; 6: 2127-30.
Kliewer SA, et al. Recent Prog Horm Res. 2001; 56: 239-63.
Gampe RT, et al. Mol Cell. 2000; 5: 545-55.
Barroso I, et al. Nature. 1999; 402: 880-3.
Causevic M, et al. FEBS Lett. 1999; 463: 205-10.
Uppenberg J, et al. J Biol Chem. 1998; 273: 31108-12.
Nichols JS, et al. Anal Biochem. 1998; 257: 112-9.
Zhou G, et al. Mol Endocrinol. 1998; 12: 1594-604..
Hamann LG. J Org Chem 2000; 65: 3233-5.
Yanagi, Y., et al., (2000) Biochem. Cell Biol. 269, 410-414

All publications, patents and patent applications referred to herein are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary.

What is claimed is:

1. A compound having the formula:

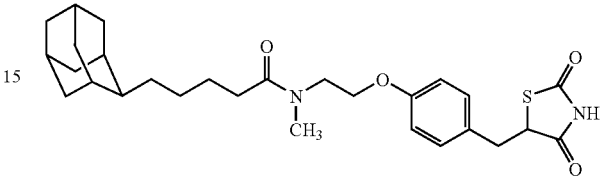

or a salt, solvate, tautomer or stereoisomer thereof.

2. A pharmaceutical composition comprising a compound of claim 1 or a salt, solvate, tautomer or stereoisomer thereof and a pharmaceutical acceptable excipient.

3. A method for treating psoriasis, the method comprising administering to a human or an animal in need thereof, a therapeutically effective amount of a compound according to claim 1.

4. The method according to claim 3, wherein the compound is administered in combination with a natural or a synthetic therapeutic compound.

5. The method according to claim 3, wherein the psoriasis is selected from the group consisting of *p. vulgaris, p. guttata, p. discoidea, p. anthropica, p. universalis, p. pustulosa, p. annularis, p. palmais, p. difusa*, and *p. punctate*.

6. A method for treating psoriasis, the method comprising administering to a human or an animal in need thereof, a therapeutically effective amount of a composition according to claim 2.

* * * * *